(12) United States Patent
Dong et al.

(10) Patent No.: US 7,589,058 B2
(45) Date of Patent: Sep. 15, 2009

(54) GHRELIN ANALOGS

(75) Inventors: Zheng Xin Dong, Holliston, MA (US); Yeelena Shen, Franklin, MA (US)

(73) Assignee: Ipsen Pharma, S.A.S., Boulogne-Billancourt (FR)

( * ) Notice: Subject to any disclaimer, the term of this patent is extended or adjusted under 35 U.S.C. 154(b) by 472 days.

(21) Appl. No.: 10/522,398

(22) PCT Filed: Jul. 23, 2003

(86) PCT No.: PCT/US03/22925

§ 371 (c)(1), (2), (4) Date: Jan. 21, 2005

(87) PCT Pub. No.: WO2004/009616

PCT Pub. Date: Jan. 29, 2004

(65) Prior Publication Data

US 2005/0272648 A1    Dec. 8, 2005

Related U.S. Application Data

(60) Provisional application No. 60/397,834, filed on Jul. 23, 2002, provisional application No. 60/427,488, filed on Nov. 19, 2002.

(51) Int. Cl.
*A61K 38/04* (2006.01)
*A61K 38/16* (2006.01)
(52) U.S. Cl. ............... 514/2; 514/12; 514/13; 514/14; 514/15; 514/16; 514/17; 530/324; 530/325; 530/326; 530/327; 530/328; 530/329
(58) Field of Classification Search ............ None
See application file for complete search history.

(56) References Cited

U.S. PATENT DOCUMENTS 7,385,026 B1 * 6/2008 Kangawa et al. ............ 530/324

FOREIGN PATENT DOCUMENTS

| EP | 1 197 496 | | 4/2002 |
|---|---|---|---|
| WO | 97/21730 | | 6/1997 |
| WO | 01/07475 | | 2/2001 |
| WO | WO01/07475 | * | 2/2001 |
| WO | 01/92292 | | 12/2001 |
| WO | WO01/92292 | * | 12/2001 |
| WO | 02/08250 | | 1/2002 |
| WO | 02/083860 | | 10/2002 |

OTHER PUBLICATIONS

Asakawa, A. et al., "Ghrelin is an appetite-stimulatory signal from stomach with structural resemblance to motilin," Gastoenterology, 2001, 120:337-345.
Bednarek, M. et al., "Structure-function studies on the new growth hormone-releasing peptide, ghrelin: minimal sequence of ghrelin necessary for activation of growth hormone secretagogue receptor 1a," J. Med. Chem., 2000, 43:4370-4376.
Bowers, C. Y., "Unnatural growth hormone-releasing peptide begets natural ghrelin," J. Clinical Endo. & Metab., 2001, 86:1464-1469.
Cummings, D. et al., "Plasma ghrelin levels after diet-induced weight loss or gastric bypass surgery," N. Engl. J. Med., 2002, 346:1623-1630.
Dieguez, C. et al., "Ghrelin: a step forward in the understanding of somatotroph cell function and growth regulation," European J. Endocrinology, 2000, 142:413-417.
Flier, J. et al., "The stomach speaks—ghrelin and weight regulation," N. Engl. J. Med., 2002, 346:1662-1663.
Kaiya, H. et al., "Bullfrog ghrelin is modified by n-octanoic acid at its third threonine residue," J. Biol. Chem., 2001, 276:40441-40448.
Kojima, M. et al., "Ghrelin is a growth-hormone-releasing acylated peptide from stomach," Nature, 1999, 402:656-660.
Matsumoto, M. et al., "Structure-activity relationships of ghrelin endogenous growth hormone secretagogue," Peptide Science, 2000, p101-104.
Matsumoto, M. et al., "Structural similarity of ghrelin derivatives to peptidyl growth hormone secretagogues," Biochem. Biophys. Res. Comm., 2001, 284:655-659.
Papotti, M. et al., "Growth hormone secretagogue binding sites in peripheral human tissues," J. Clin. Endo. & Metab., 2000, 85:3803.
Peino, R. et al., "Ghrelin-induced growth hormone secretion in humans," European J. Endocrinolgy, 2000, 143:R11-R14.
Svensson, J., "Growth hormone secretagogues as therapeutic agents," Growth Hormone & IGF Res., 1999, 9:107-109.
Takaya, K. et al., "Ghrelin strongly stimulates growth hormone (GH) release in humans," J. Clinical Endo. & Metab., 2000, 85:4908-4911.
Tolle, V. et al., "In vivo and in vitro effects of ghrelin/motilin-related peptide on growth hormone secretion in the rat," Neuroendocrinology, 2001, 73:54-61.
Wisse, B. et al., "Reversal of cancer anorexia by blockade of central melanocortin receptors in rat," Endocrinology, 2001, 142:3292-3301.
Wren, A. et al., "The novel hypothalamic peptide ghrelin stimulates food intake and growth hormone secretion," Endocrinology, 2000, 141:4325-4328.
Wren, A. et al., "Ghrelin causes hyperphagia and obesity in rats," Diabetes, 2001, 50:2540-2547.
Matsumoto, M. et al., "Structure-activity relationship of ghrelin: pharmacological study of ghrelin peptides," Biochem. Biophys. Res. Com., 2001, 287:142-146.
Chemical Abstracts Accession No. 473287-63-7 Nov. 12, 2002.
Church, W. B. et al., "A novel approach to the design of inhibitors of human secreted phospholipase A2 based on native peptide inhibition", J. Biol. Chem., 2001, 276:33156-33164.
Guo, D. et al., "Prediction of peptide retention times in reversed-phase high-performance liquid chromatography II. Correlation of observed and predicted peptide retention times and factors influencing the retention times of peptides", J. Chromatography, 1986, 359:519-532.
Kagan, H. M. et al., "Influence of sequence and charge on the specificity of lysyl oxidase toward protein and synthetic peptide substrates", J. Biol. Chem., 1984, 259:11203-11207.
Torsello, A. et al., "Short ghrelin peptides neither displace ghrelin binding in vitro nor stimulate GH release in vivo", Endocrinology, 2002, 143:1968-1971.

* cited by examiner

*Primary Examiner*—Anish Gupta
(74) *Attorney, Agent, or Firm*—Yankwich & Associates; Alan F. Feeney; Tony K. Uhm

(57) ABSTRACT

The invention comprises peptidyl analogs that possess agonist or antagonist ghrelin activity, along with therapeutic and non-therapeutic uses thereof.

16 Claims, No Drawings

GHRELIN ANALOGS

This application is a United States national filing under 35 U.S.C. §371 of international (PCT) application No. PCT/US2003/022925, filed Jul. 23, 2003, designating the US, and claiming priority to U.S. provisional application 60/397,834 filed Jul. 23, 2002 and U.S. provisional application 60/427,488 filed Nov. 19, 2002.

BACKGROUND OF THE INVENTION

The pulsatile release of growth hormone from the pituitary somatotrops is regulated by two hypothalamic neuropeptides: growth hormone-releasing hormone and somatostatin. Growth hormone-releasing hormone stimulates release of growth hormone, whereas, somatostatin inhibits secretion of growth hormone (Frohman et al., *Endocronol. Rev.* 1986, 7, 223-253, and Strobi et al., *Pharmacol. Rev.* 1994, 46, 1-34).

Release of growth hormone from the pituitary somatotrops can also be controlled by growth hormone-releasing peptides. A hexapeptide, His-D-Trp-Ala-Trp-D-Phe-Lys-amide (GHRP-6) (SEQ ID NO:145), was found to release growth hormone from somatotrops in a dose-dependent manner in several species, including man (Bowers et al., *Endocrinology* 1984, 114, 1537-1545). Subsequent chemical studies on GHRP-6 led to the identification of other potent growth-hormone secretagogues such as GHRP-I, GHRP-2 and hexarelin (Cheng et al., *Endocrinology* 1989, 124, 2791-2798, Bowers, C. Y. Novel GH-Releasing Peptides, in *Molecular and Clinical Advances in Pituitary Disorders*, Ed: Melmed, S.; Endocrine Research and Education, Inc., Los Angeles, Calif., USA 1993, 153-157, and Deghenghi et al., *Life Sci.* 1994, 54, 1321-1328):

GHRP-I  Ala-His-D-(2')-Nal-Ala-Trp-D-Phe-Lys-NH$_2$ (SEQ ID NO:146),

GHRP-2  D-Ala-D-(2')-Nal-Ala-Trp-D-Nal-Lys-NH$_2$ (SEQ ID NO:147), hexarelin His-D-2-MeTrp-Ala-Trp-D-Phe-Lys-NH$_2$ (SEQ ID NO:148).

GHRP-I, GHRP-2, GHRP-6, and hexarelin are synthetic growth-hormone secretagogues. Growth-hormone secretagogues stimulate secretion of growth hormone by a mechanism different from that of growth hormone-releasing hormone (Bowers et al., *Endocrinology* 1984, 114, 1537-1545, Cheng et al., *Endocrinology* 1989, 124, 2791-2798, Bowers, C. Y. Novel GH-Releasing Peptides in *Molecular and Clinical Advances in Pituitary Disorders*. Ed: Melmed, S.; Endocrine Research and Education, Inc., Los Angeles, Calif., USA 1993, 153-157, and Deghenghi et al., *Life Sci.* 1994, 54, 1321-1328).

The low oral bioavailability (<1%) of the peptidyl growth-hormone secretagogues stimulated search for non-peptide compounds mimicking action of GHRP-6 in the pituitary. Several benzolactams and spiroindanes have been reported to stimulate growth-hormone release in various animal species and in man. (Smith et al., *Science* 1993, 260, 1640-1643, Patchett et al., *Proc. Natl. Acad. Sci. USA* 1995, 92, 7001-7005, and Chen et al., *Bioorg. Med. Chem. Lett.* 1996, 6, 2163-2169). A specific example of a small spiroindane is MK-0677 (Patchett et al., *Proc. Natl. Acad. Sci. USA* 1995, 92, 7001-7005):

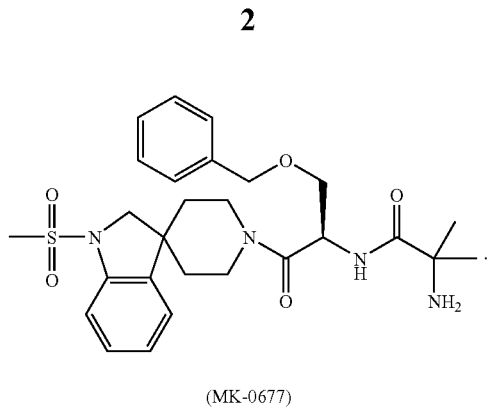

(MK-0677)

The actions of the above-mentioned growth-hormone secretagogues (both peptide and non-peptide) appear to be mediated by a specific growth-hormone secretagogue receptor (GHS receptor) (Howard et al., *Science* 1996, 273, 974-977, and Pong et al., *Molecular Endocrinology* 1996, 10, 57-61). This receptor is present in the pituitary and hypothalamus of various mammalian species (GHSR1a) and is distinct from the growth hormone-releasing hormone receptor. The GHS receptor was also detected in the other areas of the central nervous system and in peripheral tissues, for instance adrenal and thyroid glands, heart, lung, kidney and skeletal muscles (Chen et al., *Bioorg. Med. Chem. Lett.* 1996, 6, 2163-2169, Howard et al., *Science* 1996, 273, 974-977, Pong et al., *Molecular Endocrinology* 1996, 10, 57-61, Guan et al., *Mol. Brain. Res.* 1997, 48, 23-29, and McKee et al., *Genomics* 1997, 46, 426-434). A truncated version of GHSR1a has been reported (Howard et al., *Science* 1996, 273, 974-977).

The GHS receptor is a G-protein coupled-receptor. Effects of GHS receptor activation includes depolarization and inhibition of potassium channels, an increase in intercellular concentrations of inositol triphosphate (IP3), and a transient increase in the concentrations of intracellular calcium (Pong et al., *Molecular Endocrinology* 1996, 10, 57-61, Guan et al., *Mol. Brain. Res.* 1997, 48, 23-29, and McKee et al., *Genomics* 1997, 46, 426-434).

SUMMARY OF THE INVENTION

The present invention features ghrelin analogs active at the GHS receptor. Ghrelin is a naturally occurring peptide which is believed to be an endogenous ligand for the GHS receptor (Kojima et al., *Nature* 1999, 402, 656-660). The analogs of the invention can bind to the GHS receptor and, preferably, bring about signal transduction. Ghrelin analogs have a variety of different therapeutic uses as well as uses as research tools.

The native structures of ghrelins from several mammalian and non-mammalian species of animals are known. (Kaiya et al., *J. Biol. Chem.* 2001, 276, 40441-40448; International Patent Application PCT/JP00/04907 (WO 01/07475)). In addition to acylation by n-octanoic acid native ghrelin also has been observed to be acylated with n-decanoic acid (Kaiya et al., *J. Biol. Chem.* 2001, 276, 40441-40448).

A core region present in ghrelin was found to provide for activity at the GHS receptor. The core region comprises the four N-terminal amino acids, where the serine at position 3 is modified with n-octanoic acid.

Thus, a first aspect of the present invention describes a ghrelin analog according to formula (I):

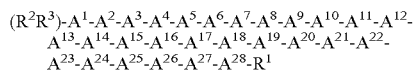

(I), or a pharmaceutically acceptable salt thereof, wherein:

$A^1$ is Gly, Aib, Ala, β-Ala, or Acc;

$A^2$ is Ser, Aib, Act, Ala, Acc, Abu, Act, Ava, Thr, or Val;

$A^3$ is Ser, Ser(C(O)—$R^4$), Asp(O—$R^8$), Asp(NH—$R^9$), Cys(S—$R^{14}$), Dap(S(O)$_2$—$R^{10}$), Dab(S(O)$_2$—$R^{11}$), Glu (O—$R^6$), Glu(NH—$R^7$), Thr, Thr(C(O)—$R^5$), or HN—CH ((CH$_2$)$_n$—N($R^{12}R^{13}$))—C(O);

$A^4$ is Phe, Acc, Aic, Cha, 2Fua, 1Nal, 2Nal, 2Pal, 3Pal, 4Pal, hPhe, ($X^1$, $X^2$, $X^3$, $X^4$, $X^5$)Phe, Taz, 2Thi, 3Thi, Trp, or Tyr;

$A^5$ is Leu, Abu, Acc, Aib, Ala, Cha, Ile, hLeu, Nle, Nva, Phe, Tle, or Val;

$A^6$ is Ser, Abu, Acc, Act, Aib, Ala, Gly, Thr, or Val;

$A^7$ is Pro, Dhp, Dmt, 3Hyp, 4Hyp, Inc, Ktp, Oic, Pip, Thz, Tic, or deleted;

$A^8$ is Glu, Acc, Aib, Arg, Asn, Asp, Dab, Dap, Gln, Lys, Orn, HN—CH((CH$_2$)$_n$—N($R^{12}R^{13}$))—C(O), or deleted;

$A^9$ is His, Apc, Aib, Acc, 2Fua, 2Pal, 3Pal, 4Pal, Taz, 2Thi, 3Thi, ($X^1$, $X^2$, $X^3$, $X^4$, $X^5$-)Phe or deleted;

$A^{10}$ is Gln, Acc, Aib, Asn, Asp, Glu, or deleted;

$A^{11}$ is Arg, Apc, hArg, Dab, Dap, Lys, Orn, HN—CH ((CH$_2$)$_n$—N($R^{12}R^{13}$))—C(O), or deleted;

$A^{12}$ is Val, Abu, Acc, Aib, Ala, Cha, Nva, Gly, Ile, Leu, Nle, Tle, Cha, or deleted;

$A^{13}$ is Gln, Acc, Aib, Asn, Asp, Glu, or deleted;

$A^{14}$ is Gln, Acc, Aib, Asn, Asp, Glu, or deleted;

$A^{15}$ is Arg, hArg, Acc, Aib, Apc, Dab, Dap, Lys, Orn, HN—CH((CH$_2$)$_n$—N($R^{12}R^{13}$))—C(O), or deleted;

$A^{16}$ is Lys, Acc, Aib, Apc, Arg, hArg, Dab, Dap, Orn, HN—CH((CH$_2$)$_n$—N($R^{12}R^{13}$))—C(O), or deleted;

$A^{17}$ is Glu, Arg, Asn, Asp, Dab, Dap, Gln, Lys, Orn, HN—CH((CH$_2$)$_n$—N($R^{12}R^{13}$))—C(O), or deleted;

$A^{18}$ is Ser, Abu, Acc, Act, Aib, Ala, Thr, Val, or deleted;

$A^{19}$ is Lys, Acc, Aib, Apc, Arg, hArg, Dab, Dap, Orn, HN—CH((CH$_2$)$_n$—N($R^{12}R^{13}$))—C(O), or deleted;

$A^{20}$ is Lys, Acc, Aib, Apc, Arg, hArg, Dab, Dap, Orn, HN—CH((CH$_2$)$_n$—N($R^{12}R^{13}$))—C(O), or deleted;

$A^{21}$ is Pro, Dhp, Dmt, Inc, 3Hyp, 4Hyp, Ktp, Oic, Pip, Thz, Tic, or deleted;

$A^{22}$ is Pro, Dhp, Dmt, 3Hyp, 4Hyp, Inc, Ktp, Oic, Pip, Thz, Tic, or deleted;

$A^{23}$ is Abu, Acc, Act, Aib, Ala, Apc, Gly, Nva, Val, or deleted;

$A^{24}$ is Lys, Acc, Aib, Apc, Arg, hArg, Dab, Dap, Orn, HN—CH((CH$_2$)$_n$—N($R^{12}R^{13}$))—C(O), or deleted;

$A^{25}$ is Leu, Abu, Acc, Aib, Ala, Cha, Ile, hLeu, Nle, Nva, Phe, Tle, Val, or deleted;

$A^{26}$ is Gln, Aib, Asn, Asp, Glu, or deleted;

$A^{27}$ is Pro, Dhp, Dmt, 3Hyp, 4Hyp, Inc, Ktp, Oic, Pip, Thz, Tic, or deleted;

$A^{28}$ is Acc, Aib, Apc, Arg, hArg, Dab, Dap, Lys, Orn, HN—CH((CH$_2$)$_n$—N($R^{12}R^{13}$))—C(O), or deleted;

$R^1$ is —OH, —NH$_2$, —(C$_1$-C$_{30}$)alkoxy, or NH—$X^6$— CH$_2$-Z$^0$, wherein $X^6$ is a (C$_1$-C$_{12}$)alkyl, (C$_2$-C$_{12}$)alkenyl, and $Z^0$ is —H, —OH, —CO$_2$H or —C(O)—NH$_2$;

$R^2$ and $R^3$ each is, independently for each occurrence, H, (C$_1$-C$_{20}$)alkyl or (C$_1$-C$_{20}$)acyl;

$R^4$, $R^5$, $R^6$, $R^7$, $R^8$, $R^9$, $R^{10}$, $R^{11}$ and $R^{14}$ each is, independently for each occurrence, (C$_1$-C$_{40}$)alkyl, (C$_2$-C$_{40}$)alkenyl, substituted (C$_1$-C$_{40}$) alkyl, substituted (C$_2$-C$_{40}$) alkenyl, alkylaryl, substituted alkylaryl, aryl or substituted aryl;

$R^{12}$ and $R^{13}$ each is, independently for each occurrence, H, (C$_1$-C$_{40}$)alkyl, (C$_1$-C$_{40}$)acyl, (C$_1$-C$_{30}$)alkylsulfonyl, or —C(NH)—NH$_2$, wherein when $R^{12}$ is (C$_1$-C$_{40}$)acyl, (C$_1$-C$_{30}$)alkylsulfonyl, or —C(NH)—NH$_2$, then $R^{13}$ is H or (C$_1$-C$_{40}$)alkyl;

n is, independently for each occurrence, 1, 2, 3, 4, or 5;

$X^1$, $X^2$, $X^3$, $X^4$, and $X^1$ each is, independently for each occurrence, H, F, Cl, Br, I, (C$_{1-10}$)alkyl, substituted (C$_{1-10}$) alkyl, aryl, substituted aryl, OH, NH$_2$, NO$_2$, or CN;

provided that the peptide contains at least one amino acid selected from the groups consisting of:

$A^2$ is Aib, Acc, or Act;

$A^3$ is Dap(S(O)$_2$—$R^{10}$), Dab(S(O)$_2$—$R^{11}$), Glu(NH-Hexyl), or Cys(S-Decyl);

$A^5$ is Abu, Acc, Aib, Ala, Cha, Ile, hLeu, Nle, Nva, Phe, Tle, or Val;

$A^6$ is Abu, Acc, Act, Aib, Ala, Gly, Thr or Val;

$A^7$ is Dhp, Dmt, 3Hyp, 4Hyp, Inc, Ktp, Oic, Pip, Thz or Tic;

$A^8$ is Acc, Aib, Arg, Asn, Asp, Dab, Dap, Gln, Lys, Orn, or HN—CH((CH$_2$)$_n$—N($R^{12}R^{13}$))—C(O);

$A^9$ is Aib, Acc, Apc, 2Fua, 2Pal, 3Pal, 4Pal, Taz, 2Thi, 3Thi, or ($X^1$, $X^2$, $X^3$, $X^4$, $X^5$-)Phe; and $A^{10}$ is Acc, Aib, Asn, Asp, or Glu;

and further provided that the peptide is not (Lys$^8$)hGhrelin (1-8)-NH$_2$ or (Arg$^8$)hGhrelin(1-8)-NH$_2$.

A preferred group of compounds of formula (I), termed Group 1 compounds, is where:

$A^1$ is Gly or Aib;

$A^2$ is Ser, Aib, A5c, Act, or Ava;

$A^3$ is Ser(C(O)—$R^4$), Glu(O—$R^6$), Glu(NH—$R^7$), Dap(S (O)$_2$—$R^{10}$), or Dab(S(O)$_2$—$R^{11}$);

$A^4$ is Phe;

$A^5$ is Leu, Acc, Aib, Cha, or hLeu;

$A^6$ is Ser, Abu, Act, Aib, or Thr;

$A^7$ is Pro, Dhp, Dmt, 4Hyp, Ktp, Pip, Tic, or Thz;

$A^8$ is Glu or Aib;

$A^9$ is His, Aib, Apc, 2Fua, 2Pal, 3Pal, 4Pal, Taz, or 2Thi;

$A^{10}$ is Gln or Aib;

$A^{11}$ is Arg;

$A^{12}$ is Aib, Val or Acc;

$A^{13}$ is Gln;

$A^{14}$ is Gln;

$A^{15}$ is Arg or Orn;

$A^{16}$ is Lys or Apc;

$A^{17}$ is Glu;

$A^{18}$ is Ser;

$A^{19}$ is Lys;

$A^{20}$ is Lys;

$A^{21}$ is Pro;

$A^{22}$ is Pro;

$A^{23}$ is Ala;

$A^{24}$ is Lys;

$A^{25}$ is Leu;

$A^{26}$ is Gln;

$A^{27}$ is Pro; and $A^{28}$ is Arg, or a pharmaceutically acceptable salt thereof.

A more preferred group of compounds of formula (I), termed Group 2 compounds, is where:

$R^2$ and $R^3$ each is, independently, H, Acyl, n-butyryl, isobutyryl, or n-octanoyl;

$R^4$ is octyl;

$R^6$ is hexyl;

$R^7$ is hexyl;

$R^{10}$ is octyl; and $R^{11}$ is octyl, or a pharmaceutically acceptable salt thereof, wherein Acc is, independently for each occurrence, A5c or A6c.

A more preferred compound according to formula (I), termed a Group 3 compound, is a compound according to the formula:

(Dap$^3$(Octanesulfonyl))hGhrelin(1-28)-NH$_2$; (SEQ ID NO:1)
(Aib$^2$, A6c$^5$)hGhrelin(1-28)-NH$_2$; (SEQ ID NO:2)
(A6c$^5$)hGhrelin(1-28)-NH$_2$; (SEQ ID NO:3)
(Aib$^{2,6}$)hGhrelin(1-28)-NH$_2$; (SEQ ID NO:4)
(Aib$^2$, A5c$^{12}$)hGhrelin(1-28)-NH$_2$; (SEQ ID NO:5)
(Aib$^2$, A5c$^{12}$, Orn$^{15}$)hGhrelin(1-28)-NH$_2$; (SEQ ID NO:6)
(Aib$^2$, A5c$^{12}$, Apc$^{16}$)hGhrelin(1-28)-NH$_2$; (SEQ ID NO:7)
(Aib$^2$, Act$^6$)hGhrelin(1-28)-NH$_2$; (SEQ ID NO:4)
(Aib$^2$, 3Pal$^9$)hGhrelin(1-28)-NH$_2$; (SEQ ID NO:8)
(Aib$^2$, Dmt$^7$)hGhrelin(1-28)-NH$_2$; (SEQ ID NO:9)
(Aib$^2$, Thz$^7$)hGhrelin(1-28)-NH$_2$; (SEQ ID NO:9)
(A5c$^2$)hGhrelin(1-28)-NH$_2$; (SEQ ID NO:10)
(Act$^2$)hGhrelin(1-28)-NH$_2$; (SEQ ID NO:10)
(Aib$^2$, A5c$^5$)hGhrelin(1-28)-NH$_2$; (SEQ ID NO:2)
(Aib$^2$, A6c$^5$)hGhrelin(1-28)-NH$_2$; (SEQ ID NO:2)
(Aib$^{2,5}$)hGhrelin(1-28)-NH$_2$; (SEQ ID NO:2)
(Aib$^2$, hLeu$^5$)hGhrelin(1-28)-NH$_2$; (SEQ ID NO:2)
(Aib$^2$, Cha$^5$)hGhrelin(1-28)-NH$_2$; (SEQ ID NO:2)
(Aib$^{2,6}$)hGhrelin(1-28)-NH$_2$; (SEQ ID NO:4)
(Aib$^2$, Act$^6$)hGhrelin(1-28)-NH$_2$; (SEQ ID NO:4)
(Aib$^2$, Thr$^6$)hGhrelin(1-28)-NH$_2$; (SEQ ID NO:4)
(Aib$^2$, Abu$^6$)hGhrelin(1-28)-NH$_2$; (SEQ ID NO:4)
(Aib$^2$, 4Hyp$^7$)hGhrelin(1-28)-NH$_2$; (SEQ ID NO:9)
(Aib$^2$, Thz$^7$)hGhrelin(1-28)-NH$_2$; (SEQ ID NO:9)
(Aib$^2$, Pip$^7$)hGhrelin(1-28)-NH$_2$; (SEQ ID NO:9)
(Aib$^2$, Dhp$^7$)hGhrelin(1-28)-NH$_2$; (SEQ ID NO:9)
(Aib$^2$, Ktp$^7$)hGhrelin(1-28)-NH$_2$; (SEQ ID NO:9)
(Aib$^{2,8}$)hGhrelin(1-28)-NH$_2$; (SEQ ID NO:11)
(Aib$^2$, 2Pal$^9$)hGhrelin(1-28)-NH$_2$; (SEQ ID NO:8)
(Aib$^2$, 3Pal$^9$)hGhrelin(1-28)-NH$_2$; (SEQ ID NO:8)
(Aib$^2$, 4Pal$^9$)hGhrelin(1-28)-NH$_2$; (SEQ ID NO:8)
(Aib$^2$, Taz$^9$)hGhrelin(1-28)-NH$_2$; (SEQ ID NO:8)
(Aib$^2$, 2Thi$^9$)hGhrelin(1-28)-NH$_2$; (SEQ ID NO:8)
(Aib$^2$, 2Fua$^9$)hGhrelin(1-28)-NH$_2$; (SEQ ID NO:8)
(Aib$^2$, Apc$^9$)hGhrelin(1-28)-NH$_2$; (SEQ ID NO:8)
(Aib$^{2,9}$)hGhrelin(1-28)-NH$_2$; (SEQ ID NO:8)
(Aib$^{2,10}$)hGhrelin(1-28)-NH$_2$; (SEQ ID NO:12)
(Aib$^2$, Tic$^7$)hGhrelin(1-28)-NH$_2$; (SEQ ID NO:9)
(Aib$^6$)hGhrelin(1-28)-NH$_2$; (SEQ ID NO:13)
(A5c$^5$)hGhrelin(1-28)-NH$_2$; (SEQ ID NO:3)
(A6c$^5$)hGhrelin(1-28)-NH$_2$; (SEQ ID NO:3)
(Act$^6$)hGhrelin(1-28)-NH$_2$; (SEQ ID NO:13)
(3Pal$^9$)hGhrelin(1-28)-NH$_2$; (SEQ ID NO:14)
(Dmt$^7$)hGhrelin(1-28)-NH$_2$; (SEQ ID NO:15)
(Thz$^7$)hGhrelin(1-28)-NH$_2$; (SEQ ID NO:15)
(Aib$^5$)hGhrelin(1-28)-NH$_2$; (SEQ ID NO:3)
(hLeu$^5$)hGhrelin(1-28)-NH$_2$; (SEQ ID NO:3)
(Cha$^5$)hGhrelin(1-28)-NH$_2$; (SEQ ID NO:3)
(Thr$^6$)hGhrelin(1-28)-NH$_2$; (SEQ ID NO:13)
(Abu$^6$)hGhrelin(1-28)-NH$_2$; (SEQ ID NO:13)
(4Hyp$^7$)hGhrelin(1-28)-NH$_2$; (SEQ ID NO:15)
(Pip$^7$)hGhrelin(1-28)-NH$_2$; (SEQ ID NO:15)
(Dhp$^7$)hGhrelin(1-28)-NH$_2$; (SEQ ID NO:15)
(Ktp$^7$)hGhrelin(1-28)-NH$_2$; (SEQ ID NO:15)
(Aib$^8$)hGhrelin(1-28)-NH$_2$; (SEQ ID NO:16)
(2Pal$^9$)hGhrelin(1-28)-NH$_2$; (SEQ ID NO:14)
(3Pal$^9$)hGhrelin(1-28)-NH$_2$; (SEQ ID NO:14)
(4Pal$^9$)hGhrelin(1-28)-NH$_2$; (SEQ ID NO:14)
(Taz$^9$)hGhrelin(1-28)-NH$_2$; (SEQ ID NO:14)
(2Thi$^9$)hGhrelin(1-28)-NH$_2$; (SEQ ID NO:14)
(2Fua$^9$)hGhrelin(1-28)-NH$_2$; (SEQ ID NO:14)
(Apc$^9$)hGhrelin(1-28)-NH$_2$; (SEQ ID NO:14)
(Aib$^9$)hGhrelin(1-28)-NH$_2$; (SEQ ID NO:14)
(Aib$^{10}$)hGhrelin(1-28)-NH$_2$; (SEQ ID NO:17)
(Aib$^2$, Dap$^3$(Octanesulfonyl), A6c$^5$)hGhrelin(1-28)-NH$_2$; (SEQ ID NO:18)
(Dap$^3$(Octanesulfonyl), A6c$^5$)hGhrelin(1-28)-NH$_2$; (SEQ ID NO:19)
(Aib$^{2,6}$, Dap$^3$(Octanesulfonyl))hGhrelin(1-28)-NH$_2$; (SEQ ID NO:20)
(Aib$^2$, Dap$^3$(Octanesulfonyl), A5c$^{12}$)hGhrelin(1-28)-NH$_2$; (SEQ ID NO:21)
(Aib$^2$, Dap$^3$(Octanesulfonyl), A5c$^{12}$)hGhrelin(1-28)-NH$_2$; (SEQ ID NO:22)
(Aib$^2$, Dap$^3$(Octanesulfonyl), A5c$^{12}$, Apc$^{16}$)hGhrelin(1-28)-NH$_2$; (SEQ ID NO:23)
(Aib$^2$, Dap$^3$(Octanesulfonyl), Act$^6$)hGhrelin(1-28)-NH$_2$; (SEQ ID NO:20)
(Aib$^2$, Dap$^3$(Octanesulfonyl), 3Pal$^9$)hGhrelin(1-28)-NH$_2$; (SEQ ID NO:24)
(Aib$^2$, Dap$^3$(Octanesulfonyl), Dmt$^7$)hGhrelin(1-28)-NH$_2$; (SEQ ID NO:25)
(Aib$^2$, Dap$^3$(Octanesulfonyl), Thz$^7$)hGhrelin(1-28)-NH$_2$; (SEQ ID NO:25)
(A5c$^2$, Dap$^3$(Octanesulfonyl))hGhrelin(1-28)-NH$_2$; (SEQ ID NO:26)
(Act$^2$, Dap$^3$(Octanesulfonyl))hGhrelin(1-28)-NH$_2$; (SEQ ID NO:26)
(Aib$^2$, Dap$^3$(Octanesulfonyl), A5c$^5$)hGhrelin(1-28)-NH$_2$; (SEQ ID NO:27)
(Aib$^{2,5}$, Dap$^3$(Octanesulfonyl))hGhrelin(1-28)-NH$_2$; (SEQ ID NO:27)
(Aib$^2$, Dap$^3$(Octanesulfonyl), hLeu$^5$)hGhrelin(1-28)-NH$_2$; (SEQ ID NO:27)
(Aib$^2$, Dap$^3$(Octanesulfonyl), Cha$^5$)hGhrelin(1-28)-NH$_2$; (SEQ ID NO:27)
(Aib$^{2,6}$, Dap$^3$(Octanesulfonyl))hGhrelin(1-28)-NH$_2$; (SEQ ID NO:20)
(Aib$^2$, Dap$^3$(Octanesulfonyl), Thr$^6$)hGhrelin(1-28)-NH$_2$; (SEQ ID NO:20)
(Aib$^2$, Dap$^3$(Octanesulfonyl), Abu$^6$)hGhrelin(1-28)-NH$_2$; (SEQ ID NO:20)
(Aib$^2$, Dap$^3$(Octanesulfonyl), 4Hyp$^7$)hGhrelin(1-28)-NH$_2$; (SEQ ID NO:25)
(Aib$^2$, Dap$^3$(Octanesulfonyl), Pip$^7$)hGhrelin(1-28)-NH$_2$; (SEQ ID NO:25)
(Aib$^2$, Dap$^3$(Octanesulfonyl), Dhp$^7$)hGhrelin(1-28)-NH$_2$; (SEQ ID NO:25)
(Aib$^2$, Dap$^3$(Octanesulfonyl), Ktp$^7$)hGhrelin(1-28)-NH$_2$; (SEQ ID NO:25)
(Aib$^{2,8}$, Dap$^3$(Octanesulfonyl))hGhrelin(1-28)-NH$_2$; (SEQ ID NO:28)
(Aib$^2$, Dap$^3$(Octanesulfonyl), 2Pal$^9$)hGhrelin(1-28)-NH$_2$; (SEQ ID NO:24)
(Aib$^2$, Dap$^3$(Octanesulfonyl), 3Pal$^9$)hGhrelin(1-28)-NH$_2$; (SEQ ID NO:24)
(Aib$^2$, Dap$^3$(Octanesulfonyl), 4Pal$^9$)hGhrelin(1-28)-NH$_2$; (SEQ ID NO:24)
(Aib$^2$, Dap$^3$(Octanesulfonyl), Taz$^9$)hGhrelin(1-28)-NH$_2$; (SEQ ID NO:24)
(Aib$^2$, Dap$^3$(Octanesulfonyl), Taz$^9$)hGhrelin(1-28)-NH$_2$; (SEQ ID NO:24)
(Aib$^2$, Dap$^3$(Octanesulfonyl), 2Thi$^9$)hGhrelin(1-28)-NH$_2$; (SEQ ID NO:24)
(Aib$^2$, Dap$^3$(Octanesulfonyl), 2Fua$^9$)hGhrelin(1-28)-NH$_2$; (SEQ ID NO:24)
(Aib$^2$, Dap$^3$(Octanesulfonyl), Apc$^9$)hGhrelin(1-28)-NH$_2$; (SEQ ID NO:24)
(Aib$^{2,9}$, Dap$^3$(Octanesulfonyl))hGhrelin(1-28)-NH$_2$; (SEQ ID NO:24)

(Aib²,¹⁰, Dap³ (Octanesulfonyl))hGhrelin(1-28)-NH₂; (SEQ ID NO:29)
(Dap³(Octanesulfonyl), A6c⁵)hGhrelin(1-28)-NH₂; (SEQ ID NO:19)
(Dap³(Octanesulfonyl), Aib⁶)hGhrelin(1-28)-NH₂; (SEQ ID NO:30)
(Dap³(Octanesulfonyl), A5c¹²)hGhrelin(1-28)-NH₂; (SEQ ID NO:31)
(Dap³(Octanesulfonyl), A5c¹², Orn¹⁵)hGhrelin(1-28)-NH₂; (SEQ ID NO:32)
(Dap³(Octanesulfonyl), A5c¹², Apc¹⁶)hGhrelin(1-28)-NH₂; (SEQ ID NO:33)
(Dap³(Octanesulfonyl), Act⁶)hGhrelin(1-28)-NH₂; (SEQ ID NO:30)
(Dap³(Octanesulfonyl), 3Pal⁹)hGhrelin(1-28)-NH₂; (SEQ ID NO:34)
(Dap³(Octanesulfonyl), Dmt⁷)hGhrelin(1-28)-NH₂; (SEQ ID NO:35)
(Dap³(Octanesulfonyl), Thz⁷)hGhrelin(1-28)-NH₂; (SEQ ID NO:35)
(Dap³(Octanesulfonyl), A5c⁵)hGhrelin(1-28)-NH₂; (SEQ ID NO:19)
(Dap³(Octanesulfonyl), Aib⁵)hGhrelin(1-28)-NH₂; (SEQ ID NO:19)
(Dap³(Octanesulfonyl), hLeu⁵)hGhrelin(1-28)-NH₂; (SEQ ID NO:19)
(Dap³(Octanesulfonyl), Cha⁵)hGhrelin(1-28)-NH₂; (SEQ ID NO:19)
(Dap³(Octanesulfonyl), Thr⁶)hGhrelin(1-28)-NH₂; (SEQ ID NO:30)
(Dap³(Octanesulfonyl), Abu⁶)hGhrelin(1-28)-NH₂; (SEQ ID NO:30)
(Dap³(Octanesulfonyl), 4Hyp⁷)hGhrelin(1-28)-NH₂; (SEQ ID NO:35)
(Dap³(Octanesulfonyl), Pip⁷)hGhrelin(1-28)-NH₂; (SEQ ID NO:35)
(Dap³(Octanesulfonyl), Dhp⁷)hGhrelin(1-28)-NH₂; (SEQ ID NO:35)
(Dap³(Octanesulfonyl), Ktp⁷)hGhrelin(1-28)-NH₂; (SEQ ID NO:35)
(Dap³(Octanesulfonyl), Aib⁸)hGhrelin(1-28)-NH₂; (SEQ ID NO:36)
(Dap³(Octanesulfonyl), 2Pal⁹)hGhrelin(1-28)-NH₂; (SEQ ID NO:34)
(Dap³(Octanesulfonyl), 3Pal⁹)hGhrelin(1-28)-NH₂; (SEQ ID NO:34)
(Dap³(Octanesulfonyl), 4Pal⁹)hGhrelin(1-28)-NH₂; (SEQ ID NO:34)
(Dap³(Octanesulfonyl), Taz⁹)hGhrelin(1-28)-NH₂; (SEQ ID NO:34)
(Dap³(Octanesulfonyl), 2Thi⁹)hGhrelin(1-28)-NH₂; (SEQ ID NO:34)
(Dap³(Octanesulfonyl), 2Fua⁹)hGhrelin(1-28)-NH₂; (SEQ ID NO:34)
(Dap³(Octanesulfonyl), Apc⁹)hGhrelin(1-28)-NH₂; (SEQ ID NO:34)
(Dap³(Octanesulfonyl), Aib⁹)hGhrelin(1-28)-NH₂; (SEQ ID NO:34)
(Dap³ (Octanesulfonyl), Aib¹⁰)hGhrelin(1-28)-NH₂; (SEQ ID NO:37)
(Dap³(Octanesulfonyl), A5c¹², Orn¹⁵)hGhrelin(1-28)-NH₂; (SEQ ID NO:32)
(Dab³(Octanesulfonyl), A5c¹², Orn¹⁵)hGhrelin(1-28)-NH₂; (SEQ ID NO:32)
(Aib², A6c⁵, A5c¹², Orn¹⁵)hGhrelin(1-28)-NH₂; (SEQ ID NO:38)
(A6c⁵, A5c¹², Orn¹⁵)hGhrelin(1-28)-NH₂; (SEQ ID NO:39)
(Aib²,⁶, A5c¹², Orn¹⁵)hGhrelin(1-28)-NH₂; (SEQ ID NO:40)
(Aib², Act⁶, A5c¹², Orn¹⁵)hGhrelin(1-28)-NH₂; (SEQ ID NO:40)
(Aib², 3Pal⁹, A5c¹², Orn¹⁵)hGhrelin(1-28)-NH₂; (SEQ ID NO:41)
(Aib², Dmt⁷, A5c¹², Orn¹⁵)hGhrelin(1-28)-NH₂; (SEQ ID NO:42)
(Aib², Thz⁷, A5c¹², Orn¹⁵)hGhrelin(1-28)-NH₂; (SEQ ID NO:42)
(Aib², A5c¹², A5c¹², Orn¹⁵)hGhrelin(1-28)-NH₂; (SEQ ID NO:38)
(Aib², A5c¹², Orn¹⁵)hGhrelin(1-28)-NH₂; (SEQ ID NO:38)
(Aib², hLeu⁵, A5c¹², Orn¹⁵)hGhrelin(1-28)-NH₂; (SEQ ID NO:38)
(Aib², Cha⁵, A5c¹², Orn¹⁵)hGhrelin(1-28)-NH₂; (SEQ ID NO:38)
(Aib²,⁶, A5c¹², Orn¹⁵)hGhrelin(1-28)-NH₂; (SEQ ID NO:40)
(Aib², A5c¹², Orn¹⁵)hGhrelin(1-28)-NH₂; (SEQ ID NO:40)
(Aib², Abu⁶, A5c¹², Orn¹⁵)hGhrelin(1-28)-NH₂; (SEQ ID NO:40)
(Aib², 4Hyp⁷, A5c¹², Orn¹⁵)hGhrelin(1-28)-NH₂; (SEQ ID NO:42)
(Aib², Pip⁷, A5c¹², Orn¹⁵)hGhrelin(1-28)-NH₂; (SEQ ID NO:42)
(Aib², Dhp⁷, A5c¹², Orn¹⁵)hGhrelin(1-28)-NH₂; (SEQ ID NO:42)
(Aib², Ktp⁷, A5c¹², Orn¹⁵)hGhrelin(1-28)-NH₂; (SEQ ID NO:42)
(Aib²,⁸, A5c¹², Orn¹⁵)hGhrelin(1-28)-NH₂; (SEQ ID NO:43)
(Aib², 2Pal⁹, A5c¹², Orn¹⁵)hGhrelin(1-28)-NH₂; (SEQ ID NO:41)
(Aib², 3Pal⁹, A5c¹², Orn¹⁵)hGhrelin(1-28)-NH₂; (SEQ ID NO:41)
(Aib², 4Pal⁹, A5c¹², Orn¹⁵)hGhrelin(1-28)-NH₂; (SEQ ID NO:41)
(Aib², Taz⁹, A5c¹², Orn¹⁵)hGhrelin(1-28)-NH₂; (SEQ ID NO:41)
(Aib², 2Thi⁹, A5c¹², Orn¹⁵)hGhrelin(1-28)-NH₂; (SEQ ID NO:41)
(Aib², 2Fua⁹, A5c¹², Orn¹⁵)hGhrelin(1-28)-NH₂; (SEQ ID NO:41)
(Aib², Apc⁹, A5c¹², Orn¹⁵)hGhrelin(1-28)-NH₂; (SEQ ID NO:41)
(Aib²,⁹, A5c¹², Orn¹⁵)hGhrelin(1-28)-NH₂; (SEQ ID NO:41)
(Aib²,¹⁰, A5c¹², Orn¹⁵)hGhrelin(1-28)-NH₂; (SEQ ID NO:44)
(Dap³(Octanesulfonyl), A5c¹², Apc¹⁶)hGhrelin(1-28)-NH₂; (SEQ ID NO:33)
(Dab³(Octanesulfonyl), A5c¹², Apc¹⁶)hGhrelin(1-28)-NH₂; (SEQ ID NO:33)
(Aib², A6c⁵, A5c¹², Apc¹⁶)hGhrelin(1-28)-NH₂; (SEQ ID NO:45)
(A6c⁵, A5c¹², Apc¹⁶)hGhrelin(1-28)-NH₂; (SEQ ID NO:46)
(Aib²,⁶, A5c¹², Apc¹⁶)hGhrelin(1-28)-NH₂; (SEQ ID NO:47)
(Aib², Act⁶, A5c¹², Apc¹⁶)hGhrelin(1-28)-NH₂; (SEQ ID NO:47)

(Aib², 3Pal⁹, A5c¹², Apc¹⁶)hGhrelin(1-28)-NH₂; (SEQ ID NO:48)
(Aib², Dmt⁷, A5c¹², Apc¹⁶)hGhrelin(1-28)-NH₂; (SEQ ID NO:49)
(Aib², Thz⁷, A5c¹², Apc¹⁶)hGhrelin(1-28)-NH₂; (SEQ ID NO:49)
(Aib², A5c¹², Apc¹⁶)hGhrelin(1-28)-NH₂; (SEQ ID NO:45)
(Aib²,⁵, A5c¹², Apc¹⁶)hGhrelin(1-28)-NH₂; (SEQ ID NO:45)
(Aib², hLeu⁵, A5c¹², Apc¹⁶)hGhrelin(1-28)-NH₂; (SEQ ID NO:45)
(Aib², Cha⁵, A5c¹², Apc¹⁶)hGhrelin(1-28)-NH₂; (SEQ ID NO:45)
(Aib²,⁶, A5c¹², Apc¹⁶)hGhrelin(1-28)-NH₂; (SEQ ID NO:47)
(Aib², Thr⁶, A5c¹², Apc¹⁶)hGhrelin(1-28)-NH₂; (SEQ ID NO:47)
(Aib², Abu⁶, A5c¹², Apc¹⁶)hGhrelin(1-28)-NH₂; (SEQ ID NO:47)
(Aib², 4Hyp⁷, A5c¹², Apc¹⁶)hGhrelin(1-28)-NH₂; (SEQ ID NO:49)
(Aib², Pip⁷, A5c¹², Apc¹⁶)hGhrelin(1-28)-NH₂; (SEQ ID NO:49)
(Aib², Dhp⁷, A5c¹², Apc¹⁶)hGhrelin(1-28)-NH₂; (SEQ ID NO:49)
(Aib², Ktp⁷, A5c¹², Apc¹⁶)hGhrelin(1-28)-NH₂; (SEQ ID NO:49)
(Aib²,⁸, A5c¹², Apc¹⁶)hGhrelin(1-28)-NH₂; (SEQ ID NO:50)
(Aib², 2Pal⁹, A5c¹², Apc¹⁶)hGhrelin(1-28)-NH₂; (SEQ ID NO:48)
(Aib², 3Pal⁹, A5c¹², Apc¹⁶)hGhrelin(1-28)-NH₂; (SEQ ID NO:48)
(Aib², 4Pal⁹, A5c¹², Apc¹⁶)hGhrelin(1-28)-NH₂; (SEQ ID NO:48)
(Aib², Taz⁹, A5c¹², Apc¹⁶)hGhrelin(1-28)-NH₂; (SEQ ID NO:48)
(Aib², 2Thi⁹, A5c¹², Apc¹⁶)hGhrelin(1-28)-NH₂; (SEQ ID NO:48)
(Aib², 2Fua⁹, A5c¹², Apc¹⁶)hGhrelin(1-28)-NH₂; (SEQ ID NO:48)
(Aib², Apc⁹, A5c¹², Apc¹⁶)hGhrelin(1-28)-NH₂; (SEQ ID NO:48)
(Aib²,⁹, A5c¹², Apc¹⁶)hGhrelin(1-28)-NH₂; (SEQ ID NO:48)
(Aib²,¹⁰, A5c¹², Apc¹⁶)hGhrelin(1-28)-NH₂; (SEQ ID NO:51)
(A6c⁵, A5c¹², Orn¹⁵)hGhrelin((1-28)-NH₂; (SEQ ID NO:39)
(Aib⁶, A5c¹², Orn¹⁵)hGhrelin(1-28)-NH₂; (SEQ ID NO:52)
(Act⁶, A5c¹², Orn¹⁵)hGhrelin(1-28)-NH₂; (SEQ ID NO:52)
(3Pal⁹, A5c¹², Orn¹⁵)hGhrelin(1-28)-NH₂; (SEQ ID NO:53)
(Dmt⁷, A5c¹², Orn¹⁵)hGhrelin(1-28)-NH₂; (SEQ ID NO:54)
(Thz⁷, A5c¹², Orn¹⁵)hGhrelin(1-28)-NH₂; (SEQ ID NO:54)
(A5c⁵, A5c¹², Orn¹⁵)hGhrelin(1-28)-NH₂; (SEQ ID NO:39)
(Aib⁵, A5c¹², Orn¹⁵)hGhrelin(1-28)-NH₂; (SEQ ID NO:39)
(hLeu⁵, A5c¹², Orn¹⁵)hGhrelin(1-28)-NH₂; (SEQ ID NO:39)
(Cha⁵, A5c¹², Orn¹⁵)hGhrelin(1-28)-NH₂; (SEQ ID NO:39)
(Aib⁶, A5c¹², Orn¹⁵)hGhrelin(1-28)-NH₂; (SEQ ID NO:52)
(Thr⁶, A5c¹², Orn¹⁵)hGhrelin(1-28)-NH₂; (SEQ ID NO:52)
(Abu⁶, A5c¹², Orn¹⁵)hGhrelin(1-28)-NH₂; (SEQ ID NO:52)
(4Hyp⁷, A5c¹², Orn¹⁵)hGhrelin(1-28)-NH₂; (SEQ ID NO:54)
(Pip⁷, A5c¹², Orn¹⁵)hGhrelin(1-28)-NH₂; (SEQ ID NO:54)
(Dhp⁷, A5c¹², Orn¹⁵)hGhrelin(1-28)-NH₂; (SEQ ID NO:54)
(Ktp⁷, A5c¹², Orn¹⁵)hGhrelin(1-28)-NH₂; (SEQ ID NO:54)
(Aib⁸, A5c¹², Orn¹⁵)hGhrelin(1-28)-NH₂; (SEQ ID NO:55)
(2Pal⁹, A5c¹², Orn¹⁵)hGhrelin(1-28)-NH₂; (SEQ ID NO:53)
(3Pal⁹, A5c¹², Orn¹⁵)hGhrelin(1-28)-NH₂; (SEQ ID NO:53)
(4Pal⁹, A5c¹², Orn¹⁵)hGhrelin(1-28)-NH₂; (SEQ ID NO:53)
(Taz⁹, A5c¹², Orn¹⁵)hGhrelin(1-28)-NH₂; (SEQ ID NO:53)
(2Thi⁹, A5c¹², Orn¹⁵)hGhrelin(1-28)-NH₂; (SEQ ID NO:53)
(2Fua⁹, A5c¹², Orn¹⁵)hGhrelin(1-28)-NH₂; (SEQ ID NO:53)
(Apc⁹, A5c¹², Orn¹⁵)hGhrelin(1-28)-NH₂; (SEQ ID NO:53)
(Aib⁹, A5c¹², Orn¹⁵)hGhrelin(1-28)-NH₂; (SEQ ID NO:53)
(Aib¹⁰, A5c¹², Orn¹⁵)hGhrelin(1-28)-NH₂; (SEQ ID NO:56)
(Aib⁶, A5c¹², Apc¹⁶)hGhrelin(1-28)-NH₂; (SEQ ID NO:57)
(A5c⁵, A5c¹², Apc¹⁶)hGhrelin(1-28)-NH₂; (SEQ ID NO:46)
(Act⁶, A5c¹², Apc¹⁶)hGhrelin(1-28)-NH₂; (SEQ ID NO:57)
(3Pal⁹, A5c¹², Apc¹⁶)hGhrelin(1-28)-NH₂; (SEQ ID NO:58)
(Dmt⁷, A5c¹², Apc¹⁶)hGhrelin(1-28)-NH₂; (SEQ ID NO:59)
(Thz⁷, A5c¹², Apc¹⁶)hGhrelin(1-28)-NH₂; (SEQ ID NO:59)
(Aib⁵, A5c¹², Apc⁶)hGhrelin(1-28)-NH₂; (SEQ ID NO:46)
(hLeu⁵, A5c¹², Apc¹⁶)hGhrelin(1-28)-NH₂; (SEQ ID NO:46)
(Cha⁵, A5c¹², Apc¹⁶)hGhrelin(1-28)-NH₂; (SEQ ID NO:46)
(Thr⁶, A5c¹², Apc¹⁶)hGhrelin(1-28)-NH₂; (SEQ ID NO:57)
(Abu⁶, A5c¹², Apc⁶)hGhrelin(1-28)-NH₂; (SEQ ID NO:57)
(4Hyp⁷, A5c, Apc)hGhrelin(1-28)-NH₂; (SEQ ID NO:59)
(Pip⁷, A5c¹², Apc¹⁶)hGhrelin(1-28)-NH₂; (SEQ ID NO:59)
(Dhp⁷, A5c¹², Apc¹⁶)hGhrelin(1-28)-NH₂; (SEQ ID NO:59)
(Ktp⁷, A5c¹², Orn¹⁵)hGhrelin(1-28)-NH₂ (SEQ ID NO:59)
(Aib⁸, A5c¹², Apc¹⁶)hGhrelin(1-28)-NH₂; (SEQ ID NO:60)

(2Pal⁹, A5c¹², Apc⁶)hGhrelin(1-28)-NH₂; (SEQ ID NO:58)
(3Pal, A5c¹², Apc¹⁶)hGhrelin(1-28)-NH₂; (SEQ ID NO:58)
(4Pal⁹, A5c¹², Apc¹⁶)hGhrelin(1-28)-NH₂; (SEQ ID NO:58)
(Taz⁹, A5c¹², Apc¹⁶)hGhrelin(1-28)-NH₂; (SEQ ID NO:58)
(2Thi⁹, A5c¹², Apc¹⁶)hGhrelin(1-28)-NH₂; (SEQ ID NO:58)
(2Fua⁹, A5c¹², Apc¹⁶)hGhrelin(1-28)-NH₂; (SEQ ID NO:58)
(Apc⁹, A5c¹², Apc⁶)hGhrelin(1-28)-NH₂; (SEQ ID NO:58)
(Aib⁹, A5c¹², Apc¹⁶)hGhrelin(1-28)-NH₂; (SEQ ID NO:58)
(Aib⁹, A5c¹², Apc¹⁶)hGhrelin(1-28)-NH₂; (SEQ ID NO:61)
(Aib², Glu³(NH-Hexyl), A6c⁵)hGhrelin(1-28)-NH₂; (SEQ ID NO:62)
(Glu³(NH-Hexyl), A6c⁵)hGhrelin(1-28)-NH₂; (SEQ ID NO:63)
(Aib²,⁶, Glu³(NH-Hexyl))hGhrelin(1-28)-NH₂; (SEQ ID NO:64)
(Aib², Glu³(NH-Hexyl), Act⁶)hGhrelin(1-28)-NH₂; (SEQ ID NO:64)
(Aib², Glu³(NH-Hexyl), 3Pal⁹)hGhrelin(1-28)-NH₂; (SEQ ID NO:65)
(Aib², Glu³(NH-Hexyl), Dmt⁷)hGhrelin(1-28)-NH₂; (SEQ ID NO:66)
(Aib², Glu³(NH-Hexyl), Thz⁷)hGhrelin(1-28)-NH₂; (SEQ ID NO:66)
(Aib², Glu³(NH-Hexyl), A5c⁵)hGhrelin(1-28)-NH₂; (SEQ ID NO:62)
(Aib²,⁵, Glu³(NH-Hexyl))hGhrelin(1-28)-NH₂; (SEQ ID NO:62)
(Aib², Glu³(NH-Hexyl), hLeu⁵)hGhrelin(1-28)-NH₂; (SEQ ID NO:62)
(Aib², Cha⁵)hGhrelin(1-28)-NH₂; (SEQ ID NO:2)
(Aib²,⁶, Glu³(NH-Hexyl))hGhrelin(1-28)-NH₂; (SEQ ID NO:64)
(Aib², Glu³)(NH-Hexyl), Thr⁶)hGhrelin(1-28)-NH₂; (SEQ ID NO:64)
(Aib², Glu³(NH-Hexyl), Abu⁶)hGhrelin(1-28)-NH₂; (SEQ ID NO:64)
(Aib², Glu³(NH-Hexyl), 4Hyp⁷)hGhrelin(1-28)-NH₂; (SEQ ID NO:66)
(Aib², Glu³(NH-Hexyl), Pip⁷)hGhrelin(1-28)-NH₂; (SEQ ID NO:66)
(Aib², Glu³(NH-Hexyl), Dhp⁷)hGhrelin(1-28)-NH₂; (SEQ ID NO:66)
(Aib², Glu³(NH-Hexyl), Ktp⁷)hGhrelin(1-28)-NH₂; (SEQ ID NO:66)
(Aib²,⁸, Glu³(NH-Hexyl))hGhrelin(1-28)-NH₂; (SEQ ID NO:67)
(Aib², Glu³(NH-Hexyl), 2Pal⁹)hGhrelin(1-28)-NH₂; (SEQ ID NO:65)
(Aib², Glu³(NH-Hexyl), 3Pal⁹)hGhrelin(1-28)-NH₂; (SEQ ID NO:65)
(Aib², Glu³(NH-Hexyl), 4Pal⁹)hGhrelin(1-28)-NH₂; (SEQ ID NO:65)
(Aib², Glu³(NH-Hexyl), Taz⁹)hGhrelin(1-28)-NH₂; (SEQ ID NO:65)
(Aib², Glu³(NH-Hexyl), 2Thi⁹)hGhrelin(1-28)-NH₂; (SEQ ID NO:65)
(Aib², Glu³(NH-Hexyl), 2Fua⁹)hGhrelin(1-28)-NH₂; (SEQ ID NO:65)
(Aib², Glu³(NH-Hexyl), Apc⁹)hGhrelin(1-28)-NH₂; (SEQ ID NO:65)
(Aib²,⁹, Glu³(NH-Hexyl))hGhrelin(1-28)-NH₂; (SEQ ID NO:65)
(Aib²,¹⁰, Glu³(NH-Hexyl))hGhrelin(1-28)-NH₂; (SEQ ID NO:68)
(Glu³(NH-Hexyl), Aib⁶)hGhrelin(1-28)-NH₂; (SEQ ID NO:69)
(Glu³(NH-Hexyl), A5c⁵)hGhrelin(1-28)-NH₂; (SEQ ID NO:63)
(Glu³(NH-Hexyl), Act⁶)hGhrelin(1-28)-NH₂; (SEQ ID NO:69)
(Glu³(NH-Hexyl), 3Pal⁹)hGhrelin(1-28)-NH₂; (SEQ ID NO:70)
(Glu³(NH-Hexyl), Dmt⁷)hGhrelin(1-28)-NH₂; (SEQ ID NO:71)
(Glu³(NH-Hexyl), Thz⁷)hGhrelin(1-28)-NH₂; (SEQ ID NO:71)
(Glu³(NH-Hexyl), Aib⁵)hGhrelin(1-28)-NH₂; (SEQ ID NO:63)
(Glu³(NH-Hexyl), hLeu⁵)hGhrelin(1-28)-NH₂; (SEQ ID NO:63)
(Glu³(NH-Hexyl), Cha⁵)hGhrelin(1-28)-NH₂; (SEQ ID NO:63)
(Glu³(NH-Hexyl), Thr⁶)hGhrelin(1-28)-NH₂; (SEQ ID NO:69)
(Glu³(NH-Hexyl), Abu⁶)hGhrelin(1-28)-NH₂; (SEQ ID NO:69)
(Glu³(NH-Hexyl), 4Hyp⁷)hGhrelin(1-28)-NH₂; (SEQ ID NO:71)
(Glu³(NH-Hexyl), Pip⁷)hGhrelin(1-28)-NH₂; (SEQ ID NO:71)
(Glu³(NH-Hexyl), Dhp⁷)hGhrelin(1-28)-NH₂; (SEQ ID NO:71)
(Glu³(NH-Hexyl), Ktp⁷)hGhrelin(1-28)-NH₂; (SEQ ID NO:71)
(Glu³(NH-Hexyl), Aib⁸)hGhrelin(1-28)-NH₂; (SEQ ID NO:36)
(Glu³(NH-Hexyl), 2Pal⁹)hGhrelin(1-28)-NH₂; (SEQ ID NO:70)
(Glu³(NH-Hexyl), 3Pal⁹)hGhrelin(1-28)-NH₂; (SEQ ID NO:70)
(Glu³(NH-Hexyl), 4Pal⁹)hGhrelin(1-28)-NH₂; (SEQ ID NO:70)
(Glu³(NH-Hexyl), Taz⁹)hGhrelin(1-28)-NH₂; (SEQ ID NO:70)
(Glu³(NH-Hexyl), 2Thi⁹)hGhrelin(1-28)-NH₂; (SEQ ID NO:70)
(Glu³(NH-Hexyl), 2Fua⁹)hGhrelin(1-28)-NH₂; (SEQ ID NO:70)
(Glu³(NH-Hexyl), Apc⁹)hGhrelin(1-28)-NH₂; (SEQ ID NO:70)
(Glu³(NH-Hexyl), Aib⁹)hGhrelin(1-28)-NH₂; (SEQ ID NO:70)
(Glu³(NH-Hexyl), Aib¹⁰)hGhrelin(1-28)-NH₂; (SEQ ID NO:37)
(Aib², Glu³(NH-Hexyl), A6c⁵, A5c¹², Orn¹⁵)hGhrelin(1-28)-NH₂; (SEQ ID NO:72)
(A6c⁵, Glu³(NH-Hexyl), A5c¹², Orn¹⁵)hGhrelin(1-28)-NH₂; (SEQ ID NO:73)
(Aib²,⁶, Glu³(NH-Hexyl), A5c¹², Orn¹⁵)hGhrelin(1-28)-NH₂; (SEQ ID NO:74)
(Aib², Glu³(NH-Hexyl), Act⁶, A5c¹², Orn¹⁵)hGhrelin(1-28)-NH₂; (SEQ ID NO:74)
(Aib², Glu³(NH-Hexyl), 3Pal⁹, A5c¹², Orn¹⁵)hGhrelin(1-28)-NH₂; (SEQ ID NO:75)

(Aib², Glu³(NH-Hexyl), Dmt⁷, A5c¹², Orn¹⁵)hGhrelin(1-28)-NH₂; (SEQ ID NO:76)
(Aib², Glu³(NH-Hexyl), Thz⁷, A5c¹², Orn¹⁵)hGhrelin(1-28)-NH₂; (SEQ ID NO:76)
(Aib², Glu³(NH-Hexyl), A5c⁵, A5c¹², Orn¹⁵)hGhrelin(1-28)-NH₂; (SEQ ID NO:72)
(Aib²,⁵, Glu³(NH-Hexyl), A5c¹², Orn¹⁵)hGhrelin(1-28)-NH₂; (SEQ ID NO:72)
(Aib², hLeu⁵, A5c¹², Orn¹⁵)hGhrelin(1-28)-NH₂; (SEQ ID NO:38)
(Aib², Glu³(NH-Hexyl), Cha⁵, A5c¹², Orn¹⁵)hGhrelin(1-28)-NH₂; (SEQ ID NO:72)
(Aib²,⁶, Glu³ (NH-Hexyl), A5c¹², Orn¹⁵)hGhrelin(1-28)-NH₂; (SEQ ID NO:74)
(Aib², Glu³ (NH-Hexyl), Thr⁶, A5c¹², Orn¹⁵)hGhrelin(1-28)-NH₂; (SEQ ID NO:74)
(Aib², Glu³ (NH-Hexyl), Abu⁶, A5c¹², Orn¹⁵)hGhrelin(1-28)-NH₂; (SEQ ID NO:74)
(Aib², Glu³ (NH-Hexyl), 4Hyp⁷, A5c¹², Orn¹⁵)hGhrelin(1-28)-NH₂; (SEQ ID NO:76)
(Aib², Glu³(NH-Hexyl), Pip⁷, A5c¹², Orn¹⁵)hGhrelin(1-28)-NH₂; (SEQ ID NO:76)
(Aib², Glu³(NH-Hexyl), Dhp⁷, A5c¹², Orn¹⁵)hGhrelin(1-28)-NH₂; (SEQ ID NO:76)
(Aib², Glu³(NH-Hexyl), Ktp⁷, A5c¹², Orn¹⁵)hGhrelin(1-28)-NH₂; (SEQ ID NO:76)
(Aib²,⁸, Glu³(NH-Hexyl), A5c¹², Orn¹⁵)hGhrelin(1-28)-NH₂; (SEQ ID NO:77)
(Aib², Glu³ (NH-Hexyl), 2Pal⁹, A5c¹², Orn¹⁵)hGhrelin(1-28)-NH₂; (SEQ ID NO:75)
(Aib², Glu³ (NH-Hexyl), 3Pal⁹, A5c¹², Orn¹⁵)hGhrelin(1-28)-NH₂; (SEQ ID NO:75)
(Aib², Glu³ (NH-Hexyl), 4Pal⁹, A5c¹², Orn¹⁵)hGhrelin(1-28)-NH₂; (SEQ ID NO:75)
(Aib², Glu³ (NH-Hexyl), Taz⁹, A5c¹², Orn¹⁵)hGhrelin(1-28)-NH₂; (SEQ ID NO:75)
(Aib², Glu³ (NH-Hexyl), 2Thi⁹, A5c¹², Orn¹⁵)hGhrelin(1-28)-NH₂; (SEQ ID NO:75)
(Aib², Glu³(NH-Hexyl), 2Fua⁹, A5c¹², Orn¹⁵)hGhrelin(1-28)-NH₂; (SEQ ID NO:75)
(Aib², Glu³(NH-Hexyl), Apc⁹, A5c¹², Orn¹⁵)hGhrelin(1-28)-NH₂; (SEQ ID NO:75)
(Aib²,⁹, Glu³(NH-Hexyl), A5c¹², Orn¹⁵)hGhrelin(1-28)-NH₂; (SEQ ID NO:75)
(Aib²,¹², Glu³ (NH-Hexyl), 4Pal⁹, Orn¹⁵)hGhrelin(1-28)-NH₂; (SEQ ID NO:143)
(Aib²,¹⁰, Glu³(NH-Hexyl), A5c¹², Orn¹⁵)hGhrelin(1-28)-NH₂; (SEQ ID NO:78)
(Aib², Glu³(NH-Hexyl), A6c¹², A5c¹², Apc¹⁶)hGhrelin(1-28)-NH₂; (SEQ ID NO:79)
(Aib³Glu³(NH-Hexyl), A6c⁵, A5c¹², Apc¹⁶)hGhrelin(1-28)-NH₂; (SEQ ID NO:80)
(Aib²,⁶, Glu³(NH-Hexyl), A5c¹², Apc¹⁶)hGhrelin(1-28)-NH₂; (SEQ ID NO:81)
(Aib², Glu³(NH-Hexyl), Act⁶, A5c¹², Apc¹⁶)hGhrelin(1-28)-NH₂; (SEQ ID NO:81)
(Aib², Glu³(NH-Hexyl), 3Pal⁹, A5c¹², Apc¹⁶)hGhrelin(1-28)-NH₂; (SEQ ID NO:82)
(Aib², Glu³(NH-Hexyl), Dmt⁷, A5c¹², Apc¹⁶)hGhrelin(1-28)-NH₂; (SEQ ID NO:83)
(Aib², Glu³(NH-Hexyl), Thz⁷, A5c¹², Apc¹⁶)hGhrelin(1-28)-NH₂; (SEQ ID NO:83)
(Aib², Glu³(NH-Hexyl), A5c⁵,¹², Apc¹⁶)hGhrelin(1-28)-NH₂; (SEQ ID NO:79)
(Aib²,⁵, Glu³(NH-Hexyl), A5c¹², Apc¹⁶)hGhrelin(1-28)-NH₂; (SEQ ID NO:79)
(Aib², Glu³ (NH-Hexyl), hLeu⁵, A5c¹², Apc¹⁶)hGhrelin(1-28)-NH₂; (SEQ ID NO:79)
(Aib², Glu³(NH-Hexyl), Cha⁵, A5c¹², Apc¹⁶)hGhrelin(1-28)-NH₂; (SEQ ID NO:79)
(Aib²,⁶, Glu³(NH-Hexyl), A5c¹², Apc¹⁶)hGhrelin(1-28)-NH₂; (SEQ ID NO:81)
(Aib², Glu³(NH-Hexyl), Thr, A5c¹², Apc⁶)hGhrelin(1-28)-NH₂; (SEQ ID NO:81)
(Aib², Glu³(NH-Hexyl), Abu⁶, A5c¹², Apc¹⁶)hGhrelin(1-28)-NH₂; (SEQ ID NO:81)
(Aib², Glu³(NH-Hexyl), 4Hyp⁷, A5c¹², Apc¹⁶)hGhrelin(1-28)-NH₂; (SEQ ID NO:83)
(Aib², Glu³ (NH-Hexyl), Pip⁷, A5c¹², Apc¹⁶)hGhrelin(1-28)-NH₂; (SEQ ID NO:83)
(Aib², Glu³(NH-Hexyl), Dhp⁷, A5c¹², Apc¹⁶)hGhrelin(1-28)-NH₂; (SEQ ID NO:83)
(Aib², Glu³ (NH-Hexyl), Ktp⁷, A5c¹², Apc¹⁶)hGhrelin(1-28)-NH₂; (SEQ ID NO:83)
(Aib²,⁸, Glu³(NH-Hexyl), A5c¹², Apc¹⁶)hGhrelin(1-28)-NH₂; (SEQ ID NO:84)
(Aib², Glu³(NH-Hexyl), 2Pal⁹, A5c¹², Apc¹⁶)hGhrelin(1-28)-NH₂; (SEQ ID NO:82)
(Aib², Glu³(NH-Hexyl), 3Pal⁹, A5c¹², Apc¹⁶)hGhrelin(1-28)-NH₂; (SEQ ID NO:82)
(Aib², Glu³(NH-Hexyl), 4Pal⁹, A5c¹², Apc¹⁶)hGhrelin(1-28)-NH₂; (SEQ ID NO:82)
(Aib², Glu³(NH-Hexyl), Taz⁹, A5c¹², Apc¹⁶)hGhrelin(1-28)-NH₂; (SEQ ID NO:82)
(Aib², Glu³(NH-Hexyl), 2Thi⁹, A5c¹², Apc¹⁶)hGhrelin(1-28)-NH₂; (SEQ ID NO:82)
(Aib², Glu³(NH-Hexyl), 2Fua⁹, A5c¹², Apc¹⁶)hGhrelin(1-28)-NH₂; (SEQ ID NO:82)
(Aib², Glu³(NH-Hexyl), Apc⁹, A5c¹², Apc¹⁶)hGhrelin(1-28)-NH₂; (SEQ ID NO:82)
(Aib²,⁹, Glu³ (NH-Hexyl), A5c¹², Apc¹⁶)hGhrelin(1-28)-NH₂; (SEQ ID NO:82)
(Aib²,¹⁰, Glu³(NH-Hexyl), A5c¹², Apc¹⁶)hGhrelin(1-28)-NH₂; (SEQ ID NO:85)
(Glu³ (O-Hexyl))hGhrelin(1-28)-NH₂; (SEQ ID NO:86)
(Aib²)hGhrelin(1-28)-NH₂; (SEQ ID NO:10)
(Glu³(NH-Hexyl))hGhrelin(1-28)-NH₂; (SEQ ID NO:86)
(Aib², Glu³(O-Hexyl))hGhrelin(1-28)-NH₂; (SEQ ID NO:87)
(Aib¹, Glu³(O-Hexyl))hGhrelin(1-28)-NH₂; (SEQ ID NO:88)
(Aib², Glu³(NH-Hexyl))hGhrelin(1-28)-NH₂; (SEQ ID NO:87)
(Dap³(1-Octanesulfonyl))hGhrelin(1-28)-NH₂; (SEQ ID NO:1)
(Aib², Dap³(1-Octanesulfonyl))hGhrelin(1-28)-NH₂; (SEQ ID NO:89)
(Aib¹, Dap³(1-Octanesulfonyl))hGhrelin(1-28)-NH₂; (SEQ ID NO:88)
(Ava², Dap³(1-Octanesulfonyl))hGhrelin(2-28)-NH₂; (SEQ ID NO:144)
(Ac-Gly¹)hGhrelin(1-5)-NH₂; (SEQ ID NO:90)
(Ac-Gly¹)hGhrelin(1-6)-NH₂; (SEQ ID NO:91)
(Ac-Gly¹)hGhrelin(1-7)-NH₂; (SEQ ID NO:92)
(Ac-Gly¹, Aib²)hGhrelin(1-28)-NH₂; (SEQ ID NO:93)
(Ac-Gly¹, Aib², Glu³(NH-Hexyl))hGhrelin(1-5)-NH₂; (SEQ ID NO:94)
(Ac-Gly¹, Aib², Glu³(NH-Hexyl))hGhrelin(1-6)-NH₂; (SEQ ID NO:95)
(Ac-Gly¹, Aib², Glu³(NH-Hexyl))hGhrelin(1-7)-NH₂; (SEQ ID NO:96)
(Ac-Gly¹, Aib², Glu³(NH-Hexyl))hGhrelin(1-28)-NH₂; (SEQ ID NO:97)

(Ac-Gly$^1$, Aib$^2$, Glu$^3$(NH-Hexyl), Arg$^8$)hGhrelin(−8)-NH$_2$; (SEQ ID NO:98)
(Ac-Gly$^1$, Aib$^2$, Glu$^3$ (NH-Hexyl), Lys$^8$)hGhrelin(1-8)-NH$_2$; (SEQ ID NO:98)
(Ac-Gly$^1$, Aib$^{2,10}$, Glu$^3$(NH-Hexyl))hGhrelin(1-28)-NH$_2$; (SEQ ID NO:99)
(n-Butyryl-Gly$^1$)hGhrelin(1-28)-NH$_2$; (SEQ ID NO:100)
(n-Butyryl-Gly$^1$, Aib$^2$, Glu$^3$(NH-Hexyl))hGhrelin(1-28)-NH$_2$; (SEQ ID NO:101)
(Isobutyryl-Gly$^1$)hGhrelin(1-28)-NH$_2$; (SEQ ID NO:100) or
(n-Octanoyl-Gly$^1$)hGhrelin(1-28)-NH$_2$, (SEQ ID NO:100) or a pharmaceutically acceptable salt thereof.

A yet more preferred compound according to formula (I), termed a Group 4 compound, is a compound according to the formula:

(Thr$^6$)hGhrelin(1-28)-NH$_2$; (SEQ ID NO:102)
(4Hyp$^7$)hGhrelin(1-28)-NH$_2$; (SEQ ID NO:15)
(Aib$^8$)hGhrelin(1-28)-NH$_2$; (SEQ ID NO:16)
(Taz$^9$)hGhrelin(1-28)-NH$_2$; (SEQ ID NO:14)
(3Pal$^9$)hGhrelin(1-28)-NH$_2$; (SEQ ID NO:14)
(4Pal$^9$)hGhrelin(1-28)-NH$_2$; (SEQ ID NO:14)
(2Thi$^9$)hGhrelin(1-28)-NH$_2$; (SEQ ID NO:14)
(Aib$^2$, Glu$^3$(NH-Hexyl), Taz$^9$)hGhrelin(1-28)-NH$_2$; (SEQ ID NO:65)
(Aib$^2$, Glu$^3$(NH-Hexyl), Thr$^6$)hGhrelin(1-28)-NH$_2$; (SEQ ID NO:103)
(Aib$^2$, Glu$^3$(NH-Hexyl), 2Thi$^9$)hGhrelin(1-28)-NH$_2$; (SEQ ID NO:65)
(Aib$^2$, Thr$^6$)hGhrelin(1-28)-NH$_2$; (SEQ ID NO:104)
(Aib$^2$, 2Thi$^9$)hGhrelin(1-28)-NH$_2$; (SEQ ID NO:8)
(Asp$^3$(NH-heptyl))hGhrelin(1-28)-NH$_2$; (SEQ ID NO:105)
(Glu$^3$(NH-hexyl))hGhrelin(1-28)-NH$_2$; (SEQ ID NO:106)
(Aib$^1$)hGhrelin(1-28)-NH$_2$; (SEQ ID NO:107)
(Aib$^2$)hGhrelin(1-28)-NH$_2$; (SEQ ID NO:10)
(Glu$^3$(O-hexyl))hGhrelin(1-28)-NH$_2$; (SEQ ID NO:106)
(Asp$^3$(O-hexyl))hGhrelin(1-28)-NH$_2$; (SEQ ID NO:105)
Cys$^3$(S(CH$_2$)$_9$CH$_3$)hGhrelin(1-28)-NH$_2$; (SEQ ID NO:108)
(Aib$^2$, Glu$^3$(NH-hexyl))hGhrelin(1-28)-NH$_2$; (SEQ ID NO:109)
(Aib$^{2,6}$)hGhrelin(1-28)-NH$_2$; (SEQ ID NO:4)
(Aib$^2$,Act$^6$)hGhrelin(1-28)-NH$_2$; (SEQ ID NO:4)
(A5c$^5$)hGhrelin(1-28)-NH$_2$; (SEQ ID NO:10)
(Act$^2$)hGhrelin(1-28)-NH$_2$; (SEQ ID NO:10)
(Aib$^2$, A6c$^5$)hGhrelin(1-28)-NH$_2$; (SEQ ID NO:2)
(A6c$^5$)hGhrelin(1-28)-NH$_2$; (SEQ ID NO:3)
(Lys$^5$)hGhrelin(1-28)-NH$_2$; (SEQ ID NO:110)
(Aib$^2$, 3Pal$^9$)hGhrelin(1-28)-NH$_2$; (SEQ ID NO:8)
(Dap$^3$(Octanesulfonyl))hGhrelin(1-28)-NH$_2$; (SEQ ID NO:1)
(Aib$^2$,Thz$^7$)hGhrelin(1-28)-NH$_2$; (SEQ ID NO:9)
(Aib$^2$, Cha$^5$)hGhrelin(1-28)-NH$_2$; (SEQ ID NO:2)
(Aib$^2$, Abu$^6$)hGhrelin(1-28)-NH$_2$; (SEQ ID NO:4)
(Aib$^2$, 4Hyp$^7$)hGhrelin(1-28)-NH$_2$; (SEQ ID NO:9)
(Aib$^2$, Taz$^9$)hGhrelin(1-28)-NH$_2$; (SEQ ID NO:8)
(Aib$^2$, 4Pal$^9$)hGhrelin(1-28)-NH$_2$; (SEQ ID NO:8)
(Aib$^2$, Dhp$^7$)hGhrelin(1-28)-NH$_2$; (SEQ ID NO:9)
(Aib$^{2,8}$)hGhrelin(1-28)-NH$_2$; (SEQ ID NO:11)
(Aib$^2$, Pip$^7$)hGhrelin(1-28)-NH$_2$; (SEQ ID NO:9)
(Aib$^2$, Glu$^3$(NH-Hexyl), 4Hyp$^7$)hGhrelin(1-28)-NH$_2$; (SEQ ID NO:66)
(Aib$^{2,8}$, Glu$^3$(NH-Hexyl))hGhrelin(1-28)-NH$_2$; (SEQ ID NO:67)
(Aib$^{2,12}$, Glu$^3$(NH-Hexyl), 4Pal$^9$, Orn$^{15}$)hGhrelin(1-28)-NH$_2$; (SEQ ID NO:111)
(Aib$^2$, Glu$^3$(NH-Hexyl), 4Pal$^9$)hGhrelin(1-28)-NH$_2$; (SEQ ID NO:65)
(Aib$^2$, Glu$^3$(NH-Hexyl), 3Pal$^9$)hGhrelin(1-28)-NH$_2$; (SEQ ID NO:65)
(Aib$^{2,10}$)hGhrelin(1-28)-NH$_2$; (SEQ ID NO:12)
(Aib$^{2,10}$, Glu$^3$(NH-Hexyl))hGhrelin(1-28)-NH$_2$; (SEQ ID NO:68)
(Ac-Gly$^1$)hGhrelin(1-5)-NH$_2$; (SEQ ID NO:90)
(Ac-Gly$^1$)hGhrelin(1-6)-NH$_2$; (SEQ ID NO:91)
(Ac-Gly$^1$)hGhrelin(1-7)-NH$_2$; (SEQ ID NO:92)
(Ac-Gly$^1$, Aib$^2$)hGhrelin(1-28)-NH$_2$; (SEQ ID NO:93)
(Ac-Gly$^1$, Aib$^2$, Glu$^3$(NH-hexyl))hGhrelin(1-5)-NH$_2$; (SEQ ID NO:94)
(Ac-Gly$^1$, Aib$^2$, Glu$^3$(NH-hexyl))hGhrelin(1-6)-NH$_2$; (SEQ ID NO:95)
(Ac-Gly$^1$, Aib$^2$, Glu$^3$(NH-hexyl))hGhrelin(1-7)-NH$_2$; (SEQ ID NO:96)
(Ac-Gly$^1$, Aib$^2$, Glu$^3$(NH-hexyl))hGhrelin(1-28)-NH$_2$; (SEQ ID NO:97)
(Ac-Gly$^1$, Aib$^2$, Glu$^3$ (NH-hexyl), Arg$^8$)hGhrelin(1-8)-NH$_2$; (SEQ ID NO:98)
(Ac-Gly$^1$, Aib$^2$, Glu$^3$(NH-hexyl), Lys$^8$)hGhrelin(1-8)-NH$_2$; (SEQ ID NO:98)
(Ac-Gly$^1$, Aib$^{2,10}$, Glu$^3$(NH-Hexyl))hGhrelin(1-28)-NH$_2$; (SEQ ID NO:99)
(n-Butyryl-Gly$^1$)hGhrelin(1-28)-NH$_2$; (SEQ ID NO:100)
(n-Butyryl-Gly$^1$, Aib$^2$, Glu$^3$(NH-hexyl))hGhrelin(1-28)-NH$_2$; (SEQ ID NO:101)
(Isobutyryl-Gly$^1$)hGhrelin(1-28)-NH$_2$; (SEQ ID NO:100) or
(n-Octanoyl-Gly$^1$)hGhrelin(1-28)-NH$_2$, (SEQ ID NO:100) or a pharmaceutically acceptable salt thereof.

A still more preferred compound according to formula (I), termed a Group 5 compound, is a compound according to the formula:

(Aib$^2$, 3Pal$^9$)hGhrelin(1-28)-NH$_2$; (SEQ ID NO:8)
(Aib$^2$, 4Hyp$^7$)hGhrelin(1-28)-NH$_2$; (SEQ ID NO:9)
(Aib$^2$, Taz$^9$)hGhrelin(1-28)-NH$_2$; (SEQ ID NO:8)
(Aib$^2$, Dhp$^7$)hGhrelin(1-28)-NH$_2$; (SEQ ID NO:9)
(Aib$^{2,8}$)hGhrelin(1-28)-NH$_2$; (SEQ ID NO:11)
(Aib$^{2,8}$, Glu$^3$(NH-Hexyl))hGhrelin(1-28)-NH$_2$; (SEQ ID NO:112)
(Aib$^{2,10}$, Glu$^3$(NH-Hexyl))hGhrelin(1-28)-NH$_2$; (SEQ ID NO:113)
(Aib$^2$, Glu$^3$ (NH-hexyl))hGhrelin(1-28)-NH$_2$; (SEQ ID NO:114)
(Ac-Gly$^1$)hGhrelin(1-5)-NH$_2$; (SEQ ID NO:90)
(Ac-Gly$^1$)hGhrelin(1-6)-NH$_2$; (SEQ ID NO:91)
(Ac-Gly$^1$)hGhrelin(1-7)-NH$_2$; (SEQ ID NO:92)
(Ac-Gly$^1$, Aib$^2$)hGhrelin(1-28)-NH$_2$; (SEQ ID NO:93)
(Ac-Gly$^1$, Aib$^2$, Glu$^3$(NH-hexyl))hGhrelin(1-5)-NH$_2$; (SEQ ID NO:94)
(Ac-Gly$^1$, Aib$^2$, Glu$^3$(NH-hexyl))hGhrelin(1-6)-NH$_2$; (SEQ ID NO:95)
(Ac-Gly$^1$, Aib$^2$, Glu$^3$(NH-hexyl))hGhrelin(1-7)-NH$_2$; (SEQ ID NO:96)
(Ac-Gly$^1$, Aib$^2$, Glu$^3$(NH-hexyl))hGhrelin(1-28)-NH$_2$; (SEQ ID NO:97)
(Ac-Gly$^1$, Aib$^2$, Glu$^3$(NH-hexyl), Arg$^8$)hGhrelin(1-8)-NH$_2$; (SEQ ID NO:98)
(Ac-Gly$^1$, Aib$^2$, Glu$^3$(NH-hexyl), Lys$^8$)hGhrelin(1-8)-NH$_2$; (SEQ ID NO:98)
(Ac-Gly$^1$, Aib$^{2,10}$, Glu$^3$(NH-Hexyl))hGhrelin(1-28)-NH$_2$; (SEQ ID NO:99)
(n-Butyryl-Gly$^1$)hGhrelin(1-28)-NH$_2$; (SEQ ID NO:100)
(n-Butyryl-Gly$^1$, Aib$^2$, Glu$^3$(NH-hexyl))hGhrelin(1-28)-NH$_2$; (SEQ ID NO:101)

(Isobutyryl-Gly¹)hGhrelin(1-28)-NH₂; (SEQ ID NO:100) or
(n-Octanoyl-Gly¹)hGhrelin(1-28)-NH₂, (SEQ ID NO:100) or a
pharmaceutically acceptable salt thereof.

Another still more preferred compound according to formula (I), termed a Group 6 compound, is a compound according to the formula:
(Aib², 3Pal⁹)hGhrelin(1-28)-NH₂; (SEQ ID NO:8)
(Aib², 4Hyp⁷)hGhrelin(1-28)-NH₂; (SEQ ID NO:9)
(Aib², Taz⁹)hGhrelin(1-28)-NH₂; (SEQ ID NO:8)
(Aib², Dhp⁷)hGhrelin(1-28)-NH₂; (SEQ ID NO:9)
(Aib²,⁸)hGhrelin(1-28)-NH₂; (SEQ ID NO:11)
(Aib²,⁸, Glu³(NH-Hexyl))hGhrelin(1-28)-NH₂; (SEQ ID NO:115)
(Aib², Glu³(NH-hexyl))hGhrelin(1-28)-NH₂; (SEQ ID NO:114)
(Ac-Gly¹)hGhrelin(1-5)-NH₂; (SEQ ID NO:90)
(Ac-Gly¹)hGhrelin(1-6)-NH₂; (SEQ ID NO:91)
(Ac-Gly¹)hGhrelin(1-7)-NH₂; (SEQ ID NO:92)
(Ac-Gly¹, Aib²)hGhrelin(1-28)-NH₂; (SEQ ID NO:93)
(Ac-Gly¹, Aib², Glu³(NH-hexyl))hGhrelin(1-5)-NH₂; (SEQ ID NO:94)
(Ac-Gly¹, Aib², Glu³(NH-hexyl))hGhrelin(1-6)-NH₂; (SEQ ID NO:95)
(Ac-Gly¹, Aib², Glu³(NH-hexyl))hGhrelin(1-7)-NH₂; (SEQ ID NO:96)
(Ac-Gly¹, Aib², Glu³(NH-hexyl))hGhrelin(1-28)-NH₂; (SEQ ID NO:97)
(Ac-Gly¹, Aib², Glu³(NH-hexyl), Arg⁸)hGhrelin(1-8)-NH₂; (SEQ ID NO:98)
(Ac-Gly¹, Aib², Glu³(NH-hexyl), Lys⁸)hGhrelin(1-8)-NH₂; (SEQ ID NO:98)
(Ac-Gly¹, Aib²,¹⁰, Glu³(NH-hexyl))hGhrelin(1-28)-NH₂; (SEQ ID NO:99)
(n-Butyryl-Gly¹)hGhrelin(1-28)-NH₂; (SEQ ID NO:100)
(n-Butyryl-Gly¹, Aib², Glu³(NH-hexyl))hGhrelin(1-28)-NH₂; (SEQ ID NO:101)
(Isobutyryl-Gly¹)hGhrelin(1-28)-NH₂; (SEQ ID NO:100) or
(n-Octanoyl-Gly¹)hGhrelin(1-28)-NH₂, (SEQ ID NO:100) or a pharmaceutically acceptable salt thereof.

Another preferred compound according to formula (I), termed a Group 7 compound, is a compound according to the formula:
(Glu³(O-Hexyl))hGhrelin(1-28)-NH₂; (SEQ ID NO:106)
(Aib²)hGhrelin(1-28)-NH₂; (SEQ ID NO:10)
(Glu³(NH-Hexyl))hGhrelin(1-28)-NH₂; (SEQ ID NO:106) or
(Cys³(S-Decyl))hGhrelin(1-28)-NH₂, (SEQ ID NO:108) or a pharmaceutically acceptable salt thereof.

Still yet another preferred compound according to formula (I), termed a Group 8 compound, is a compound according to the formula:
(des-Ser²)hGhrelin(1-28)-NH₂; (SEQ ID NO:116) or
(des-Gly¹, des-Ser²)hGhrelin(1-28)-NH₂, (SEQ ID NO:116) or a pharmaceutically acceptable salt thereof.

Another preferred compound according to formula (I), termed a Group 9 compound, is a compound according to the formula:
(Aib¹, Ser³)hGhrelin(1-28)-NH₂; (SEQ ID NO:107)
(Aib², Ser³)hGhrelin(1-28)-NH₂; (SEQ ID NO:10)
(Aib²,⁶, Ser³)hGhrelin(1-28)-NH₂; (SEQ ID NO:4)
(A5c⁵, Ser³)hGhrelin(1-28)-NH₂; (SEQ ID NO:3)
(Aib², Ser³, 3Pal⁹)hGhrelin(1-28)-NH₂; (SEQ ID NO:8)
(Aib², Ser³, Thz⁷)hGhrelin(1-28)-NH₂; (SEQ ID NO:9)
(Aib², Ser³, Cha⁵)hGhrelin(1-28)-NH₂; (SEQ ID NO:2)
(Aib², Ser³, Abu⁶)hGhrelin(1-28)-NH₂; (SEQ ID NO:4)
(Aib², Ser³, 4Hyp⁷)hGhrelin(1-28)-NH₂; (SEQ ID NO:9)
(Aib², Ser³, Taz⁹)hGhrelin(1-28)-NH₂; (SEQ ID NO:8)
(Aib²,⁴, Ser³, 4Pal⁹)hGhrelin(1-28)-NH₂; (SEQ ID NO:117)
(Aib², Ser³, Dhp⁷)hGhrelin(1-28)-NH₂; (SEQ ID NO:9)
(Aib²,⁸, Ser³)hGhrelin(1-28)-N₂; (SEQ ID NO:112)
(Aib², Ser³, Pip⁷)hGhrelin(1-28)-NH₂; (SEQ ID NO:9)
(Ac-Gly¹, Aib²,¹⁰, Ser³)hGhrelin(1-28)-NH₂; (SEQ ID NO:118)
(Aib²,¹⁰, Ser³)hGhrelin(1-28)-NH₂; (SEQ ID NO:12)
(n-Octanoyl-Gly¹, Ser³)hGhrelin(1-28)-NH₂; (SEQ ID NO:100)
(Isobutyryl-Gly¹, Ser³)hGhrelin(1-28)-NH₂; (SEQ ID NO:100)
(n-Butyryl-Gly¹, Ser³)hGhrelin(1-28)-NH₂; (SEQ ID NO:100)
(n-Butyryl-Gly¹, Aib², Ser³)hGhrelin(1-28)-NH₂; (SEQ ID NO:119)
(Ac-Gly¹, Aib², Ser³)hGhrelin(1-28)-NH₂; (SEQ ID NO:93)
(Aib², Ser³, Tic⁷)hGhrelin(1-28)-NH₂; (SEQ ID NO:9)
(Ac-Gly¹, Aib², Ser³, Arg⁸)hGhrelin(1-8)-NH₂; (SEQ ID NO:120)
(Ser³, Aib⁸)hGhrelin(1-28)-NH₂; (SEQ ID NO:121)
(Ser³, Taz⁹)hGhrelin(1-28)-NH₂; (SEQ ID NO:14)
(Ser³,3Pal⁹)hGhrelin(1-28)-NH₂; (SEQ ID NO:14)
(Ser³, 4Pal⁹)hGhrelin(1-28)-NH₂; (SEQ ID NO:14)
(Aib², Ser³, 2Thi⁹)hGhrelin(1-28)-NH₂; (SEQ ID NO:8)
(Ser³, 2Thi⁹)hGhrelin(1-28)-N₂; (SEQ ID NO:14)
(Ser³, 4Hyp⁷)hGhrelin(1-28)-NH₂; (SEQ ID NO:15)
(Aib², Ser³, Tic⁷)hGhrelin(1-28)-NH₂; (SEQ ID NO:9)
(Aib¹, Thr³)hGhrelin(1-28)-NH₂; (SEQ ID NO:122)
(Aib², Thr³)hGhrelin(1-28)-NH₂; (SEQ ID NO:123)
(Aib²,⁶, Thr³)hGhrelin(1-28)-NH₂; (SEQ ID NO:124)
(A5c⁵, Thr³)hGhrelin(1-28)-NH₂; (SEQ ID NO:125)
(Aib², Thr³, 3Pal⁹)hGhrelin(1-28)-NH₂; (SEQ ID NO:126)
(Aib², Thr³, Thz⁷)hGhrelin(1-28)-NH₂; (SEQ ID NO:127)
(Aib², Thr³, Cha⁵)hGhrelin(1-28)-NH₂; (SEQ ID NO:128)
(Aib², Thr³, Abu⁶)hGhrelin(1-28)-NH₂; (SEQ ID NO:124)
(Aib², Thr³, 4Hyp⁷)hGhrelin(1-28)-NH₂; (SEQ ID NO:127)
(Aib², Thr³, Taz⁹)hGhrelin(1-28)-NH₂; (SEQ ID NO:126)
(Aib²,⁴, Thr³, 4Pal⁹)hGhrelin(1-28)-NH₂; (SEQ ID NO:129)
(Aib², Thr³, Dhp⁷)hGhrelin(1-28)-NH₂; (SEQ ID NO:127)
(Aib²,⁸, Thr³)hGhrelin(1-28)-NH₂; (SEQ ID NO:130)
(Aib², Thr³, Pip⁷)hGhrelin(1-28)-NH₂; (SEQ ID NO:127)
(Ac-Gly¹, Aib²,¹⁰, Thr³)hGhrelin(1-28)-NH₂; (SEQ ID NO:131)
(Aib²,¹⁰, Thr³)hGhrelin(1-28)-NH₂; (SEQ ID NO:131)
(n-Octanoyl-Gly¹, Thr³)hGhrelin(1-28)-NH₂; (SEQ ID NO:132)
(Isobutyryl-Gly¹, Thr³)hGhrelin(1-28)-NH₂; (SEQ ID NO:132)
(n-Butyryl-Gly¹, Thr³)hGhrelin(1-28)-NH₂; (SEQ ID NO:132)
(n-Butyryl-Gly¹, Aib², Thr³)hGhrelin(1-28)-NH₂; (SEQ ID NO:133)
(Ac-Gly¹, Aib², Thr³)hGhrelin(1-28)-NH₂; (SEQ ID NO:133)
(Aib², Thr³, Tic⁷)hGhrelin(1-28)-NH₂; (SEQ ID NO:127)
(Ac-Gly¹, Aib², Thr³, Arg⁸)hGhrelin(1-8)-NH₂; (SEQ ID NO:134)

(Thr³, Aib⁸)hGhrelin(1-28)-NH₂; (SEQ ID NO:135)
(Thr³, Taz⁹)hGhrelin(1-28)-NH₂; (SEQ ID NO:136)
(Thr³, 3Pal⁹)hGhrelin(1-28)-NH₂; (SEQ ID NO:136)
(Thr³, 4Pal⁹)hGhrelin(1-28)-NH₂; (SEQ ID NO:136)
(Aib², Thr³, 2Thi⁹)hGhrelin(1-28)-NH₂; (SEQ ID NO:126)
(Thr³, 2Thi⁹)hGhrelin(1-28)-NH₂; (SEQ ID NO:136)
(Thr³, 4Hyp⁷)hGhrelin(1-28)-NH₂; (SEQ ID NO:137)
(Aib², Thr³, Tic⁷)hGhrelin(1-28)-NH₂; (SEQ ID NO:129)
(Aib², Tic⁷)hGhrelin(1-28)-NH₂; (SEQ ID NO:9)
(Ac-Gly¹)hGhrelin(1-28)-NH₂; (SEQ ID NO:100)
(Ac-Gly¹, Glu³(NH-Hexyl))hGhrelin(1-28)-NH₂; (SEQ ID NO:138) or
(Ac-Gly¹, Ser³)hGhrelin(1-28)-NH₂, (SEQ ID NO:100) or
a pharmaceutically acceptable salt thereof.

Still another preferred compound according to formula (I), termed a Group 10 compound, is a compound according to the formula:
(Aib¹, Ser³)hGhrelin(1-28)-NH₂; (SEQ ID NO:107)
(Aib², Ser³)hGhrelin(1-28)-NH₂; (SEQ ID NO:10)
(Aib²,⁶, Ser³)hGhrelin(1-28)-NH₂; (SEQ ID NO:4)
(A5c⁵, Ser³)hGhrelin(1-28)-NH₂; (SEQ ID NO:3)
(Aib², Ser³, 3Pal⁹)hGhrelin(1-28)-NH₂; (SEQ ID NO:8)
(Aib², Ser³, Thz⁷)hGhrelin(1-28)-NH₂; (SEQ ID NO:9)
(Aib², Ser³, Cha⁵)hGhrelin(1-28)-NH₂; (SEQ ID NO:2)
(Aib², Ser³, Abu⁶)hGhrelin(1-28)-NH₂; (SEQ ID NO:4)
(Aib², Ser³, 4Hyp⁷)hGhrelin(1-28)-NH₂; (SEQ ID NO:9)
(Aib², Ser³, Taz⁹)hGhrelin(1-28)-NH₂; (SEQ ID NO:8)
(Aib²,⁴, Ser³, 4Pal⁹)hGhrelin(1-28)-NH₂; (SEQ ID NO:117)
(Aib², Ser³, Dhp⁷)hGhrelin(1-28)-NH₂; (SEQ ID NO:9)
(Aib²,⁸, Ser³)hGhrelin(1-28)-NH₂; (SEQ ID NO:11)
(Aib², Ser³, Pip⁷)hGhrelin(1-28)-NH₂; (SEQ ID NO:9)
(Ac-Gly¹, Aib²,¹⁰, Ser³)hGhrelin(1-28)-NH₂; (SEQ ID NO:139)
(Aib²,¹⁰, Ser³)hGhrelin(1-28)-NH₂; (SEQ ID NO:12)
(n-Octanoyl-Gly¹, Ser³)hGhrelin(1-28)-NH₂; (SEQ ID NO:100)
(Isobutyryl-Gly¹, Ser³)hGhrelin(1-28)-NH₂; (SEQ ID NO:100)
(n-Butyryl-Gly¹, Ser³)hGhrelin(1-28)-NH₂; (SEQ ID NO:100)
(n-Butyryl-Gly¹, Aib², Ser³)hGhrelin(1-28)-NH₂; (SEQ ID NO:140)
(Ac-Gly¹, Aib², Ser³)hGhrelin(1-28)-NH₂; (SEQ ID NO:93)
(Aib², Ser³, Tic⁷)hGhrelin(1-28)-NH₂; (SEQ ID NO:9)
(Ac-Gly¹, Aib², Ser³, Arg⁸)hGhrelin(1-8)-NH₂; (SEQ ID NO:120)
(Ser³, Aib⁸)hGhrelin(1-28)-NH₂; (SEQ ID NO:121)
(Ser³, Taz⁹)hGhrelin(1-28)-NH₂; (SEQ ID NO:14)
(Ser³, 3Pal⁹)hGhrelin(1-28)-NH₂; (SEQ ID NO:14)
(Ser³, 4Pal⁹)hGhrelin(1-28)-NH₂; (SEQ ID NO:14)
(Aib², Ser³, 2Thi⁹)hGhrelin(1-28)-NH₂; (SEQ ID NO:8)
(Ser³, 2Thi⁹)hGhrelin(1-28)-NH₂; (SEQ ID NO:14)
(Ser³, 4Hyp⁷)hGhrelin(1-28)-NH₂; (SEQ ID NO:15) or
(Aib², Ser³, Tic⁷)hGhrelin(1-28)-NH₂, (SEQ ID NO:9) or
a pharmaceutically acceptable salt thereof.

Still yet another preferred compound according to formula (I), termed a Group 11 compound, is a compound according to the formula:
(Aib¹, Ser³)hGhrelin(1-28)-NH₂; (SEQ ID NO:107)
(Aib², Ser³)hGhrelin(1-28)-NH₂; (SEQ ID NO:10)
(Aib²,⁶, Ser)hGhrelin(1-28)-NH₂; (SEQ ID NO:4)
(A5c⁵, Ser³)hGhrelin(1-28)-NH₂; (SEQ ID NO:3)
(Aib², Ser³, 3Pal⁹)hGhrelin(1-28)-NH₂; (SEQ ID NO:8)
(Aib², Ser³, Thz⁷)hGhrelin(1-28)-NH₂; (SEQ ID NO:9)
(Aib², Ser³, Cha⁵)hGhrelin(1-28)-NH₂; (SEQ ID NO:2)
(Aib², Ser³, Abu⁶)hGhrelin(1-28)-NH₂; (SEQ ID NO:4)
(Aib², Ser³, 4Hyp⁷)hGhrelin(1-28)-NH₂; (SEQ ID NO:9)
(Aib², Ser³, Taz⁹)hGhrelin(1-28)-NH₂; (SEQ ID NO:8)
(Aib²,⁴, Ser³, 4Pal⁹)hGhrelin(1-28)-NH₂; (SEQ ID NO:117)
(Aib², Ser³, Dhp⁷)hGhrelin(1-28)-NH₂; (SEQ ID NO:9)
(Aib²,⁸, Ser³)hGhrelin(1-28)-NH₂; (SEQ ID NO:11)
(Aib², Ser³, Pip⁷)hGhrelin(1-28)-NH₂; (SEQ ID NO:9)
(Ac-Gly¹, Aib²,¹⁰, Ser³)hGhrelin(1-28)-NH₂; (SEQ ID NO:139)
(Aib²,¹⁰, Ser³)hGhrelin(1-28)-NH₂; (SEQ ID NO:12)
(n-Octanoyl-Gly¹, Ser³)hGhrelin(1-28)-NH₂; (SEQ ID NO:100)
(Isobutyryl-Gly¹, Ser³)hGhrelin(1-28)-NH₂; (SEQ ID NO:100)
(n-Butyryl-Gly¹, Ser³)hGhrelin(1-28)-NH₂; (SEQ ID NO:100)
(n-Butyryl-Gly¹, Aib², Ser³)hGhrelin(1-28)-NH₂; (SEQ ID NO:19)
(Ac-Gly¹, Aib², Ser³)hGhrelin(1-28)-NH₂; (SEQ ID NO:93)
(Aib², Ser³, Tic⁷)hGhrelin(1-28)-NH₂; (SEQ ID NO:9)
(Ac-Gly¹, Aib², Ser³, Arg⁸)hGhrelin(1-8)-NH₂; (SEQ ID NO:120)
(Ser³, Aib⁸)hGhrelin(1-28)-NH₂; (SEQ ID NO:121)
(Ser³, Taz⁹)hGhrelin(1-28)-NH₂; (SEQ ID NO:14)
(Ser³, 3Pal⁹)hGhrelin(1-28)-NH₂; (SEQ ID NO:14)
(Ser³, 4Pal⁹)hGhrelin(1-28)-NH₂; (SEQ ID NO:14)
(Aib², Ser³, 2Thi⁹)hGhrelin(1-28)-NH₂; (SEQ ID NO:8)
(Ser³, 2Thi⁹)hGhrelin(1-28)-NH₂; (SEQ ID NO:14)
(Ser³, 4Hyp⁷)hGhrelin(1-28)-NH₂; (SEQ ID NO:15) or
(Aib², Ser³, Tic⁷)hGhrelin(1-28)-N₂, (SEQ ID NO:9) or a pharmaceutically acceptable salt thereof.

Yet still another preferred compound according to formula (I), termed a Group 12 compound, is a compound according to the formula:
(Aib², Tic⁷)hGhrelin(1-28)-NH₂; (SEQ ID NO:9)
(Ac-Gly¹)hGhrelin(1-28)-NH₂; (SEQ ID NO:100)
(Ac-Gly¹, Glu³(NH-Hexyl))hGhrelin(1-28)-NH₂; (SEQ ID NO:138) or
(Ac-Gly¹, Ser³)hGhrelin(1-28)-NH₂, (SEQ ID NO:100) or
a pharmaceutically acceptable salt thereof.

Ghrelin analogs described herein are active at one or more of the GHS receptors. The analogs can bind to a receptor, and preferably, stimulate receptor activity. Ghrelin analogs have a variety of different uses including being used as a research tool and being used therapeutically.

Research tool applications generally involve the use of a ghrelin analog and the presence of a GHS receptor or fragment thereof. The GHS receptor can be present in different environments such as a mammalian subject, a whole cell, or a membrane fragment. Examples of research tool applications include screening for compounds active at the GHS receptor, determining the presence of the GHS receptor in a sample or preparation, and examining the role or effect of ghrelin.

Ghrelin analogs can be used to screen for either ghrelin agonists or ghrelin antagonists. Screening for ghrelin agonists can be performed, for example, by using a ghrelin analog in a competition experiment with test compounds. Screening for ghrelin antagonists can be performed, for example, by using a ghrelin analog to produce GHS receptor activity and then measuring the ability of a compound to alter GHS receptor activity.

Thus, another aspect of the present invention features a method of screening for a compound able to bind to a GHS receptor. The method comprises the step of measuring the ability of a compound to affect binding of a ghrelin analog to either the receptor, a fragment of the receptor comprising a ghrelin binding site, a polypeptide comprising the fragment, or a derivative of the polypeptide.

Another aspect of the present invention features a method for achieving a beneficial affect in a subject comprising, said method comprising the step of administering to the subject an effective amount of one or more of a compound according to formula (I), more preferably a compound according to one or more of Group 1, Group 2, Group 3, Group 4, Group 5, Group 6, Group 7, Group 8, Group 9, Group 10, Group 11, and/or Group 12, or a pharmaceutically acceptable salt thereof, wherein the amount administered is effective for producing a beneficial effect in treating (e.g., curing or reducing the severity) or preventing (e.g., reducing the likelihood of onset or severity) a disease or disorder.

Ghrelin induces growth hormone release from primary-culture pituitary cells in a dose-dependent manner without stimulating the release of the other pituitary hormones. Injected intravenously into anaesthetized rats, ghrelin stimulated pulsatile release of growth hormone. (Kojima et al., *Nature* 1999, 402, 656-660.)

Thus another aspect of the present invention features a method for stimulating growth hormone secretion in a subject in need of such stimulation, comprising the step of administering to a subject an effective amount of one or more of a compound according to formula (I), more preferably a compound according to one or more of Group 1, Group 2, Group 3, Group 4, Group 5, Group 6, Group 7, Group 8, Group 9, Group 10, Group 11, and/or Group 12, or a pharmaceutically acceptable salt thereof, wherein said effective amount is at least an amount sufficient to produce a detectable increase in growth hormone secretion and, preferably, is an amount sufficient to achieve a beneficial affect in the subject.

A preferred method of the immediately preceding method is wherein said stimulation of growth hormone secretion is indicated for treatment of a growth hormone deficient state, for increasing muscle mass, for increasing bone density, for sexual dysfunction in males or females, for facilitating a weight gain, for facilitating maintenance of weight, for facilitating maintenance of physical functioning, for facilitating recovery of physical function, and/or facilitating appetite increase.

A preferred method of the immediately preceding method is where the facilitation of weight gain, maintenance in weight, and/or appetite increase is indicated in a subject having a disease or disorder, or undergoing a treatment that is accompanied by weight loss.

A preferred method of the immediately preceding method is where said diseases or disorders accompanied by weight loss include anorexia, bulimia, cancer cachexia, AIDS, wasting, cachexia, and wasting in frail, elderly subjects. Another preferred method of the immediately preceding method is where the treatment accompanied by weight loss includes chemotherapy, radiation therapy, temporary or permanent immobilization, and/or dialysis.

Ghrelin analogs described herein may also antagonize the effects of ghrelin in vitro and in vivo. Thus, yet another aspect of the present invention features a method for suppressing growth hormone secretion in a subject in need of such suppression, comprising the step of administering to the subject an effective amount of one or more of a compound according to formula (I), more preferably a compound according to one or more of Group 1, Group 2, Group 3, Group 4, Group 5, Group 6, Group 7, Group 8, Group 9, Group 10, Group 11, and/or Group 12, or a pharmaceutically acceptable salt thereof, wherein the effective amount is at least an amount sufficient to produce a detectable decrease in growth hormone secretion and, preferably, is an amount sufficient to achieve a beneficial affect in the subject.

A preferred method of the immediately preceding method is where the suppression of growth hormone secretion is indicated for the treatment of a disease or condition characterized by excessive growth hormone secretion, for the facilitation of weight loss, for the facilitation of appetite decrease, for the facilitation of weight maintenance, for treating obesity, for treating diabetes, for treating complications of diabetes including retinopathy, and/or for treating cardiovascular disorders.

A preferred method of the immediately preceding method is where excessive weight is a contributing factor to a disease or condition, including hypertension, diabetes, dyslipidemia, cardiovascular disease, gall stones, osteoarthritis and various cancers. A further preferred method of the immediately preceding method is where the facilitation of weight loss reduces the likelihood of such diseases or conditions or where the facilitation of weight loss comprises at least part of a treatment for such diseases or conditions.

Another aspect of the present invention features a method for treating a cardiovascular disorder in a subject in need of such treatment, comprising the step of administering to the subject an effective amount of one or more of a compound, or a pharmaceutically acceptable salt thereof, according to formula (I), more preferably a compound according to one or more of Group 1, Group 2, Group 3, Group 4, Group 5, Group 6, Group 7, Group 8, Group 9, Group 10, Group 11, and/or Group 12, and most preferably, a ghrelin receptor agonist, wherein the effective amount is an amount sufficient to achieve a beneficial affect in the subject. In one embodiment, the cardiovascular disorder is severe chronic heart failure. In another embodiment, the compound inhibits apoptosis in cardiomyocytes and/or endothelial cells.

Another aspect of the present invention features a method for eliciting an effect, in a subject mediated by ghrelin receptor agonism (e.g., treating or preventing musculoskeletal frailty, treating or preventing diabetes, treating or preventing congestive heart failure, treating or preventing obesity, treating or preventing frailty associated with aging or frailty associated with obesity, treating insulin resistance, accelerating bone fracture repair, attenuating protein catabolic response after a major operation, reducing cachexia and protein loss due to chronic illness, accelerating wound healing, accelerating the recovery of burn patients or patients having undergone major surgery, improving muscle strength or mobility, improving maintenance of skin thickness, maintaining metabolic homeostasis, or maintaining renal homeostasis), in which the compound binds to one or more growth hormone secretagogue receptors. The method includes the step of administering to the subject an effective amount of one or more of a compound, or a pharmaceutically acceptable salt thereof, according to formula (I), more preferably a compound according to one or more of Group 1, Group 2, Group 3, Group 4, Group 5, Group 6, Group 7, Group 8, Group 9, Group 10, Group 11, and/or Group 12, and most preferably a compound in which $A^3$ is Ser, Glu, Dap, or Dab, wherein the compound is an agonist for the receptor(s) and is administered in an amount sufficient to elicit the effect.

Yet another aspect of the present invention features a method for eliciting an effect, in a subject mediated by ghrelin receptor antagonism (e.g., appetite suppression, weight loss, or reduction of metabolism), in which the compound binds to one or more growth hormone secretagogue receptors. The method includes the step of administering to the subject an effective amount of one or more of a compound, or a pharmaceutically acceptable salt thereof, according to formula (I), more preferably a compound according to one or more of Group 1, Group 2, Group 3, Group 4, Group 5, Group 6, Group 7, Group 8, Group 9, Group 10, Group 11, and/or Group 12, and most preferably a compound in which $A^3$ is Ser, Glu, Dap, or Dab, wherein the compound is an antagonist for the receptor(s) and is administered in an amount sufficient to elicit the effect.

Ghrelin analogs can be administered to a subject. A "subject" refers to a mammalian or non-mammalian animal including, for example and without limitation, a human, a rat, a mouse, or a farm animal. Reference to subject does not necessarily indicate the presence of a disease or disorder. The term subject includes, for example, a mammalian or non-mammalian animal being dosed with a ghrelin analog as part of an experiment, a mammalian or non-mammalian animal being treated to help alleviate a disease or disorder, and a mammalian or non-mammalian animal being treated prophylactically to retard or prevent the onset of a disease or disorder.

Ghrelin agonists can be used to achieve a beneficial effect in a subject such as one or more of the following: treating a growth hormone deficient state, increasing muscle mass, increasing bone density, treating sexual dysfunction in males or females, facilitating a weight gain, facilitating maintenance of weight, facilitating maintenance of physical functioning, facilitating recovery of physical function, and/or facilitating appetite increase. Facilitating a weight gain, maintenance in weight, or appetite increase is particularly useful for a patient having a disease or disorder, or under going a treatment, that is accompanied by weight loss. Examples of diseases or disorders accompanied by weight loss include anorexia, bulimia, cancer cachexia, AIDS, wasting, cachexia, and wasting in frail elderly. Examples of treatments accompanied by weight loss include chemotherapy, radiation therapy, temporary or permanent immobilization, and dialysis.

Ghrelin antagonists can also be used to achieve a beneficial effect in a subject. For example, a ghrelin antagonist can be used to facilitate weight loss, facilitate appetite decrease, facilitate weight maintenance, treat obesity, treat diabetes, treat complications of diabetes including retinopathy, and/or treat cardiovascular disorders. Excessive weight is a contributing factor to different diseases including hypertension, diabetes, dyslipidemias, cardiovascular disease, gall stones, osteoarthritis and certain forms of cancers. Bringing about a weight loss can be used, for example, to reduce the likelihood of such diseases and as part of a treatment for such diseases.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

Unless otherwise stated, those amino acids with a chiral center are provided in the L-enantiomer. Reference to "a derivative thereof" refers to a modified amino acid such as the corresponding D-amino acid, a N-alkyl-amino acid, a β-amino acid, or a labeled amino acid.

DETAILED DESCRIPTION

The present invention features ghrelin analogs active at the GHS receptor. Human ghrelin is a 28 amino acid modified peptide where a serine hydroxyl group is esterified by n-octanoic acid (Kojima et al., Nature 1999, 402, 656-660, and Kojima, Abstract at the Third International Symposium on Growth Hormone Secretagogues, Keystone, Colo., USA 2000, Feb. 17-19).

Certain amino acids present in compounds of the invention can be and are represented herein as follows:
Abu is α-aminobutyric acid,
Aic is 2-aminoindane-2-carboxylic acid,
Acc is 1-amino-1-cyclo($C_3$-$C_9$)alkyl carboxylic acid,
A3c is 1-amino-1-cyclopropanecarboxylic acid,
A4c is 1-amino-1-cyclobutanecarboxylic acid,
A5c is 1-amino-1-cyclopentanecarboxylic acid,
A6c is 1-amino-1-cyclohexanecarboxylic acid,
Act is 4-amino-4-carboxytetrahydropyran, which has the structure:

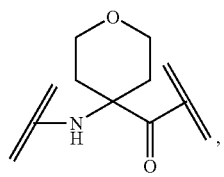

Aib is α-aminoisobutyric acid,
Ala or A is alanine,
β-Ala is beta-alanine,
Apc denotes the structure:

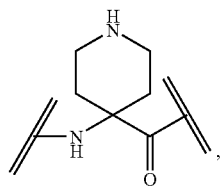

Arg or R is arginine,
hArg is homoarginine,
Asn or N is asparagine,
Asp or D is aspartic acid,
Cha is β-cyclohexylalanine,
Cys or C is cysteine,
Dab is 2,4-diaminobutyric acid,
Dap is 2,3-diaminoproprionic acid,
Dhp is 3,4-dehydroproline,
Dmt is 5,5-dimethylthiazolidine-4-carboxylic acid,
2Fua is β-(2-furyl)-alanine,
Gln or Q is glutamine,
Glu or E is glutamic acid,
Gly or G is glycine,
His or H is histidine,
3Hyp is trans-3-hydroxy-L-proline, i.e., (2S,3S)-3-hydroxypyrrolidine-2-carboxylic acid,
4Hyp is 4-hydroxyproline, i.e., (2S,4R)-4-hydroxypyrrolidine-2-carboxylic acid,
Ile or I is isoleucine,
Inc is indoline-2-carboxylic acid,
Inp is isonipecotic acid,
Ktp is 4-ketoproline,
Leu or L is leucine,
hLeu homoleucine,
Lys or K is lysine,
Met or M is methionine, Nle is norleucine,
Nva is norvaline,
Oic is octahydroindole-2-carboxylic acid,
Orn is ornithine,
2Pal is β-(2-pyridinyl)alanine,
3Pal is β-(3-pyridinyl)alanine,
4Pal is β-3-(4-pyridinyl)alanine,
Phe or F is phenylalanine,
hPhe is homophenylalanine,
Pip is pipecolic acid,
Pro or P is proline,
Ser or S is serine,
Taz is β-(4-thiazolyl)alanine, which has the structure:

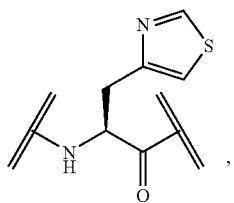

2Thi is β-(2-thienyl)alanine,
3Thi is β-(3-thienyl)alanine,
Thr or T is threonine,
Thz is thiazolidine-4-carboxylic acid,
Tic is 1,2,3,4-tetrahydroisoquinoline-3-carboxylic acid,
Tle is tert-leucine,
Trp or W is tryptophan,
Tyr or Y is tyrosine, and
Val or V is valine.

Certain other abbreviations used herein are defined as follows:
Boc is tert-butyloxycarbonyl,
Bzl is benzyl,
DCM is dichloromethane,
DIC is N,N-diisopropylcarbodiimide,
DIEA is diisopropylethyl amine,
Dmab is 4-{N-(1-(4,4-dimethyl-2,6-dioxocyclohexylidene)-3-methylbutyl)-amino}benzyl,
DMAP is 4-(dimethylamino)pyridine,
DMF is dimethylformamide,
DNP is 2,4-dinitrophenyl,
Fmoc is Fluorenylmethyloxycarbonyl,
HBTU is 2-(1H-benzotriazole-1-yl)-1,1,3,3-tetramethyluronium hexafluorophosphate,
cHex is cyclohexyl,
HOAt is O-(7-azabenzotriazol-1-yl)-1,1,3,3-tetramethyluronium hexafluorophosphate,
HOBt is 1-hydroxy-benzotriazole,
Mmt is 4-methoxytrityl,
NM is N-methylpyrrolidone,
Pbf is 2,2,4,6,7-pentamethyldihydrobenzofuran-5-sulfonyl,
tBu is tert-butyl,
TIS is triisopropylsilane,
TOS is tosyl,
trt is trityl,
TFA is trifluoro acetic acid,
TFFH is tetramethylfluoroforamidinium hexafluorophosphate, and
Z is benzyloxycarbonyl.

With the exception of the N-terminal amino acid, all abbreviations (e.g., Ala) of amino acids in this disclosure stand for the structure of —NH—C(R)(R')—CO—, wherein R and R' each is, independently, hydrogen or the side chain of an amino acid (e.g., R=CH$_3$ and R'=H for Ala), or R and R' may be joined to form a ring system. For the N-terminal amino acid, the abbreviation stands for the structure of (R$^2$R$^3$)—N—C(R)(R')—CO—, wherein R$^2$ and R$^3$ are as defined in formula (I).

A peptide of this invention is also denoted herein by another format, e.g., (Aib$^2$)hGhrelin(1-28)-NH$_2$, with the substituted amino acid(s) from the natural sequence placed between the first set of parentheses (e.g., Aib$^2$ for Ser$^2$ in hGhrelin). The numbers between the second set of parentheses refer to the number of amino acids present in the peptide (e.g., hGhrelin(1-18) refers to amino acids 1 through 18 of the peptide sequence for human Ghrelin). The designation "NH$_2$" in e.g., (Aib$^2$)hGhrelin(1-28)-NH$_2$, indicates that the C-terminus of the peptide is amidated. (Aib$^2$)hGhrelin(1-28), or alternatively (Aib$^2$)hGhrelin(1-28)-OH, indicates that the C-terminus is the free acid.

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$, and —(CH$_2$)$_{0-4}$—COOH. In different embodiments 1, 2, 3 or 4 substituents are present. The presence of —(CH$_2$)$_{0-4}$—COOH results in the production of an alkyl acid. Examples of alkyl acids containing, or consisting of, —(CH$_2$)$_{0-4}$—COOH include 2-norbornane acetic acid, tert-butyric acid and 3-cyclopentyl propionic acid.

"Heteroalkyl" refers to an alkyl wherein one of more of the carbon atoms in the hydrocarbon group are replaced with one or more of the following groups: amino, amido, —O—, or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$, and —(CH$_2$)$_{0-4}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$, and —(CH$_2$)$_{0-4}$—COOH. In different embodiments 1, 2, 3 or 4 substituents are present.

"Aryl" refers to an optionally substituted aromatic group with at least one ring having a conjugated pi-electron system, containing up to two conjugated or fused ring systems. Aryl includes carbocyclic aryl, heterocyclic aryl and biaryl groups.

Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, quinoline, 2-imidazole, and 9-anthracene. Aryl substituents are selected from the group consisting of —$C_{1-4}$ alkyl, —$C_{1-4}$ alkoxy, halogen (i.e., fluorine, chlorine, bromine, and iodine), —OH, —CN, —SH, —$NH_2$, —$NO_2$, —$C_{1-2}$ alkyl substituted with 1 to 5 halogens, —$CF_3$, —$OCF_3$, and —$(CH_2)_{0-4}$—COOH. In different embodiments the aryl contains 0, 1, 2, 3, or 4 substituents.

"Alkylaryl" refers to an "alkyl" joined to an "aryl".

What is meant by "Glu(O-Hexyl)" is

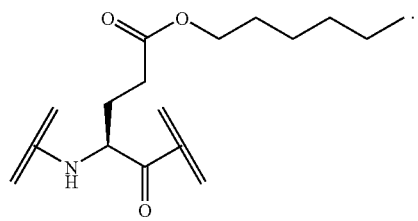

What is meant by "Glu(NH-Hexyl)" is

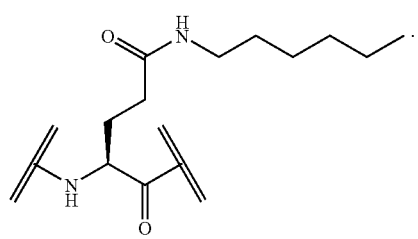

What is meant by "Dap(1-Octanesulfonyl)" is

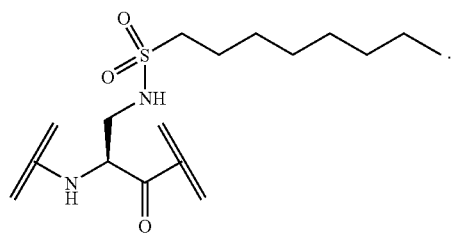

What is meant by "Cys($R^{15}$)" is

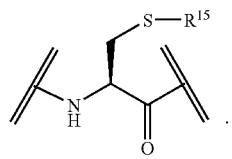

What is meant by "Cys(S-Heptyl)" is

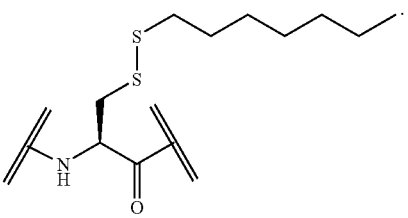

What is meant by "Dap(Octanoyl)" is

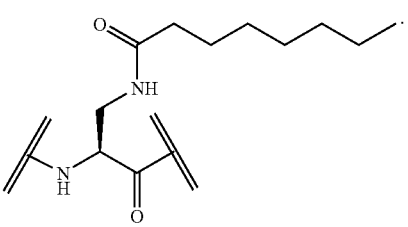

The present invention includes diastereomers as well as their racemic and resolved enantiomerically pure forms. Ghrelin analogs can contain D-amino acids, L-amino acids or a combination thereof. Preferably, amino acids present in a ghrelin analog are the L-enantiomers.

Preferred derivatives of analogs of the invention comprise D-amino acids, N-alkyl-amino acids, β-amino acids, and/or one or more labeled amino acids (including a labeled version of a D-amino acid, a N-alkyl-amino acids, or a β-amino acid). A labeled derivative indicates the alteration of an amino acid or amino acid derivative with a detectable label. Examples of detectable labels include luminescent, enzymatic, and radioactive labels. Both the type of label and the position of the label can effect analog activity. Labels should be selected and positioned so as not to substantially alter the activity of the ghrelin analog at the GHS receptor. The effect of a particular label and position on ghrelin activity can be determined using assays measuring ghrelin activity and/or binding.

A protecting group covalently joined to the C-terminal carboxy group reduces the reactivity of the carboxy terminus under in vivo conditions. The carboxy terminus protecting group is preferably attached to the α-carbonyl group of the last amino acid. Preferred carboxy terminus protecting groups include amide, methylamide, and ethylamide.

EXAMPLES

Examples are provided below to further illustrate different features of the present invention. The examples also illustrate useful methodology for practicing the invention. These examples do not limit the claimed invention.

Synthesis

The compounds of the invention can be produced using the techniques disclosed in the examples herein as well as techniques that are well known in the art. For example, a polypeptide region of a ghrelin analog can be chemically or biochemically synthesized and modified. Examples of techniques for biochemical synthesis involving the introduction of a nucleic acid into a cell and expression of nucleic acids are provided in Ausubel, *Current Protocols in Molecular Biology*, John Wiley, 1987-1998, and Sambrook et al., in *Molecular Clon-* ing, *A Laboratory Manual*, 2$^{nd}$ Edition, Cold Spring Harbor Laboratory Press, 1989. Techniques for chemical synthesis of polypeptides are also well known in the art (See e.g., Vincent in *Peptide and Protein Drug Delivery*, New York, N.Y., Dekker, 1990). For example, the peptides of this invention can be prepared by standard solid phase peptide synthesis (See, e.g., Stewart, J. M., et al., *Solid Phase Synthesis* (Pierce Chemical Co., 2d ed. 1984)).

The substituents $R^2$ and $R^3$ of the above generic formula may be attached to the free amine of the N-terminal amino acid by standard methods known in the art. For example, alkyl groups, e.g., ($C_1$-$C_{30}$)alkyl, may be attached using reductive alkylation. Hydroxyalkyl groups, e.g., ($C_1$-$C_{30}$)hydroxyalkyl, may also be attached using reductive alkylation wherein the free hydroxy group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for one hour. If the free acid contains a free hydroxy group, e.g., p-hydroxyphenylpropionic acid, then the coupling should be performed with an additional 3 molar equivalents of HOBt.

When $R^1$ is $NH-X^2-CH_2-CONH_2$, (i.e., $Z^0=CONH_2$), the synthesis of the peptide starts with $BocHN-X^2-CH_2-COOH$, which is coupled to the MBHA resin. If $R^1$ is $NH-X^2-CH_2-COOH$ (i.e., $Z^0=COOH$), the synthesis of the peptide starts with $Boc-HN-X^2-COOH$, which is coupled to PAM resin. For this particular step, 4 molar equivalents of $Boc-HN-X^2-COOH$, HBTU and HOBt and 10 molar equivalents of DIEA are used. The coupling time is about 8 hours.

The protected amino acid 1-(N-tert-butoxycarbonylamino)-1-cyclohexane-carboxylic acid (Boc-A6c-OH) was synthesized as follows: 19.1 g (0.133 mol) of 1-amino-1-cyclohexanecarboxylic acid (Acros Organics, Fisher Scientific, Pittsburgh, Pa.) was dissolved in 200 ml of dioxane and 100 ml of water. To it was added 67 ml of 2N NaOH. The solution was cooled in an ice-water bath and 32.0 g (0.147 mol) of di-tert-butyl-dicarbonate was added to this solution. The reaction mixture was stirred overnight at room temperature. Dioxane was then removed under reduced pressure and 200 ml of ethyl acetate was added to the remaining aqueous solution. The mixture was cooled in an ice-water bath. The pH of the aqueous layer was adjusted to about 3 by adding 4N HCl. The organic layer was separated. The aqueous layer was extracted with ethyl acetate (1×100 ml). The two organic layers were combined and washed with water (2×150 ml), dried over anhydrous $MgSO_4$, filtered, and concentrated to dryness under reduced pressure. The residue was recrystallized in ethyl acetate/hexanes and 9.2 g of the pure product was obtained, 29% yield.

Boc-A5c-OH was synthesized in an analogous manner to that of Boc-A6c-OH. Other protected Acc amino acids can be prepared in an analogous manner by a person of ordinary skill in the art as enabled by the teachings herein.

In the synthesis of a ghrelin analogue of this invention containing A5c, A6c and/or Aib, the coupling time is 2 hours for these residues and the residue immediately following them.

Example 1

(Glu$^3$(O-Hexyl))hGhrelin(1-28)-$NH_2$ (SEQ ID NO:86)

The titled peptide was synthesized on an Applied Biosystems (Foster City, Calif.) model 433A peptide synthesizer. 4-(2',4'-Dimethoxyphenyl-Fmoc-aminomethyl)-phenoxyacetamido-norleucyl-MBHA resin (Rink Amide MBHA resin, Novabiochem, San Diego, Calif.) was used with a substitution of 0.72 mmol/g. The Fmoc amino acids (AnaSpec, San Jose, Calif.) were used with the following side chain protection: Fmoc-Arg(Pbf)-OH, Fmoc-Pro-OH, Fmoc-Gln-OH, Fmoc-Leu-OH, Fmoc-Lys(Boc)-OH, Fmoc-Ala-OH, Fmoc-Ser(tBu)-OH, Fmoc-Glu(OtBu)-OH, Fmoc-Val-OH, Fmoc-His(Trt)-OH, Fmoc-Phe-OH, and Fmoc-Asp(OtBu)-OH. Boc-Gly-OH (Midwest Bio-Tech, Fishers, Ind.) was used in position 1. N-α-Fmoc-L-glutamic acid γ-4-{N-(1-(4,4-dimethyl-2,6-dioxocyclohexylidene)-3-methylbutyl)-amino} benzyl ester (Fmoc-Glu(ODmab)-OH) (Chem-Inpex International, Wood Dale, Ill.) was used in position 3. The synthesis was carried out on a 0.25 mmol scale. The Fmoc groups were removed by treatment with 20% piperidine in N-methylpyrrolidone (NMP) for 30 min. In each coupling step, the Fmoc amino acid (1 mmol) was first pre-activated with HBTU (0.9 mmol) and HOBt (0.9 mmol) in DMF and then added to the resin. The ABI 433A peptide synthesizer was programmed to perform the following reaction cycle: (1) washing with NMP, (2) removing Fmoc protecting group with 20% piperidine in NMP for 30 min, (3) washing with NMP, (4) coupling with pre-activated Fmoc amino acid for 1 h.

At the end of assembly of the peptide chain on the Applied Biosystems (ABI) 433A peptide synthesizer, the resin was transferred into a reaction vessel on a shaker for manual synthesis. The Dmab protecting group in the side chain of the Glu residue was removed with a solution of 2% hydrazine in DMF for 2 h. After washing with DMF, the resin was treated with 2.5 mmol of tetramethylfluoroforamidinium hexafluorophosphate (TFFH) (Perseptive Biosystems, Warrington, UK) in dichloromethane (DCM) for 25 min to convert the free carboxylic acid functional group in the side chain of the Glu residue to its acid fluoride. To the mixture were added 5.0 mmol of hexanol, 2.5 mmol of O-(7-azabenzotriazol-1-yl)-1,1,3,3-tetramethyluronium hexafluorophosphate (HOAT)(Anaspec, San Jose, Calif.), 5.0 mmol of diisopropylethyl amine (DIEA)(Aldrich, Milwaukee, Wis.) and catalytic amount of 4-(dimethylamino)pyridine (DMAP)(Aldrich, Milwaukee, Wis.). The mixture was shaken at room temperature for 2 h. The resin was washed with DMF and DCM and treated overnight with 2.5 mmol of N,N-diisopropylcarbodiimide (DIC) (Chem-Impex International, Wood Dale, Ill.), 2.5 mmol of 1-hexanol, 2.5 mmol of HOBt, and 0.025 mmol of DMAP. After washing and drying, the peptide was cleaved off from the resin by using a mixture of TFA (9.5 mL), $H_2O$ (0.85 mL) and triisopropylsilane (TIS) (0.85 mL) for 2 h. The resin was filtered off and the filtrate was poured into 70 mL of ether. The precipitate formed was filtered off and washed thoroughly with ether. This crude product was dissolved into 5% acetic acid and purified on a reverse-phase preparative HPLC using a column (4×43 cm) of $C_{18}$ DYNAMAX-100A° (Varian, Walnut Creek, Calif.). The column was eluted with a linear gradient from 75% A and 25% B to 55% A and 45% B in an hour where A was 0.1% TFA in water and B was 0.1% TFA in acetonitrile. The fractions were checked by an analytical HPLC. Those containing pure product were combined and lyophilized to dryness. The purity of the compound was 92.8%. Yield was 8.6%. Electro-spray ionization mass spectrometry (ESI MS) analysis gave a molecular weight for the product of 3369.4 (in agreement with the calculated molecular weight of 3369.9).

Example 2

(Aib$^2$)hGhrelin(1-28)-NH$_2$ (SEQ ID NO:10)

The titled peptide was synthesized according to the procedure described in Example 1 for the synthesis of (Glu 3(O-Hexyl))hGhrelin(1-28)-NH$_2$, except as follows: Fmoc-Ser-OH was used at position 3, Fmoc-Aib-OH was used at position 2 and Boc-Gly-OH was used at position 1. After the peptide chain was assembled, the peptide-resin was treated with 25% piperidine in DMF for 3×2 h. The resin was washed with DMF and treated with octanoic acid (2.5 mmol, 10 fold excess), HBTU (2.2 mmol), HOBt (2.2 mmol) and DIEA (7.5 mmol) in DMF for 2 h. The resin was washed with DMF and then treated with octanoic acid (2.5 mmol), DIC (2.5 mmol), HOBt (2.5 mmol) and DMAP (0.025 mmol) in DMF for 2 h. The final cleavage and purification procedures were the same as those in Example 1. The product was found to be homogenous by analytical HPLC, with a purity of 99% in 18.5% yield. Electro-spray ionization mass spectrometry (ESI MS) analysis gave a molecular weight for the product of 3367.6 (in agreement with the calculated molecular weight of 3367.0).

Example 3

(Glu$^3$(NH-Hexyl))hGhrelin(1-28)-NH$_2$ (SEQ ID NO:106)

The titled peptide was synthesized on an Applied Biosystems (Foster City, Calif.) model 430A peptide synthesizer which was modified to do accelerated Boc-chemistry solid phase peptide synthesis. See Schnolzer, et al., Int. J. Peptide Protein Res., 40:180 (1992). 4-Methylbenzhydrylamine (MBHA) resin (Peninsula, Belmont, Calif.), with a substitution of 0.91 mmol/g was used. Boc amino acids (Midwest Bio-Tech, Fishers, Ind.; Novabiochem., San Diego, Calif.) were used with the following side chain protection: Boc-Ala-OH, Boc-Arg(Tos)-OH, Boc-His(DNP)-OH, Boc-Val-OH, Boc-Leu-OH, Boc-Gly-OH, Boc-Gln-OH, Boc-Lys(2ClZ)-OH, Boc-Ser(Bzl)-OH, Boc-Phe-OH, Boc-Glu(OcHex)-OH and Boc-Pro-OH. Fmoc-Glu(OtBu)-OH (Novabiochem., San Diego, Calif.) was used for the residue at position 3 in the sequence. The synthesis was carried out on a 0.25 mmol scale. The Boc groups were removed by treatment with 100% TFA for 2×1 min. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 min.

At the end of the assembly of the first 25 residues on the ABI 430A peptide synthesizer and before the coupling of Fmoc-Glu(OtBu)-OH, the protected peptide-resin was transferred into a reaction vessel on a shaker for manual synthesis. After removing the Boc protecting group by using 100% TFA for 2×1 min and washing with DMF, the resin was mixed with Fmoc-Glu(OtBu)-OH (2.5 mmol) which was pre-activated with HBTU (2.0 mmol), HOBt (2.0 mmol) and DIEA (1.0 mL) in 4 mL of DMF. The mixture was shaken for 2 h. This coupling step was repeated. After washing with DMF, the resin was treated with a TFA solution containing 5% water and 5% TIS for 2 h to remove the tBu protecting group in the side chain of the Glu residue. The resin was neutralized with 10% DIEA in DMF and washed with DMF and DCM. The resin was then treated with hexylamine (2.0 mmol), DIC (2.0 mmol), HOBt (2.0 mmol) in 5 ml of DCM for 2×2 h. The resin was washed with DMF and treated with 25% piperidine in DMF for 30 min to remove the Fmoc protecting group. After washing with DMF and DCM, the resin was transferred into the reaction vessel on the ABI 430A peptide synthesizer for the assembly of the rest two residues.

At the end of the assembly of the whole peptide chain, the resin was treated with a solution of 20% mercaptoethanol/10% DIEA in DMF for 2×30 min to remove the DNP group on the His side chain. The N-terminal Boc group was then removed by treatment with 100% TFA for 2×2 min. The peptide-resin was washed with DMF and DCM and dried under reduced pressure. The final cleavage was done by stirring the peptide-resin in 10 mL of HF containing 1 mL of anisole and dithiothreitol (50 mg) at 0° C. for 75 min. HF was removed by a flow of nitrogen. The residue was washed with ether (6×10 mL) and extracted with 4N HOAc (6×10 mL). This crude product was purified on a reverse-phase preparative HPLC using a column (4×43 cm) of C$_{18}$ DYNAMAX-100A° (Varian, Walnut Creek, Calif.). The column was eluted with a linear gradient from 75% A and 25% B to 55% A and 45% B at flow rate of 10 mL/min in an hour where A was 0.1% TFA in water and B was 0.1% TFA in acetonitrile. Fractions were collected and checked on an analytical HPLC. Those containing pure product were combined and lyophilized to dryness. 31.8 mg of a white solid were obtained. Purity was 89% based on analytical HPLC analysis. Electro-spray ionization mass spectrometry (ESI MS) analysis gave the molecular weight at 3368.4 (in agreement with the calculated molecular weight of 3368.9).

Example 4

(Cys$^3$(S-Decyl))hGhrelin(1-28)-NH$_2$ (SEQ ID NO:108)

(i) The titled peptide was synthesized according to the procedure described in Example 3 for the synthesis of (Glu$^3$(NH-Hexyl))hGhrelin(1-28)-NH$_2$ with the following modifications: After the assembly of the first 25 residues using Boc chemistry, the last 3 residues were assembled by employing Fmoc chemistry. The following 3 Fmoc amino acids were used: N-α-Fmoc-S-(p-methoxytrityl)-L-cysteine (Fmoc-Cys (Mmt)-OH), Fmoc-Ser(Bzl)-OH and Fmoc-Gly-OH, which were purchased from Novabiochem (San Diego, Calif.). The Fmoc amino acid (1 mmol) was first pre-activated with HBTU (0.9 mmol) and HOBt (0.9 mmol) in DMF before it was coupled to the peptide-resin. The synthesis cycle for the Fmoc amino acids included: (1) washing with NMP, (2) removing Fmoc protecting group with 20% piperidine in NMP for 30 min, (3) washing with NMP, and (4) coupling with pre-activated Fmoc amino acid for 1 h.

(ii) At the end of the assembly of the entire peptide chain, the protected peptide-resin was treated with a solution of 20% mercaptoethanol and 10% DIEA in DMF for 2×30 min to remove the DNP group on the side-chain of the His residue. The Mmt protecting group in the side-chain of the Cys residue was then removed by using a solution of 1% TFA and 5% TIS in DCM for 30 minutes and the peptide-resin was washed with DMF.

(iii) 1-(2-pyridyldithio)decane was prepared by stirring 2,2'-dipyridyl disulfide (1.06 g, 4.8 mmol), 1-decanethiol (0.83 mL, 4 mmol) and triethylamine (2 mL) in propanol and acetonitrile (⅓, v/v) at room temperature for about 3 hours (See Carlsson et al., *Biochem. J.*, 1978, 173, 723-737). Purification of the crude 1-(2-pyridyldithio)decane was performed using flash chromatography, eluting with a mixed solvent system of DCM/MeOH (10:0.4).

(iv) The peptide-resin from step (ii) was treated with the 1-(2-pyridyldithio)decane from step (iii) and DIEA (3 eq., 0.75 mmol) overnight in a mixed solvent system of DMF/1-propanol (7:3). The resin was then washed with DMF and the N-terminal Fmoc protecting group was removed by treatment with 25% piperidine in DMF for 30 min. The peptide-resin was then washed with DMF and DCM and dried under reduced pressure.

(v) Final cleavage was performed by stirring the peptide-resin in 10 mL of HF containing 1 mL anisole at about 0° C. for about 70 min. The purification procedure was the same as that described in Example 3. The target product (yield 10.2%) was found by analytical HPLC to have a purity of 99.9%. Electro-spray ionization mass spectrometry (ESI-MS) analysis gave the molecular weight at 3432.1 (in agreement with the calculated molecular weight of 3432.1).

Other peptides of the invention can be prepared by a person of ordinary skill in the art using synthetic procedures analogous to those disclosed generally hereinabove and/or to those disclosed specifically in the foregoing examples, as were the compounds depicted in Table 1.

nM, greater than about 100 nM, or greater than about 50 nM, using the Receptor Binding assay described below. With respect to $IC_{50}$, greater refers to potency and thus indicates a lesser amount is needed to achieve binding inhibition.

Assays measuring the ability of a compound to bind a GHS receptor employ a GHS receptor, a fragment of the receptor comprising a ghrelin binding site, a polypeptide comprising such a fragment, or a derivative of the polypeptide. Preferably, the assay uses the GHS receptor or a fragment thereof.

A polypeptide comprising a GHS receptor fragment that binds ghrelin can also contain one or more polypeptide regions not found in a GHS receptor. A derivative of such a polypeptide comprises a GHS receptor fragment that binds ghrelin along with one or more non-peptide components.

The GHS receptor amino acid sequence involved in ghrelin binding can be readily identified using labeled ghrelin or ghrelin analogs and different receptor fragments. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment

TABLE 1

| Compound | Purity (%) | Mass (ESI-MS) | Mass (Calc.) |
|---|---|---|---|
| (Asp$^3$(NH-hexyl))hGhrelin(1-28)-NH$_2$ | 99 | 3368.1 | 3368.92 |
| (Glu$^3$(NH-hexyl))hGhrelin(1-28)-NH$_2$ | 89 | 3368.52 | 3368.92 |
| (Aib$^1$)hGhrelin(1-28)-NH$_2$ | 98 | 3397.78 | 3397.96 |
| (Aib$^2$)hGhrelin(1-28)-NH$_2$ | 99 | 3367.92 | 3367.94 |
| (Glu$^3$(O-hexyl))hGhrelin(1-28)-NH$_2$ | 92.8 | 3369.17 | 3369.91 |
| (Asp$^3$(O-hexyl))hGhrelin(1-28)-NH$_2$ | 88.6 | 3369.92 | 3369.91 |
| (Cys$^3$(S(CH$_2$)$_9$CH$_3$)hGhrelin(1-28)-NH$_2$ | 100 | 3431.9 | 3432.11 |
| (Aib$^2$,Glu$^3$(NH-hexyl))hGhrelin(1-28)-NH$_2$ | 97 | 3367.24 | 3366.95 |
| (Aib$^{2,6}$)hGhrelin(1-28)-NH$_2$ | 95 | 3365.84 | 3365.96 |
| (Aib$^2$,Act$^6$)hGhrelin(1-28)-NH$_2$ | 95 | 3408.1 | 3408.00 |
| (A5c$^2$)hGhrelin(1-28)-NH$_2$ | 98 | 3393.47 | 3393.97 |
| (Act$^2$)hGhrelin(1-28)-NH$_2$ | 96 | 3409.14 | 3409.97 |
| (Aib$^2$,A6c$^5$)hGhrelin(1-28)-NH$_2$ | 99 | 3379.76 | 3379.95 |
| (A6c$^5$)hGhrelin(1-28)-NH$_2$ | 98.6 | 3381.72 | 3381.92 |
| (Aib$^2$,3Pal$^9$)Ghrelin(1-28)-NH$_2$ | 96.5 | 3378.3 | 3378.96 |
| (Dap$^3$(1-octanesulfonyl))hGhrelin(1-28)-NH$_2$ | 99 | 3418.7 | 3419.01 |
| (Aib$^2$,Thz$^7$)hGhrelin(1-28)-NH$_2$ | 97 | 3385.28 | 3385.98 |
| (Aib$^2$,Cha$^5$)hGhrelin(1-28)-NH$_2$ | 90 | 3408.8 | 3408.00 |
| (Aib$^2$,Abu$^6$)hGhrelin(1-28)-NH$_2$ | 90 | 3365.92 | 3365.96 |
| (Aib$^2$,4Hyp$^7$)hGhrelin(1-28)-NH$_2$ | 90 | 3383.7 | 3383.94 |
| (Aib$^2$,Taz$^9$)hGhrelin(1-28)-NH$_2$ | 95 | 3385.8 | 3384.99 |
| (Aib$^2$,4Pal$^9$)Ghrelin(1-28)-NH$_2$ | 95 | 3380.1 | 3378.96 |
| (Aib$^2$,Dhp$^7$)Ghrelin(1-28)-NH$_2$ | 95 | 3366.2 | 3365.92 |
| (Aib$^{2,8}$)Ghrelin(1-28)-NH$_2$ | 95 | 3324.0 | 3323.93 |
| (Aib$^2$,Pip$^7$)Ghrelin(1-28)-NH$_2$ | 99.9 | 3382.5 | 3381.96 |
| (Aib$^2$,Glu$^3$(NH-hexyl),4Hyp$^7$)Ghrelin(1-28)-NH$_2$ | 95 | 3382.7 | 3382.95 |
| (Aib$^{2,8}$,Glu$^3$(NH-hexyl))Ghrelin(1-28)-NH$_2$ | 95 | 3323.1 | 3322.94 |
| (Aib$^{2,12}$,Glu$^3$(NH-hexyl),4Pal$^9$,Orn$^{15}$)Ghrelin(1-28)-NH2 | 95 | 3321.9 | 3321.91 |
| (Aib$^2$,Glu$^3$(NH-hexyl),4Pal$^9$)Ghrelin(1-28)-NH$_2$ | 98.1 | 3378.4 | 3377.98 |
| (Aib$^2$,Glu$^3$(NH-hexyl),3Pal$^9$)Ghrelin(1-28)-NH$_2$ | 98.9 | 3378.2 | 3377.98 |
| (Aib$^{2,10}$)Ghrelin(1-28)-NH$_2$ | 99.0 | 3325.03 | 3324.91 |
| (Aib$^{2,10}$,Glu$^3$(NH-hexyl))Ghrelin(1-28)-NH$_2$ | 95.7 | 3324.05 | 3323.93 |
| (n-Octanoyl-Gly$^1$)hGhrelin(1-28)-NH$_2$ | 95 |  | 3496.11 |

Biological Assay

The activity of the compounds of the invention at the GHS receptor can be and were determined using techniques such as those described in the examples provided below. In different embodiments a ghrelin analog has at least about 50%, at least about 60%, at least about 70%, at least about 80%, or at least about 90%, functional activity relative to ghrelin as determined using one or more of the Functional Activity assays described below; and/or has an $IC_{50}$ greater than about 1,000 binding ghrelin can be subdivided to further locate the ghrelin binding region. Fragments used for binding studies can be generated using recombinant nucleic acid techniques.

Binding assays can be performed using individual compounds or preparations containing different numbers of compounds. A preparation containing different numbers of compounds having the ability to bind to the GHS receptor can be divided into smaller groups of compounds that can be tested to identify the compound(s) binding to the GHS receptor. In an embodiment of the present invention, a test preparation containing at least 10 compounds is used in a binding assay.

Binding assays can be performed using recombinantly produced GHS receptor polypeptides present in different environments. Such environments include, for example, cell extracts and purified cell extracts containing the GHS receptor polypeptide expressed from recombinant nucleic acid or naturally occurring nucleic acid; and also include, for example, the use of a purified GHS receptor polypeptide produced by recombinant means or from naturally occurring nucleic acid which is introduced into a different environment.

Screening for GHS Receptor Active Compounds

Screening for GHS receptor active compounds is facilitated using a recombinantly expressed receptor. Using a recombinantly expressed GHS receptor offers several advantages such as the ability to express the receptor in a defined cell system so that a response to a compound at the GHS receptor can more readily be differentiated from responses at other receptors. For example, the GHS receptor can be expressed in a cell line such as HEK 293, COS 7, and CHO not normally expressing the receptor by an expression vector, wherein the same cell line without the expression vector can act as a control.

Screening for compounds reducing GHS receptor activity is facilitated through the use of a ghrelin analog in the assay. The use of a ghrelin analog in a screening assay provides for GHS receptor activity. The effect of test compounds on such activity can be measured to identify, for example, allosteric modulators and antagonists.

GHS receptor activity can be measured using different techniques such as detecting a change in the intracellular conformation of the GHS receptor, in the G-protein coupled activities, and/or in the intracellular messengers. Preferably, GHS receptor activity is measured using techniques such as those measuring intracellular $Ca^{2+}$ Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17 (Button et al., *Cell Calcium*, 1993. 14, 663-671, and Feighner et al., *Science*, 1999, 284, 2184-2188).

Chimeric receptors containing a ghrelin binding region functionally coupled to a different G-protein can also be used to measure GHS receptor activity. A chimeric GHS receptor contains an N-terminal extracellular domain; a transmembrane domain made up of transmembrane regions, extracellular loop regions, and intracellular loop regions; and an intracellular carboxy terminus. Techniques for producing chimeric receptors and measuring G-protein coupled responses are provided in, for example, International Application Number WO 97/05252, and U.S. Pat. No. 5,264,565, both of which are hereby incorporated by reference herein.

Stimulation of GHS Receptor Activity

Ghrelin analogs can be used to stimulate GHS receptor activity. Such stimulation can be used, for example, to study the effect of GHS receptor modulation, to study the effect of growth hormone secretion, to look for or study ghrelin antagonists, or to achieve a beneficial effect in a subject. Beneficial effects that can be achieved include one or more of the following: treating a growth hormone deficient state, increasing muscle mass, increasing bone density, treating sexual dysfunction in males or females, facilitating a weight gain, facilitating maintenance of weight, facilitating maintenance of physical functioning, facilitating recovery of physical function, and/or facilitating appetite increase.

Increasing weight or appetite can be useful for maintaining weight or producing a weight or appetite gain in an under weight subject, or in a patient having a disease or undergoing treatment that affects weight or appetite. In addition, for example, farm animals such as pigs, cows and chickens can be treated to gain weight.

Underweight subjects include those having a body weight about 10% or less, 20% or less, or 30% or less, than the lower end of a "normal" weight range or Body Mass Index ("BMI"). "Normal" weight ranges are well known in the art and take into account factors such as a patient age, height, and body type.

BMI measures your height/weight ratio. It is determined by calculating weight in kilograms divided by the square of height in meters. The BMI "normal" range is 19-22.

Example 5

Receptor Binding Assay

A. Preparation of CHO-K1 cells expressing the human recombinant GHS receptor

The cDNA for human growth hormone secretagogue receptor (hGHS-R1a, or ghrelin receptor) was cloned by Polymerase Chain Reaction (PCR) using human brain RNA as a template (Clontech, Palo Alto, Calif.), gene specific primers flanking the full-length coding sequence of hGHS-R, (S: 5'-A T G T G G A A C G C G A C G C C C A G C G A A G A G-3' (SEQ ID NO:149) and AS: 5'-T C A T G T A T T A A T A C T A G A T T C T G T C C A-3') (SEQ ID NO:150), and Advantage 2 PCR Kit (Clontech). The PCR product was cloned into the pCR2.1 vector using Original TA Cloning Kit (Invitrogen, Carlsbad, Calif.). The full length human GHS-R was subcloned into the mammalian expression vector pcDNA 3.1 (Invitrogen). The plasmid was transfected into the Chinese hamster ovary cell line, CHO-K1 (American Type Culture Collection, Rockville, Md.), by calcium phosphate method (Wigler, M et al., Cell 11, 223, 1977). Single cell clones stably expressing the hGHS-R were obtained by selecting transfected cells grown in cloning rings in RPMI 1640 media supplemented with 10% fetal bovine serum and 1 mM sodium pyruvate containing 0.8 mg/ml G418 (Gibco, Grand Island, N.Y.).

B. GHS-R Binding Assay:

Membranes for radioligand binding studies can be and were prepared by homogenization of the foregoing CHO-K1 cells expressing the human recombinant GHS receptor in 20 ml of ice-cold 50 mM Tris-HCl with a Brinkman Polytron (Westbury, N.Y.) (setting 6, 15 sec). The homogenates were washed twice by centrifugation (39,000 g/10 min), and the final pellets were resuspended in 50 mM Tris-HCl, containing 2.5 mM $MgCl_2$, and 0.1% BSA. For assay, aliquots (0.4 ml) were incubated with 0.05 nM ($^{125}$I)ghrelin (~2000 Ci/mmol, Perkin Elmer Life Sciences, Boston, Mass.), with and without 0.05 ml of unlabeled competing test peptides. After a 60 min incubation (4° C.), the bound ($^{125}$I)ghrelin was separated from the free by rapid filtration through GF/C filters (Brandel, Gaithersburg, Md.), which had been previously soaked in 0.5% polyethyleneimine/0.1% BSA. The filters were then washed three times with 5-ml aliquots of ice-cold 50 mM Tris-HCl and 0.1% bovine serum albumin, and the bound radioactivity trapped on the filters was counted by gamma spectrometry (Wallac LKB, Gaithersburg, Md.). Specific binding was defined as the total ($^{125}$I)ghrelin bound minus that bound in the presence of 1000 nM ghrelin (Bachem, Torrence, Calif.).

Example 6

GHS-R Functional Activity Assays

A. In vitro GSH Receptor Mediated Intracellular $iCa^{2+}$ Mobilization

The foregoing CHO-K1 cells expressing the human GSH receptor were harvested by incubating in a 0.3% EDTA/phosphate buffered saline solution (25° C.), and washed twice by centrifugation. The washed cells were resuspended in Hank's-buffered saline solution (HBSS) for loading of the fluorescent $Ca^{2+}$ indicator Fura-2AM. Cell suspensions of approximately $10^6$ cells/ml were incubated with 2 μM Fura-2AM for 30 min at about 25° C. Unloaded Fura-2AM was removed by centrifugation twice in HBBS, and the final suspensions were transferred to a spectrofluorometer (Hitachi F-2000) equipped with a magnetic stirring mechanism and a temperature-regulated cuvette holder. After equilibration to 37° C., the ghrelin analogs were added for measurement of intracellular $Ca^{2+}$ mobilization. The excitation and emission wavelengths were 340 and 510 nm, respectively.

B. In Vivo GH Release/Suppression

As is well known in the art, compounds may be tested for their ability to stimulate or suppress release of growth hormone (GH) in vivo (see, e.g., Deghenghi, R., et al., *Life Sciences,* 1994, 54, 1321-1328; International Application No. WO 02/08250). Thus, for example, in order to ascertain a compound's ability to stimulate GH release in vivo the compound may be injected subcutaneously in 10-day old rats at a dose of, e.g., 300 mg/kg. The circulating GH may be determined at, e.g., 15 minutes after injection and compared to GH levels in rats injected with a solvent control.

Similarly, compounds may be tested for their ability to antagonize ghrelin-induced GH secretion in vivo. Thus a compound may be injected subcutaneously in 10-day old rats at a dose of, e.g., 300 mg/kg, along with ghrelin. Again the circulating GH may be determined at, e.g., 15 minutes after injection and compared to GH levels in rats injected with ghrelin alone.

Administration

Ghrelin analogs can be formulated and administered to a subject using the guidance provided herein along with techniques well known in the art. The preferred route of administration ensures that an effective amount of compound reaches the target. Guidelines for pharmaceutical administration in general are provided in, for example, *Remington: The Science and Practice of Pharmacy* $20^{th}$ *Edition*, Ed. Gennaro, Lippincott, Williams & Wilkins Publishing, 2000, and *Modem Pharmaceutics* $2^{nd}$ *Edition*, Eds. Banker and Rhodes, Marcel Dekker, Inc., 1990, both of which are hereby incorporated by reference herein.

Ghrelin analogs can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

Ghrelin analogs can be administered using different routes including oral, nasal, by injection, transdermal, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

Administered by nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

Ghrelin analogs may also be administered in intravenous (both bolus and infusion), intraperitoneal, subcutaneous, topical with or without occlusion, or intramuscular form. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

Ghrelin analogs can be provided in a kit. Such a kit typically contains an active compound in dosage forms for administration. A dosage form contains a sufficient amount of active compound such that a desirable effect can be obtained when administered to a subject during regular intervals, such as 1 to 6 times a day, during the course of 1 or more days. Preferably, a kit contains instructions indicating the use of the dosage form to achieve a desirable affect and the amount of dosage form to be taken over a specified time period.

The invention has been described in an illustrative manner, and it is to be understood that the terminology which has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

The patent and scientific literature referred to herein represents knowledge that is available to those with skill in the art. All patents, patent publications and other publications cited herein are hereby incorporated by reference in their entirety.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A compound according to formula (I):

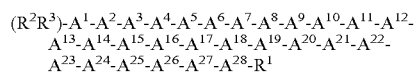

(I), or a pharmaceutically acceptable salt thereof, wherein:

$A^1$ is Gly, Aib, Ala, β-Ala, or Acc;

$A^2$ is Ser, Aib, Act, Ala, Acc, Abu, Ava, Thr, or Val;

$A^3$ is Ser, Ser(C(O)—$R^4$), Asp(O—$R^8$), Asp(NH—$R^9$), Dap(S(O)$_2$—$R^{10}$), Dab(S(O)$_2$—$R^{11}$), Glu(O—$R^6$), Glu(NH—$R^7$), Thr, Thr(C(O)—$R^5$), or HN—CH((CH$_2$)$_n$—N($R^{12}R^{13}$))—C(O);

43

A⁴ is Phe, Acc, Aic, Cha, 2Fua, 1Nal, 2Nal, 2Pal, 3Pal, 4Pal, hPhe, (X¹, X², X³, X⁴, X⁵)Phe, Taz, 2Thi, 3Thi, Trp, or Tyr;

A⁵ is Leu, Abu, Acc, Aib, Ala, Cha, Ile, hLeu, Nle, Nva, Phe, Tle, or Val;

A⁶ is Ser, Abu, Acc, Act, Aib, Ala, Gly, Thr, or Val;

A⁷ is Pro, Dhp, Dmt, 3Hyp, 4Hyp, Inc, Ktp, Oic, Pip, Thz, Tic, or deleted;

A⁸ is Glu, Acc, Aib, Asn, Asp, Dab, Dap, Gln, Lys, Orn, HN—CH((CH₂)ₙ—N(R¹²R¹³))—C(O), or deleted;

A⁹ is His, Apc, Aib, Acc, 2Fua, 2Pal, 3Pal, 4Pal, Taz, 2Thi, 3Thi, (X¹, X², X³, X⁴, X⁵-)Phe or deleted;

A¹⁰ is Gln, Acc, Aib, Asn, Asp, Glu, or deleted;

A¹¹ is Arg, Apc, hArg, Dab, Dap, Lys, Orn, HN—CH((CH₂)ₙ—N(R¹²R¹³))—C(O), or deleted;

A¹² is Val, Abu, Acc, Aib, Ala, Cha, Nva, Gly, Ile, Leu, Nle, Tle, Cha, or deleted;

A¹³ is Gln, Acc, Aib, Asn, Asp, Glu, or deleted;

A¹⁴ is Gln, Acc, Aib, Asn, Asp, Glu, or deleted;

A¹⁵ is Arg, hArg, Acc, Aib, Apc, Dab, Dap, Lys, Orn, HN—CH((CH₂)ₙ—N(R¹²R¹³))—C(O), or deleted;

A¹⁶ is Lys, Acc, Aib, Apc, Arg, hArg, Dab, Dap, Orn, HN—CH((CH₂)ₙ—N(R¹²R¹³))—C(O), or deleted;

A¹⁷ is Glu, Arg, Asn, Asp, Dab, Dap, Gln, Lys, Orn, HN—CH((CH₂)ₙ—N(R¹²R¹³))—C(O), or deleted;

A¹⁸ is Ser, Abu, Acc, Act, Aib, Ala, Thr, Val, or deleted;

A¹⁹ is Lys, Acc, Aib, Apc, Arg, hArg, Dab, Dap, Orn, HN—CH((CH₂)ₙ—N(R¹²R¹³))—C(O), or deleted;

A²⁰ is Lys, Acc, Aib, Apc, Arg, hArg, Dab, Dap, Orn, HN—CH((CH₂)ₙ—N(R¹²R¹³))—C(O), or deleted;

A²¹ is Pro, Dhp, Dmt, Inc, 3Hyp, 4Hyp, Ktp, Oic, Pip, Thz, Tic, or deleted;

A²² is Pro, Dhp, Dmt, 3Hyp, 4Hyp, Inc, Ktp, Oic, Pip, Thz, Tic, or deleted;

A²³ is Abu, Acc, Act, Aib, Ala, Apc, Gly, Nva, Val, or deleted;

A²⁴ is Lys, Acc, Aib, Apc, Arg, hArg, Dab, Dap, Orn, HN—CH((CH₂)ₙ—N(R¹²R¹³))—C(O), or deleted;

A²⁵ is Leu, Abu, Acc, Aib, Ala, Cha, Ile, hLeu, Nle, Nva, Phe, Tle, Val, or deleted;

A²⁶ is Gln, Aib, Asn, Asp, Glu, or deleted;

A²⁷ is Pro, Dhp, Dmt, 3Hyp, 4Hyp, Inc, Ktp, Oic, Pip, Thz, Tic, or deleted;

A²⁸ is Acc, Aib, Apc, Arg, hArg, Dab, Dap, Lys, Orn, HN—CH((CH₂)ₙ—N(R¹²R¹³))—C(O), or deleted;

R¹ is —OH, —NH₂, —(C₁-C₃₀)alkoxy, or NH—X⁶—CH₂-Z⁰, wherein X⁶ is a (C₁-C₁₂)alkyl, (C₂-C₁₂)alkenyl, and Z⁰ is —H, —OH, —CO₂H or —C(O)—NH₂;

R² and R³ each is, independently for each occurrence, H, (C₁-C₂₀)alkyl or (C₁-C₂₀)acyl;

R⁴, R⁵, R⁶, R⁷, R⁸, R⁹, R¹⁰ and R¹¹ each is, independently for each occurrence, (C₁-C₄₀)alkyl, (C₂-C₄₀)alkenyl, substituted (C₁-C₄₀) alkyl, substituted (C₂-C₄₀) alkenyl, alkylaryl, substituted alklyaryl, aryl or substituted aryl;

R¹² and R¹³ each is, independently for each occurrence, H, (C₁-C₄₀)alkyl, (C₁-C₄₀)acyl, (C₁-C₃₀)alkylsulfonyl, or —C(NH)—NH₂, wherein when R¹² is (C₁-C₄₀)acyl, (C₁-C₃₀)alkylsulfonyl, or —C(NH)—NH₂, then R¹³ is H or (C₁-C₄₀)alkyl;

n is, independently for each occurrence, 1, 2, 3, 4, or 5;

X¹, X², X³, X⁴, and X⁵ each is, independently for each occurrence, H, F, Cl, Br, I, (C₁₋₁₀)alkyl, substituted (C₁₋₁₀)alkyl, aryl, substituted aryl, OH, NH₂, NO₂, or CN;

44 provided that the peptide contains at least one amino acid selected from the groups consisting of:

A² is Aib, Acc, or Act;

A³ is Dap(S(O)₂—R¹⁰), Dab(S(O)₂—R¹¹), or Glu(NH-Hexyl);

A⁵ is Abu, Acc, Aib, Cha, hLeu, Nle, Nva, or Tle;

A⁶ is Abu, Acc, Act, or Aib;

A⁷ is Dhp, Dmt, 3Hyp, 4Hyp, Inc, Ktp, Oic, Pip, Thz or Tic;

A⁸ is Acc, Aib, Asn, Asp, Dab, Dap, Orn, or HN—CH((CH₂)ₙ—N(R¹²R¹³))—C(O);

A⁹ is Aib, Acc, Apc, 2Fua, 2Pal, 3Pal, 4Pal, Taz, 2Thi, 3Thi, or (X¹, X², X³, X⁴, X⁵-)Phe; and A¹⁰ is Acc or Aib;

and further provided that the peptide is not (Lys⁸)hGhrelin(1-8)-NH₂ or (Arg⁸)hGhrelin(1-8)-NH₂.

2. The compound of claim 1, wherein

A¹ is Gly or Aib;

A² is Ser, Aib, A5c, Act, or Ava;

A³ is Ser(C(O)—R⁴), Glu(O—R⁶), Glu(NH—R⁷), Dap(S(O)₂—R¹⁰), or Dab(S(O)₂—R¹¹);

A⁴ is Phe;

A⁵ is Leu, Acc, Aib, Cha, or hLeu;

A⁶ is Ser, Abu, Act, Aib, or Thr;

A⁷ is Pro, Dhp, Dmt, 4Hyp, Ktp, Pip, Tic, or Thz;

A⁸ is Glu or Aib;

A⁹ is His, Aib, Apc, 2Fua, 2Pal, 3Pal, 4Pal, Taz, or 2Thi;

A¹⁰ is Gln or Aib;

A¹¹ is Arg;

A¹² is Aib, Val or Acc;

A¹³ is Gln;

A¹⁴ is Gln;

A¹⁵ is Arg or Orn;

A¹⁶ is Lys or Apc;

A¹⁷ is Glu;

A¹⁸ is Ser;

A¹⁹ is Lys;

A²⁰ is Lys;

A²¹ is Pro;

A²² is Pro;

A²³ is Ala;

A²⁴ is Lys;

A²⁵ is Leu;

A²⁶ is Gln;

A²⁷ is Pro; and

A²⁸ is Arg;

or a pharmaceutically acceptable salt thereof.

3. The compound of claim 2, wherein

R² and R³ each is, independently, H, Acyl, n-butyryl, isobutyryl, or n-octanoyl;

R⁴ is octyl;

R⁶ is hexyl;

R⁷ is hexyl;

R¹⁰ is octyl; and

R¹¹ is octyl, wherein

Acc is, independently for each occurrence, A5c or A6c;

or a pharmaceutically acceptable salt thereof.

4. The compound of claim 3, selected from:

(Dap³(Octanesulfonyl))hGhrelin(1-28)-NH₂; (SEQ ID NO:1)

(Aib², A6c⁵)hGhrelin(1-28)-NH₂; (SEQ ID NO:2)

(A6c⁵)hGhrelin(1-28)-NH₂; (SEQ ID NO:3)

(Aib²,⁶)hGhrelin(1-28)-NH₂; (SEQ ID NO:4)

(Aib², A5c¹²)hGhrelin(1-28)-NH₂; (SEQ ID NO:5)

(Aib², A5c¹², Orn¹⁵)hGhrelin(1-28)-NH₂; (SEQ ID NO:6)

(Aib², A5c¹², Apc¹⁶)hGhrelin(1-28)-NH₂; (SEQ ID NO:7)

(Aib², Act⁶)hGhrelin(1-28)-NH₂; (SEQ ID NO:4)

(Aib², 3Pal⁹)hGhrelin(1-28)-NH₂; (SEQ ID NO:8)

(Aib², Dmt⁷)hGhrelin(1-28)-NH₂; (SEQ ID NO:9)
(Aib², Thz⁷)hGhrelin(1-28)-NH₂; (SEQ ID NO:9)
(A5c²)hGhrelin(1-28)-NH₂; (SEQ ID NO:10)
(Act²)hGhrelin(1-28)-NH₂; (SEQ ID NO:10)
(Aib², A5c⁵)hGhrelin(1-28)-NH₂; (SEQ ID NO:2)
(Aib², A6c⁵)hGhrelin(1-28)-NH₂; (SEQ ID NO:2)
(Aib²,⁵)hGhrelin(1-28)-NH₂; (SEQ ID NO:2)
(Aib², hLeu⁵)hGhrelin(1-28)-NH₂; (SEQ ID NO:2)
(Aib², Cha⁵)hGhrelin(1-28)-NH₂; (SEQ ID NO:2)
(Aib²,⁶)hGhrelin(1-28)-NH₂; (SEQ ID NO:4)
(Aib², Act⁶)hGhrelin(1-28)-NH₂; (SEQ ID NO:4)
(Aib², Thr⁶)hGhrelin(1-28)-NH₂; (SEQ ID NO:4)
(Aib², Abu⁶)hGhrelin(1-28)-NH₂; (SEQ ID NO:4)
(Aib², 4Hyp⁷)hGhrelin(1-28)-NH₂; (SEQ ID NO:9)
(Aib²,Thz⁷)hGhrelin(1-28)-NH₂; (SEQ ID NO:9)
(Aib², Pip⁷)hGhrelin(1-28)-NH₂; (SEQ ID NO:9)
(Aib², Dhp⁷)hGhrelin(1-28)-NH₂; (SEQ ID NO:9)
(Aib², Ktp⁷)hGhrelin(1-28)-NH₂; (SEQ ID NO:9)
(Aib²,⁸)hGhrelin(1-28)-NH₂; (SEQ ID NO:11)
(Aib², 2Pal⁹)hGhrelin(1-28)-NH₂; (SEQ ID NO:8)
(Aib², 3Pal⁹)hGhrelin(1-28)-NH₂; (SEQ ID NO:8)
(Aib², 4Pal⁹)hGhrelin(1-28)-NH₂; (SEQ ID NO:8)
(Aib², Taz⁹)hGhrelin(1-28)-NH₂; (SEQ ID NO:8)
(Aib², 2Thi⁹)hGhrelin(1-28)-NH₂; (SEQ ID NO:8)
(Aib², 2Fua⁹)hGhrelin(1-28)-NH₂; (SEQ ID NO:8)
(Aib², Apc⁹)hGhrelin(1-28)-NH₂; (SEQ ID NO:8)
(Aib²,⁹)hGhrelin(1-28)-NH₂; (SEQ ID NO:8)
(Aib²,¹⁰)hGhrelin(1-28)-NH₂; (SEQ ID NO:12)
(Aib², Tic⁷)hGhrelin(1-28)-NH₂; (SEQ ID NO:9)
(Aib⁶)hGhrelin(1-28)-NH₂; (SEQ ID NO:13)
(A5c⁵)hGhrelin(1-28)-NH₂; (SEQ ID NO:3)
(A6c⁵)hGhrelin(1-28)-NH₂; (SEQ ID NO:3)
(Act⁶)hGhrelin(1-28)-NH₂; (SEQ ID NO:13)
(3Pal⁹)hGhrelin(1-28)-NH₂; (SEQ ID NO:14)
(Dmt⁷)hGhrelin(1-28)-NH₂; (SEQ ID NO:15)
(Thz⁷)hGhrelin(1-28)-NH₂; (SEQ ID NO:15)
(Aib⁵)hGhrelin(1-28)-NH₂; (SEQ ID NO:3)
(hLeu⁵)hGhrelin(1-28)-NH₂; (SEQ ID NO:3)
(Cha⁵)hGhrelin(1-28)-NH₂; (SEQ ID NO:3)
(Abu⁶)hGhrelin(1-28)-NH₂; (SEQ ID NO:13)
(4Hyp⁷)hGhrelin(1-28)-NH₂; (SEQ ID NO:15)
(Pip⁷)hGhrelin(1-28)-NH₂; (SEQ ID NO:15)
(Dhp⁷)hGhrelin(1-28)-NH₂; (SEQ ID NO:15)
(Ktp⁷)hGhrelin(1-28)-NH₂; (SEQ ID NO:15)
(Aib⁸)hGhrelin(1-28)-NH₂; (SEQ ID NO:16)
(2Pal⁹)hGhrelin(1-28)-NH₂; (SEQ ID NO:14)
(3Pal⁹)hGhrelin(1-28)-NH₂; (SEQ ID NO:14)
(4Pal⁹)hGhrelin(1-28)-NH₂; (SEQ ID NO:14)
(Taz⁹)hGhrelin(1-28)-NH₂; (SEQ ID NO:14)
(2Thi⁹)hGhrelin(1-28)-NH₂; (SEQ ID NO:14)
(2Fua⁹)hGhrelin(1-28)-NH₂; (SEQ ID NO:14)
(Apc⁹)hGhrelin(1-28)-NH₂; (SEQ ID NO:14)
(Aib⁹)hGhrelin(1-28)-NH₂; (SEQ ID NO:14)
(Aib¹⁰)hGhrelin(1-28)-NH₂; (SEQ ID NO:17)
(Aib², Dap³(Octanesulfonyl), A6c⁵)hGhrelin(1-28)-NH₂; (SEQ ID NO:18)
(Dap³(Octanesulfonyl), A6c⁵)hGhrelin(1-28)-NH₂; (SEQ ID NO:19)
(Aib²,⁶, Dap³(Octanesulfonyl))hGhrelin(1-28)-NH₂; (SEQ ID NO:67)
(Aib², Dap³(Octanesulfonyl), A5c¹²)hGhrelin(1-28)-NH₂; (SEQ ID NO:68)
(Aib², Dap³(Octanesulfonyl), A5c¹², Orn¹⁵)hGhrelin(1-28)-NH₂; (SEQ ID NO:69)
(Aib², Dap³(Octanesulfonyl), A5c¹², Apc¹⁶)hGhrelin(1-28)-NH₂; (SEQ ID NO:23)
(Aib², Dap³(Octanesulfonyl), Act⁶)hGhrelin(1-28)-NH₂; (SEQ ID NO:20)
(Aib², Dap³(Octanesulfonyl), 3Pal⁹)hGhrelin(1-28)-NH₂; (SEQ ID NO:24)
(Aib², Dap³(Octanesulfonyl), Dmt⁷)hGhrelin(1-28)-NH₂; (SEQ ID NO:25)
(Aib², Dap³(Octanesulfonyl), Thz⁷)hGhrelin(1-28)-NH₂; (SEQ ID NO:25)
(A5c², Dap³(Octanesulfonyl))hGhrelin(1-28)-NH₂; (SEQ ID NO:26)
(Act², Dap³(Octanesulfonyl))hGhrelin(1-28)-NH₂; (SEQ ID NO:26)
(Aib², Dap³(Octanesulfonyl), A5c⁵)hGhrelin(1-28)-NH₂; (SEQ ID NO:27)
(Aib²,⁵, Dap³(Octanesulfonyl))hGhrelin(1-28)-NH₂; (SEQ ID NO:27)
(Aib², Dap³(Octanesulfonyl), hLeu⁵)hGhrelin(1-28)-NH₂; (SEQ ID NO:27)
(Aib², Dap³(Octanesulfonyl), Cha⁵)hGhrelin(1-28)-NH₂; (SEQ ID NO:27)
(Aib²,⁶, Dap³(Octanesulfonyl))hGhrelin(1-28)-NH₂; (SEQ ID NO:20)
(Aib², Dap³(Octanesulfonyl), Thr⁶)hGhrelin(1-28)-NH₂; (SEQ ID NO:20)
(Aib², Dap³(Octanesulfonyl), Abu⁶)hGhrelin(1-28)-NH₂; (SEQ ID NO:20)
(Aib², Dap³(Octanesulfonyl), 4Hyp⁷)hGhrelin(1-28)-NH₂; (SEQ ID NO:25)
(Aib², Dap³(Octanesulfonyl), Pip⁷)hGhrelin(1-28)-NH₂; (SEQ ID NO:25)
(Aib², Dap³(Octanesulfonyl), Dhp⁷)hGhrelin(1-28)-NH₂; (SEQ ID NO:25)
(Aib², Dap³(Octanesulfonyl), Ktp⁷)hGhrelin(1-28)-NH₂; (SEQ ID NO:25)
(Aib²,⁸, Dap³(Octanesulfonyl))hGhrelin(1-28)-NH₂; (SEQ ID NO:28)
(Aib², Dap³(Octanesulfonyl), 2Pal⁹)hGhrelin(1-28)-NH₂; (SEQ ID NO:24)
(Aib², Dap³(Octanesulfonyl), 3Pal⁹)hGhrelin(1-28)-NH₂; (SEQ ID NO:24)
(Aib², Dap³(Octanesulfonyl), 4Pal⁹)hGhrelin(1-28)-NH₂; (SEQ ID NO:24)
(Aib², Dap³(Octanesulfonyl), Taz⁹)hGhrelin(1-28)-NH₂; (SEQ ID NO:24)
(Aib², Dap³(Octanesulfonyl), 2Thi⁹)hGhrelin(1-28)-NH₂; (SEQ ID NO:24)
(Aib², Dap³(Octanesulfonyl), 2Fua⁹)hGhrelin(1-28)-NH₂; (SEQ ID NO:24)
(Aib², Dap³(Octanesulfonyl), Apc⁹)hGhrelin(1-28)-NH₂; (SEQ ID NO:24)
(Aib²,⁹, Dap³(Octanesulfonyl))hGhrelin(1-28)-NH₂; (SEQ ID NO:24)
(Aib²,¹⁰, Dap³(Octanesulfonyl))hGhrelin(1-28)-NH₂; (SEQ ID NO:29)
(Dap³(Octanesulfonyl), A6c⁵)hGhrelin(1-28)-NH₂; (SEQ ID NO:19)
(Dap³(Octanesulfonyl), Aib⁶)hGhrelin(1-28)-NH₂; (SEQ ID NO:30)
(Dap³(Octanesulfonyl), A5c¹²)hGhrelin(1-28)-NH₂; (SEQ ID NO:31)
(Dap³(Octanesulfonyl), A5c¹²,Orn¹⁵)hGhrelin(1-28)-NH₂; (SEQ ID NO:32)
(Dap³(Octanesulfonyl), A5c¹²,Apc¹⁶)hGhrelin(1-28)-NH₂; (SEQ ID NO:33)
(Dap³(Octanesulfonyl), Act⁶)hGhrelin(1-28)-NH₂; (SEQ ID NO:30)

(Dap³(Octanesulfonyl), 3Pal⁹)hGhrelin(1-28)-NH₂; (SEQ ID NO:34)
(Dap³(Octanesulfonyl), Dmt⁷)hGhrelin(1-28)-NH₂; (SEQ ID NO:35)
(Dap³(Octanesulfonyl), Thz⁷)hGhrelin(1-28)-NH₂; (SEQ ID NO:35)
(Dap³(Octanesulfonyl), A5c⁵)hGhrelin(1-28)-NH₂; (SEQ ID NO:19)
(Dap³(Octanesulfonyl), Aib⁵)hGhrelin(1-28)-NH₂; (SEQ ID NO:19)
(Dap³(Octanesulfonyl), hLeu⁵)hGhrelin(1-28)-NH₂; (SEQ ID NO:19)
(Dap³(Octanesulfonyl), Cha⁵)hGhrelin(1-28)-NH₂; (SEQ ID NO:19)
(Dap³(Octanesulfonyl), Thr⁶)hGhrelin(1-28)-NH₂; (SEQ ID NO:30)
(Dap³(Octanesulfonyl), Abu⁶)hGhrelin(1-28)-NH₂; (SEQ ID NO:30)
(Dap³(Octanesulfonyl), 4Hyp⁷)hGhrelin(1-28)-NH₂; (SEQ ID NO:35)
(Dap³(Octanesulfonyl), Pip⁷)hGhrelin(1-28)-NH₂; (SEQ ID NO:35)
(Dap³(Octanesulfonyl), Dhp⁷)hGhrelin(1-28)-NH₂; (SEQ ID NO:35)
(Dap³(Octanesulfonyl), Ktp⁷)hGhrelin(1-28)-NH₂; (SEQ ID NO:35)
(Dap³(Octanesulfonyl), Aib⁸)hGhrelin(1-28)-NH₂; (SEQ ID NO:36)
(Dap³(Octanesulfonyl), 2Pal⁹)hGhrelin(1-28)-NH₂; (SEQ ID NO:34)
(Dap³(Octanesulfonyl), 3Pal⁹)hGhrelin(1-28)-NH₂; (SEQ ID NO:34)
(Dap³(Octanesulfonyl), 4Pal⁹)hGhrelin(1-28)-NH₂; (SEQ ID NO:34)
(Dap³(Octanesulfonyl), Taz⁹)hGhrelin(1-28)-NH₂; (SEQ ID NO:34)
(Dap³(Octanesulfonyl), 2Thi⁹)hGhrelin(1-28)-NH₂; (SEQ ID NO:34)
(Dap³(Octanesulfonyl), 2Fua⁹)hGhrelin(1-28)-NH₂; (SEQ ID NO:34)
(Dap³(Octanesulfonyl), Apc⁹)hGhrelin(1-28)-NH₂; (SEQ ID NO:34)
(Dap³(Octanesulfonyl), Aib⁹)hGhrelin(1-28)-NH₂; (SEQ ID NO:34)
(Dap³(Octanesulfonyl), Aib¹⁰)hGhrelin(1-28)-NH₂; (SEQ ID NO:37)
(Dap³(Octanesulfonyl), A5c¹², Orn¹⁵)hGhrelin(1-28)-NH₂; (SEQ ID NO:32)
(Dab³(Octanesulfonyl), A5c¹², Orn¹⁵)hGhrelin(1-28)-NH₂; (SEQ ID NO:32)
(Aib², A6c⁵, A5c¹², Orn¹⁵)hGhrelin(1-28)-NH₂; (SEQ ID NO:38)
(A6c⁵, A5c¹², Orn¹⁵)hGhrelin(1-28)-NH₂; (SEQ ID NO:39)
(Aib², Act⁶, A5c¹², Orn¹⁵)hGhrelin(1-28)-NH₂; (SEQ ID NO:40)
(Aib², Act⁶, A5c¹², Orn¹⁵)hGhrelin(1-28)-NH₂; (SEQ ID NO:40)
(Aib², 3Pal⁹, A5c¹², Orn¹⁵)hGhrelin(1-28)-NH₂; (SEQ ID NO:41)
(Aib², Dmt⁷, A5c¹², Orn¹⁵)hGhrelin(1-28)-NH₂; (SEQ ID NO:42)
(Aib², Thz⁷, A5c¹², Orn¹⁵)hGhrelin(1-28)-NH₂; (SEQ ID NO:42)
(Aib², A5c⁵, A5c¹², Orn¹⁵)hGhrelin(1-28)-NH₂; (SEQ ID NO:38)
(Aib²,⁵, A5c¹², Orn¹⁵)hGhrelin(1-28)-NH₂; (SEQ ID NO:38)
(Aib², hLeu⁵, A5c¹², Orn¹⁵)hGhrelin(1-28)-NH₂; (SEQ ID NO:38)
(Aib², Cha⁵, A5c¹², Orn¹⁵)hGhrelin(1-28)-NH₂; (SEQ ID NO:38)
(Aib²,⁶, A5c¹², Orn¹⁵)hGhrelin(1-28)-NH₂; (SEQ ID NO:40)
(Aib², Thr⁶, A5c¹², Orn¹⁵)hGhrelin(1-28)-NH₂; (SEQ ID NO:40)
(Aib², Abu⁶, A5c¹², Orn¹⁵)hGhrelin(1-28)-NH₂; (SEQ ID NO:40)
(Aib², 4Hyp⁷, A5c¹², Orn¹⁵)hGhrelin(1-28)-NH₂; (SEQ ID NO:42)
(Aib², Pip⁷, A5c¹², Orn¹⁵)hGhrelin(1-28)-NH₂; (SEQ ID NO:42)
(Aib², Dhp⁷, A5c¹², Orn¹⁵)hGhrelin(1-28)-NH₂; (SEQ ID NO:42)
(Aib², Ktp⁷, A5c¹², Orn¹⁵)hGhrelin(1-28)-NH₂; (SEQ ID NO:42)
(Aib²,⁸, A5c¹², Orn¹⁵)hGhrelin(1-28)-NH₂; (SEQ ID NO:43)
(Aib², 2Pal⁹, A5c¹², Orn¹⁵)hGhrelin(1-28)-NH₂; (SEQ ID NO:41)
(Aib², 3Pal⁹, A5c¹², Orn¹⁵)hGhrelin(1-28)-NH₂; (SEQ ID NO:41)
(Aib², 4Pal⁹, A5c¹², Orn¹⁵)hGhrelin(1-28)-NH₂; (SEQ ID NO:41)
(Aib², Taz⁹, A5c¹², Orn¹⁵)hGhrelin(1-28)-NH₂; (SEQ ID NO:41)
(Aib², 2Thi⁹, A5c¹², Orn¹⁵)hGhrelin(1-28)-NH₂; (SEQ ID NO:41)
(Aib², 2Fua⁹, A5c¹², Orn¹⁵)hGhrelin(1-28)-NH₂; (SEQ ID NO:41)
(Aib², Apc⁹, A5c¹², Orn¹⁵)hGhrelin(1-28)-NH₂; (SEQ ID NO:41)
(Aib²,⁹, A5c¹², Orn¹⁵)hGhrelin(1-28)-NH₂; (SEQ ID NO:41)
(Aib²,¹⁰, A5c¹², Orn¹⁵)hGhrelin(1-28)-NH₂; (SEQ ID NO:44)
(Dap³(Octanesulfonyl), A5c¹², Apc¹⁶)hGhrelin(1-28)-NH₂; (SEQ ID NO:33)
(Dab³(Octanesulfonyl), A5c¹², Apc¹⁶)hGhrelin(1-28)-NH₂; (SEQ ID NO:33)
(Aib², A6c⁵, A5c¹², Apc¹⁶)hGhrelin(1-28)-NH₂; (SEQ ID NO:45)
(A6c⁵, A5c¹², Apc¹⁶)hGhrelin(1-28)-NH₂; (SEQ ID NO:46)
(Aib²,⁶, A5c¹², Apc¹⁶)hGhrelin(1-28)-NH₂; (SEQ ID NO:47)
(Aib², Act⁶, A5c¹², Apc¹⁶)hGhrelin(1-28)-NH₂; (SEQ ID NO:47)
(Aib², 3Pal⁹, A5c¹², Apc¹⁶)hGhrelin(1-28)-NH₂; (SEQ ID NO:48)
(Aib², Dmt⁷, A5c¹², Apc¹⁶)hGhrelin(1-28)-NH₂; (SEQ ID NO:49)
(Aib², Thz⁷, A5c¹², Apc¹⁶)hGhrelin(1-28)-NH₂; (SEQ ID NO:49)
(Aib², A5,12, Apc¹⁶)hGhrelin(1-28)-NH₂; (SEQ ID NO:45)
(Aib²,⁵, A5c¹², Apc¹⁶)hGhrelin(1-28)-NH₂; (SEQ ID NO:45)
(Aib², hLeu⁵, A5c¹², Apc¹⁶)hGhrelin(1-28)-NH₂; (SEQ ID NO:45)
(Aib², Cha⁵, A5c¹², Apc¹⁶)hGhrelin(1-28)-NH₂; (SEQ ID NO:45)

(Aib$^{2,6}$, A5c$^{12}$, Apc$^{16}$)hGhrelin(1-28)-NH$_2$; (SEQ ID NO:47)
(Aib$^2$, Thr$^6$, A5c$^{12}$, Apc$^{16}$)hGhrelin(1-28)-NH$_2$; (SEQ ID NO:47)
(Aib$^2$, Abu$^6$, A5c$^{12}$, Apc$^{16}$)hGhrelin(1-28)-NH$_2$; (SEQ ID NO:47)
(Aib$^2$, 4Hyp$^7$, A5c$^{12}$, Apc$^{16}$)hGhrelin(1-28)-NH$_2$; (SEQ ID NO:49)
(Aib$^2$, Pip$^7$, A5c$^{12}$, Apc$^{16}$)hGhrelin(1-28)-NH$_2$; (SEQ ID NO:49)
(Aib$^2$, Dhp$^7$, A5c$^{12}$, Apc$^{16}$)hGhrelin(1-28)-NH$_2$; (SEQ ID NO:49)
(Aib$^2$, Ktp$^7$, A5c$^{12}$, Apc$^{16}$)hGhrelin(1-28)-NH$_2$; (SEQ ID NO:49)
(Aib$^{2,8}$, A5c$^{12}$, Apc$^{16}$)hGhrelin(1-28)-NH$_2$; (SEQ ID NO:50)
(Aib$^2$, 2Pal$^9$, A5c$^{12}$, Apc$^{16}$)hGhrelin(1-28)-NH$_2$; (SEQ ID NO:48)
(Aib$^2$, 3Pal$^9$, A5c$^{12}$, Apc$^{16}$)hGhrelin(1-28)-NH$_2$; (SEQ ID NO:49)
(Aib$^2$, 4Pal$^9$, A5c$^{12}$, Apc$^{16}$)hGhrelin(1-28)-NH$_2$; (SEQ ID NO:49)
(Aib$^2$, Taz$^9$, A5c$^{12}$, Apc$^{16}$)hGhrelin(1-28)-NH$_2$; (SEQ ID NO:49)
(Aib$^2$, 2Thi$^9$, A5c$^{12}$, Apc$^{16}$)hGhrelin(1-28)-NH$_2$; (SEQ ID NO:49)
(Aib$^2$, 2Fua$^9$, A5c$^{12}$, Apc$^{16}$)hGhrelin(1-28)-NH$_2$; (SEQ ID NO:49)
(Aib$^2$, Apc$^9$, A5c$^{12}$, Apc$^{16}$)hGhrelin(1-28)-NH$_2$; (SEQ ID NO:49)
(Aib$^{2,9}$, A5c$^{12}$, Apc$^{16}$)hGhrelin(1-28)-NH$_2$; (SEQ ID NO:49)
(Aib$^{2,10}$, A5c$^{12}$, Apc$^{16}$)hGhrelin(1-28)-NH$_2$; (SEQ ID NO:51)
(Aib$^6$, A5c$^{12}$, Orn$^{15}$)hGhrelin(1-28)-NH$_2$; (SEQ ID NO:39)
(Aib$^6$, A5c$^{12}$, Orn$^{15}$)hGhrelin(1-28)-NH$_2$; (SEQ ID NO:52)
(Act$^6$, A5c$^{12}$, Orn$^{15}$)hGhrelin(1-28)-NH$_2$; (SEQ ID NO:52)
(3Pal$^9$, A5c$^{12}$, Orn$^{15}$)hGhrelin(1-28)-NH$_2$; (SEQ ID NO:53)
(Dmt$^7$, A5c$^{12}$, Orn$^{15}$)hGhrelin(1-28)-NH$_2$; (SEQ ID NO:54)
(Thz$^7$, A5c$^{12}$, Orn$^{15}$)hGhrelin(1-28)-NH$_2$; (SEQ ID NO:54)
(A5c$^5$, A5c$^{12}$, Orn$^{15}$)hGhrelin(1-28)-NH$_2$; (SEQ ID NO:39)
(Aib$^5$, A5c$^{12}$, Orn$^{15}$)hGhrelin(1-28)-NH$_2$; (SEQ ID NO:39)
(hLeu$^5$, A5c$^{12}$, Orn$^{15}$)hGhrelin(1-28)-NH$_2$; (SEQ ID NO:39)
(Cha$^5$, A5c$^{12}$, Orn$^{15}$)hGhrelin(1-28)-NH$_2$; (SEQ ID NO:39)
(Aib$^6$, A5c$^{12}$, Orn$^{15}$)hGhrelin(1-28)-NH$_2$; (SEQ ID NO:52)
(Abu$^6$, A5c$^{12}$, Orn$^{15}$)hGhrelin(1-28)-NH$_2$; (SEQ ID NO:52)
(4Hyp$^7$, A5c$^{12}$, Orn$^{15}$)hGhrelin(1-28)-NH$_2$; (SEQ ID NO:54)
(Pip$^7$, A5c$^{12}$, Orn$^{15}$)hGhrelin(1-28)-NH$_2$; (SEQ ID NO:54)
(Dhp$^7$, A5c$^{12}$, Orn$^{15}$)hGhrelin(1-28)-NH$_2$; (SEQ ID NO:54)
(Ktp$^7$, A5c$^{12}$, Orn$^{15}$)hGhrelin(1-28)-NH$_2$; (SEQ ID NO:54)
(Aib$^8$, A5c$^{12}$, Orn$^{15}$)hGhrelin(1-28)-NH$_2$; (SEQ ID NO:55)
(2Pal$^9$, A5c$^{12}$, Orn$^{15}$)hGhrelin(1-28)-NH$_2$; (SEQ ID NO:53)
(3Pal$^9$, A5c$^{12}$, Orn$^{15}$)hGhrelin(1-28)-NH$_2$; (SEQ ID NO:53)
(4Pal$^9$, A5c$^{12}$, Orn$^{15}$)hGhrelin(1-28)-NH$_2$; (SEQ ID NO:53)
(Taz$^9$, A5c$^{12}$, Orn$^{15}$)hGhrelin(1-28)-NH$_2$; (SEQ ID NO:53)
(2Thi$^9$, A5c$^{12}$, Orn$^{15}$)hGhrelin(1-28)-NH$_2$; (SEQ ID NO:53)
(2Fua$^9$, A5c$^{12}$, Orn$^{15}$)hGhrelin(1-28)-NH$_2$; (SEQ ID NO:53)
(Apc$^9$, A5c$^{12}$, Orn$^{15}$)hGhrelin(1-28)-NH$_2$; (SEQ ID NO:53)
(Aib$^9$, A5c$^{12}$, Orn$^{15}$)hGhrelin(1-28)-NH$_2$; (SEQ ID NO:53)
(Aib$^1$, A5c$^{12}$, Orn$^{15}$)hGhrelin(1-28)-NH$_2$; (SEQ ID NO:56)
(Aib$^6$, A5c$^{12}$, Apc$^6$)hGhrelin(1-28)-NH$_2$; (SEQ ID NO:57)
(A5c$^5$, A5c$^{12}$, Apc$^6$)hGhrelin(1-28)-NH$_2$; (SEQ ID NO:46)
(Act$^6$, A5c$^{12}$, Apc$^6$)hGhrelin(1-28)-NH$_2$; (SEQ ID NO:57)
(3Pal$^9$, A5c$^{12}$, Apc$^{16}$)hGhrelin(1-28)-NH$_2$; (SEQ ID NO:58)
(Dmt$^7$, A5c$^{12}$, Apc$^{16}$)hGhrelin(1-28)-NH$_2$; (SEQ ID NO:59)
(Thz$^7$, A5c$^{12}$, Apc$^{16}$)hGhrelin(1-28)-NH$_2$; (SEQ ID NO:59)
(Aib$^5$, A5c$^{12}$, Apc$^{16}$)hGhrelin(1-28)-NH$_2$; (SEQ ID NO:46)
(hLeu$^5$, A5c$^{12}$, Apc$^{16}$)hGhrelin(1-28)-NH$_2$; (SEQ ID NO:46)
(Cha$^5$, A5c$^{12}$, Apc$^{16}$)hGhrelin(1-28)-NH$_2$; (SEQ ID NO:46)
(Abu$^6$, A5c$^{12}$, Apc$^{16}$)hGhrelin(1-28)-NH$_2$; (SEQ ID NO:57)
(4Hyp$^7$, A5c$^{12}$, Apc$^{16}$)hGhrelin(1-28)-NH$_2$; (SEQ ID NO:59)
(Pip$^7$, A5c$^{12}$, Apc$^{16}$)hGhrelin(1-28)-NH$_2$; (SEQ ID NO:59)
(Dhp$^7$, A5c$^{12}$, Apc$^{16}$)hGhrelin(1-28)-NH$_2$; (SEQ ID NO:59)
(Ktp$^7$, A5c$^{12}$, Apc$^{16}$)hGhrelin(1-28)-NH$_2$; (SEQ ID NO:59)
(Aib$^8$, A5c$^{12}$, Apc$^{16}$)hGhrelin(1-28)-NH$_2$; (SEQ ID NO:60)
(2Pal$^9$, A5c$^{12}$, Apc$^{16}$)hGhrelin(1-28)-NH$_2$; (SEQ ID NO:58)
(3Pal$^9$, A5c$^{12}$, Apc$^{16}$)hGhrelin(1-28)-NH$_2$; (SEQ ID NO:58)
(4Pal$^9$, A5c$^{12}$, Apc$^{16}$)hGhrelin(1-28)-NH$_2$; (SEQ ID NO:58)
(Taz$^9$, A5c$^{12}$, Apc$^{16}$)hGhrelin(1-28)-NH$_2$; (SEQ ID NO:58)
(2Thi$^9$, A5c$^{12}$, Apc$^{16}$)hGhrelin(1-28)-NH$_2$; (SEQ ID NO:58)
(2Fua$^9$, A5c$^{12}$, Apc$^{16}$)hGhrelin(1-28)-NH$_2$; (SEQ ID NO:58)
(Apc$^9$, A5c$^{12}$, Apc$^{16}$)hGhrelin(1-28)-NH$_2$; (SEQ ID NO:58)
(Aib$^9$, A5c$^{12}$, Apc$^{16}$)hGhrelin(1-28)-NH$_2$; (SEQ ID NO:58)
(Aib$^{10}$, A5c$^{12}$, Apc$^{16}$)hGhrelin(1-28)-NH$_2$; (SEQ ID NO:61)

(Aib², Glu³(NH-Hexyl), A6c⁵)hGhrelin(1-28)-NH₂; (SEQ ID NO:62)
(Glu³(NH-Hexyl), A6c⁵)hGhrelin(1-28)-NH₂; (SEQ ID NO:63)
(Aib²,⁶, Glu³(NH-Hexyl))hGhrelin(1-28)-NH₂; (SEQ ID NO:64)
(Aib², Glu³(NH-Hexyl), Act⁶)hGhrelin(1-28)-NH₂; (SEQ ID NO:64)
(Aib², Glu³(NH-Hexyl), 3Pal⁹)hGhrelin(1-28)-NH₂; (SEQ ID NO:65)
(Aib², Glu³(NH-Hexyl), Dmt⁷)hGhrelin(1-28)-NH₂; (SEQ ID NO:66)
(Aib², Glu³(NH-Hexyl), Thz⁷)hGhrelin(1-28)-NH₂; (SEQ ID NO:66)
(Aib², Glu³(NH-Hexyl), A5c⁵)hGhrelin(1-28)-NH₂; (SEQ ID NO:62)
(Aib²,⁵, Glu³(NH-Hexyl))hGhrelin(1-28)-NH₂; (SEQ ID NO:62)
(Aib², Glu³(NH-Hexyl), hLeu⁵)hGhrelin(1-28)-NH₂; (SEQ ID NO:62)
(Aib², Cha⁵)hGhrelin(1-28)-NH₂; (SEQ ID NO:2)
(Aib²,⁶, Glu³(NH-Hexyl))hGhrelin(1-28)-NH₂; (SEQ ID NO:64)
(Aib², Glu³(NH-Hexyl), Thr⁶)hGhrelin(1-28)-NH₂; (SEQ ID NO:64)
(Aib², Glu³(NH-Hexyl), Abu⁶)hGhrelin(1-28)-NH₂; (SEQ ID NO:64)
(Aib², Glu³(NH-Hexyl), 4Hyp⁷)hGhrelin(1-28)-NH₂; (SEQ ID NO:66)
(Aib², Glu³(NH-Hexyl), Pip⁷)hGhrelin(1-28)-NH₂; (SEQ ID NO:66)
(Aib², Glu³(NH-Hexyl), Dhp⁷)hGhrelin(1-28)-NH₂; (SEQ ID NO:66)
(Aib², Glu³(NH-Hexyl), Ktp⁷)hGhrelin(1-28)-NH₂; (SEQ ID NO:66)
(Aib²,⁸, Glu³(NH-Hexyl))hGhrelin(1-28)-NH₂; (SEQ ID NO:67)
(Aib², Glu³(NH-Hexyl), 2Pal⁹)hGhrelin(1-28)-NH₂; (SEQ ID NO:65)
(Aib², Glu³(NH-Hexyl), 3Pal⁹)hGhrelin(1-28)-NH₂; (SEQ ID NO:65)
(Aib², Glu³(NH-Hexyl), 4Pal⁹)hGhrelin(1-28)-NH₂; (SEQ ID NO:65)
(Aib², Glu³(NH-Hexyl), Taz⁹)hGhrelin(1-28)-NH₂; (SEQ ID NO:65)
(Aib², Glu³(NH-Hexyl), 2Thi⁹)hGhrelin(1-28)-NH₂; (SEQ ID NO:65)
(Aib², Glu³(NH-Hexyl), 2Fua⁹)hGhrelin(1-28)-NH₂; (SEQ ID NO:65)
(Aib², Glu³(NH-Hexyl), Apc⁹)hGhrelin(1-28)-NH₂; (SEQ ID NO:65)
(Aib²,⁹, Glu³(NH-Hexyl))hGhrelin(1-28)-NH₂; (SEQ ID NO:65)
(Aib²,¹⁰, Glu³(NH-Hexyl))hGhrelin(1-28)-NH₂; (SEQ ID NO:68)
(Glu³(NH-Hexyl), Aib⁶)hGhrelin(1-28)-NH₂; (SEQ ID NO:69)
(Glu³(NH-Hexyl), A5c⁵)hGhrelin(1-28)-NH₂; (SEQ ID NO:63)
(Glu³(NH-Hexyl), Act⁶)hGhrelin(1-28)-NH₂; (SEQ ID NO:69)
(Glu³(NH-Hexyl), 3Pal⁹)hGhrelin(1-28)-NH₂; (SEQ ID NO:70)
(Glu³(NH-Hexyl), Dmt⁷)hGhrelin(1-28)-NH₂; (SEQ ID NO:71)
(Glu³(NH-Hexyl), Thz⁷)hGhrelin(1-28)-NH₂; (SEQ ID NO:71)
(Glu³(NH-Hexyl), Aib⁵)hGhrelin(1-28)-NH₂; (SEQ ID NO:63)
(Glu³(NH-Hexyl), hLeu⁵)hGhrelin(1-28)-NH₂; (SEQ ID NO:63)
(Glu³(NH-Hexyl), Cha⁵)hGhrelin(1-28)-NH₂; (SEQ ID NO:63)
(Glu³(NH-Hexyl), Thr⁶)hGhrelin(1-28)-NH₂; (SEQ ID NO:69)
(Glu³(NH-Hexyl), Abu⁶)hGhrelin(1-28)-NH₂; (SEQ ID NO:69)
(Glu³(NH-Hexyl), 4Hyp⁷)hGhrelin(1-28)-NH₂; (SEQ ID NO:71)
(Glu³(NH-Hexyl), Pip⁷)hGhrelin(1-28)-NH₂; (SEQ ID NO:71)
(Glu³(NH-Hexyl), Dhp⁷)hGhrelin(1-28)-NH₂; (SEQ ID NO:71)
(Glu³(NH-Hexyl), Ktp⁷)hGhrelin(1-28)-NH₂; (SEQ ID NO:71)
(Glu³(NH-Hexyl), Aib⁸)hGhrelin(1-28)-NH₂; (SEQ ID NO:36)
(Glu³(NH-Hexyl), 2Pal⁹)hGhrelin(1-28)-NH₂; (SEQ ID NO:70)
(Glu³(NH-Hexyl), 3Pal⁹)hGhrelin(1-28)-NH₂; (SEQ ID NO:70)
(Glu³(NH-Hexyl), 4Pal⁹)hGhrelin(1-28)-NH₂; (SEQ ID NO:70)
(Glu³(NH-Hexyl), Taz⁹)hGhrelin(1-28)-NH₂; (SEQ ID NO:70)
(Glu³(NH-Hexyl), 2Thi⁹)hGhrelin(1-28)-NH₂; (SEQ ID NO:70)
(Glu³(NH-Hexyl), 2Fua⁹)hGhrelin(1-28)-NH₂; (SEQ ID NO:70)
(Glu³(NH-Hexyl), Apc⁹)hGhrelin(1-28)-NH₂; (SEQ ID NO:70)
(Glu³(NH-Hexyl), Aib⁹)hGhrelin(1-28)-NH₂; (SEQ ID NO:70)
(Glu³(NH-Hexyl), Aib¹⁰)hGhrelin(1-28)-NH₂; (SEQ ID NO:37)
(Aib², Glu³(NH-Hexyl), A6c⁵, A5c¹², Orn¹⁵)hGhrelin(1-28)-NH₂; (SEQ ID NO:72)
(A6c⁵, Glu³(NH-Hexyl), A5c¹², Orn¹⁵)hGhrelin(1-28)-NH₂; (SEQ ID NO:73)
(Aib²,⁶, Glu³(NH-Hexyl), A5c¹², Orn¹⁵)hGhrelin(1-28)-NH₂; (SEQ ID NO:74)
(Aib², Glu³(NH-Hexyl), Act⁶, A5c¹², Orn¹⁵)hGhrelin(1-28)-NH₂; (SEQ ID NO:74)
(Aib², Glu³(NH-Hexyl), 3Pal⁹, A5c¹², Orn¹⁵)hGhrelin(1-28)-NH₂; (SEQ ID NO:75)
(Aib², Glu³(NH-Hexyl), Dmt⁷, A5c¹², Orn¹⁵)hGhrelin(1-28)-NH₂; (SEQ ID NO:76)
(Aib², Glu³(NH-Hexyl), Thz⁷, A5c¹², Orn¹⁵)hGhrelin(1-28)-NH₂; (SEQ ID NO:76)
(Aib², Glu³(NH-Hexyl), A5c⁵, A5c¹², Orn¹⁵)hGhrelin(1-28)-NH₂; (SEQ ID NO:72)
(Aib²,⁵, Glu³(NH-Hexyl), A5c¹², Orn¹⁵)hGhrelin(1-28)-NH₂; (SEQ ID NO:72)
(Aib², hLeu⁵, A5c¹², Orn¹⁵)hGhrelin(1-28)-NH₂; (SEQ ID NO:38)
(Aib², Glu³(NH-Hexyl), Cha⁵, A5c¹², Orn¹⁵)hGhrelin(1-28)-NH₂; (SEQ ID NO:72)
(Aib²,⁶, Glu³(NH-Hexyl), A5c¹², Orn¹⁵)hGhrelin(1-28)-NH₂; (SEQ ID NO:74)
(Aib², Glu³(NH-Hexyl), Thr⁶, A5c¹², Orn¹⁵)hGhrelin(1-28)-NH₂; (SEQ ID NO:74)
(Aib², Glu³(NH-Hexyl), Abu⁶, A5c¹², Orn¹⁵)hGhrelin(1-28)-NH₂; (SEQ ID NO:74)

(Aib², Glu³(NH-Hexyl), 4Hyp⁷, A5c¹², Orn¹⁵)hGhrelin(1-28)-NH₂; (SEQ ID NO:76)
(Aib², Glu³(NH-Hexyl), pip⁷, A5c¹², Orn¹⁵)hGhrelin(1-28)-NH₂; (SEQ ID NO:76)
(Aib², Glu³(NH-Hexyl), Dhp⁷, A5c¹², OM1,5)hGhrelin(1-28)-NH₂; (SEQ ID NO:76)
(Aib², Glu³(NH-Hexyl), Ktp⁷, A5c¹², Orn¹⁵)hGhrelin(1-28)-NH₂; (SEQ ID NO:76)
(Aib²,⁸, Glu³(NH-Hexyl), A5c¹², Orn¹⁵)hGhrelin(1-28)-NH₂; (SEQ ID NO:77)
(Aib², Glu³(NH-Hexyl), 2Pal⁹, A5c¹², Orn¹⁵)hGhrelin(1-28)-NH₂; (SEQ ID NO:75)
(Aib², Glu³(NH-Hexyl), 3Pal⁹, A5c¹², Orn¹⁵)hGhrelin(1-28)-NH₂; (SEQ ID NO:75)
(Aib², Glu³(NH-Hexyl), 4Pal⁹, A5c¹², Orn¹⁵)hGhrelin(1-28)-NH₂; (SEQ ID NO:75)
(Aib², Glu³(NH-Hexyl), Taz⁹, A5c¹², Orn¹⁵)hGhrelin(1-28)-NH₂; (SEQ ID NO:75)
(Aib², Glu³(NH-Hexyl), 2Thi⁹, A5c¹², Orn¹⁵)hGhrelin(1-28)-NH₂; (SEQ ID NO:75)
(Aib², Glu³(NH-Hexyl), 2Fua⁹, A5c¹², Orn¹⁵)hGhrelin(1-28)-NH₂; (SEQ ID NO:75)
(Aib², Glu³(NH-Hexyl), Apc⁹, A5c¹², Orn¹⁵)hGhrelin(1-28)-NH₂; (SEQ ID NO:75)
(Aib²,⁹, Glu³(NH-Hexyl), A5c¹², Orn¹⁵)hGhrelin(1-28)-NH₂; (SEQ ID NO:75)
(Aib²,¹², Glu³(NH-Hexyl), 4Pal⁹, Orn¹⁵)hGhrelin(1-28)-NH₂; (SEQ ID NO:143)
(Aib²,¹⁰, Glu³(NH-Hexyl), A5c¹², Orn¹⁵)hGhrelin(1-28)-NH₂; (SEQ ID NO:78)
(Aib², Glu³(NH-Hexyl), A6c⁵, A5c¹², Apc¹⁶)hGhrelin(1-28)-NH₂; (SEQ ID NO:79)
(Glu³(NH-Hexyl), A6c⁵, A5c¹², Apc¹⁶)hGhrelin(1-28)-NH₂; (SEQ ID NO:80)
(Aib²,⁶, Glu³(NH-Hexyl), A5c¹², Apc¹⁶)hGhrelin(1-28)-NH₂; (SEQ ID NO:81)
(Aib², Glu³(NH-Hexyl), Act⁶, A5c¹², Apc¹⁶)hGhrelin(1-28)-NH₂; (SEQ ID NO:81)
(Aib², Glu³(NH-Hexyl), 3Pal⁹, A5c¹², Apc¹⁶)hGhrelin(1-28)-NH₂; (SEQ ID NO:82)
(Aib², Glu³(NH-Hexyl), Dmt⁷, A5c¹², Apc¹⁶)hGhrelin(1-28)-NH₂; (SEQ ID NO:83)
(Aib², Glu³(NH-Hexyl), Thz⁷, A5c¹², Apc¹⁶)hGhrelin(1-28)-NH₂; (SEQ ID NO:83)
(Aib², Glu³(NH-Hexyl), A5c⁵,¹², Apc¹⁶)hGhrelin(1-28)-NH₂; (SEQ ID NO:79)
(Aib²,⁵, Glu³(NH-Hexyl), A5c¹², Apc¹⁶)hGhrelin(1-28)-NH₂; (SEQ ID NO:79)
(Aib², Glu³(NH-Hexyl), hLeu⁵, A5c¹², Apc¹⁶)hGhrelin(1-28)-NH₂; (SEQ ID NO:79)
(Aib², Glu³(NH-Hexyl), Cha⁵, A5c¹², Apc¹⁶)hGhrelin(1-28)-NH₂; (SEQ ID NO:79)
(Aib²,⁶, Glu³(NH-Hexyl), A5c¹², Apc¹⁶)hGhrelin(1-28)-NH₂; (SEQ ID NO:81)
(Aib², Glu³(NH-Hexyl), Thr⁶, A5c¹², Apc¹⁶)hGhrelin(1-28)-NH₂; (SEQ ID NO:81)
(Aib², Glu³(NH-Hexyl), Abu⁶, A5c¹², Apc¹⁶)hGhrelin(1-28)-NH₂; (SEQ ID NO:81)
(Aib², Glu³(NH-Hexyl), 4Hyp⁷, A5c¹², Apc¹⁶)hGhrelin(1-28)-NH₂; (SEQ ID NO:83)
(Aib², Glu³(NH-Hexyl), Pip⁷, A5c¹², Apc¹⁶)hGhrelin(1-28)-NH₂; (SEQ ID NO:83)
(Aib², Glu³(NH-Hexyl), Dhp⁷, A5c¹², Apc¹⁶)hGhrelin(1-28)-NH₂; (SEQ ID NO:83)
(Aib², Glu³(NH-Hexyl), Ktp⁷, A5c¹², Apc¹⁶)hGhrelin(1-28)-NH₂; (SEQ ID NO:83)
(Aib²,⁸, Glu³(NH-Hexyl), A5c¹², Apc¹⁶)hGhrelin(1-28)-NH₂; (SEQ ID NO:84)
(Aib², Glu³(NH-Hexyl), 2Pal⁹, A5c¹², Apc¹⁶)hGhrelin(1-28)-NH₂; (SEQ ID NO:82)
(Aib², Glu³(NH-Hexyl), 3Pal⁹, A5c¹², Apc¹⁶)hGhrelin(1-28)-NH₂; (SEQ ID NO:82)
(Aib², Glu³(NH-Hexyl), 4Pal⁹, A5c¹², Apc¹⁶)hGhrelin(1-28)-NH₂; (SEQ ID NO:82)
(Aib², Glu³(NH-Hexyl), Taz⁹, A5c¹², Apc¹⁶)hGhrelin(1-28)-NH₂; (SEQ ID NO:82)
(Aib², Glu³(NH-Hexyl), 2Thi⁹, A5c¹², Apc¹⁶)hGhrelin(1-28)-NH₂; (SEQ ID NO:82)
(Aib², Glu³(NH-Hexyl), 2Fua⁹, A5c¹², Apc¹⁶)hGhrelin(1-28)-NH₂; (SEQ ID NO:82)
(Aib², Glu³(NH-Hexyl), Apc⁹, A5c¹², Apc¹⁶)hGhrelin(1-28)-NH₂; (SEQ ID NO:82)
(Aib²,⁹, Glu³(NH-Hexyl), A5c¹², Apc¹⁶)hGhrelin(1-28)-NH₂; (SEQ ID NO:82)
(Aib²,¹⁰, Glu³(NH-Hexyl), A5c¹², Apc¹⁶)hGhrelin(1-28)-NH₂; (SEQ ID NO:85)
(Aib²)hGhrelin(1-28)-NH₂; (SEQ ID NO:10)
(Glu³(NH-Hexyl))hGhrelin(1-28)-NH₂; (SEQ ID NO:85)
(Aib², Glu³(O-Hexyl))hGhrelin(1-28)-NH₂; (SEQ ID NO:87)
(Aib², Glu³(NH-Hexyl))hGhrelin(1-28)-NH₂; (SEQ ID NO:87)
(Dap³(1-Octanesulfonyl))hGhrelin(1-28)-NH₂; (SEQ ID NO:1)
(Aib², Dap³(1-Octanesulfonyl))hGhrelin(1-28)-NH₂; (SEQ ID NO:89)
(Aib¹, Dap³(1-Octanesulfonyl))hGhrelin(1-28)-NH₂; (SEQ ID NO:88)
(Ava², Dap³(1-Octanesulfonyl))hGhrelin(2-28)-NH₂; (SEQ ID NO:144)
(Ac-Gly¹, Aib²)hGhrelin(1-28)-NH₂; (SEQ ID NO:93)
(Ac-Gly¹, Aib², Glu³(NH-Hexyl))hGhrelin(1-5)-NH₂; (SEQ ID NO:94)
(Ac-Gly¹, Aib², Glu³(NH-Hexyl))hGhrelin(1-6)-NH₂; (SEQ ID NO:95)
(Ac-Gly¹, Aib², Glu³(NH-Hexyl))hGhrelin(1-7)-NH₂; (SEQ ID NO:96)
(Ac-Gly¹, Aib², Glu³(NH-Hexyl))hGhrelin(1-28)-NH₂; (SEQ ID NO:97)
(Ac-Gly¹, Aib², Glu³(NH-Hexyl), Arg⁸)hGhrelin(1-8)-NH₂; (SEQ ID NO:98)
(Ac-Gly¹, Aib², Glu³(NH-Hexyl), Lys⁸)hGhrelin(1-8)-NH₂; and (SEQ ID NO:98)
(Ac-Gly¹, Aib²,¹⁰, Glu³(NH-Hexyl))hGhrelin(1-28)-NH₂; (SEQ ID NO:99)
(n-Octanoyl-Gly¹)hGhrelin(1-28)-NH₂ (SEQ ID NO:100):
or a pharmaceutically acceptable salt thereof.

5. The compound of claim 4, selected from:
(4Hyp⁷)hGhrelin(1-28)-NH₂; (SEQ ID NO:15)
(Aib⁸)hGhrelin(1-28)-NH₂; (SEQ ID NO:16)
(Taz⁹)hGhrelin(1-28)-NH₂; (SEQ ID NO:14)
(3Pal⁹)hGhrelin(1-28)-NH₂; (SEQ ID NO:14)
(4Pal)hGhrelin(1-28)-NH₂; (SEQ ID NO:14)
(2Thi⁹)hGhrelin(1-28)-NH₂; (SEQ ID NO:14)
(Aib², Glu³(NH-Hexyl), Taz⁹)hGhrelin(1-28)-NH₂; (SEQ ID NO:65)
(Aib², Glu³(NH-Hexyl), Thr⁶)hGhrelin(1-28)-NH₂; (SEQ ID NO:103)
(Aib², Glu³(NH-Hexyl), 2Thi⁹)hGhrelin(1-28)-NH₂; (SEQ ID NO:65)
(Aib², Thr⁶)hGhrelin(1-28)-NH₂; (SEQ ID NO:104)
(Aib², 2Thi⁹)hGhrelin(1-28)-NH₂; (SEQ ID NO:8)

(Glu³(NH-hexyl))hGhrelin(1-28)-NH₂; (SEQ ID NO:106)
(Aib²)hGhrelin(1-28)-NH₂; (SEQ ID NO:10)
(Aib², Glu³(NH-hexyl))hGhrelin(1-28)-NH₂; (SEQ ID NO:109)
(Aib²,⁶)hGhrelin(1-28)-NH₂; (SEQ ID NO:4)
(Aib²,Act⁶)hGhrelin(1-28)-NH₂; (SEQ ID NO:4)
(A5c²)hGhrelin(1-28)-NH₂; (SEQ ID NO:10)
(Act²)hGhrelin(1-28)-NH₂; (SEQ ID NO:10)
(Aib², A6c⁵)hGhrelin(1-28)-NH₂; (SEQ ID NO:2)
(A6c⁵)hGhrelin(1-28)-NH₂; (SEQ ID NO:3)
(Aib², 3Pal⁹)hGhrelin(1-28)-NH₂; (SEQ ID NO:8)
(Dap³(Octanesulfonyl))hGhrelin(1-28)-NH₂; (SEQ ID NO:1)
(Aib²,Thz⁷)hGhrelin(1-28)-NH₂; (SEQ ID NO:9)
(Aib², Cha⁵)hGhrelin(1-28)-NH₂; (SEQ ID NO:2)
(Aib², Abu⁶)hGhrelin(1-28)-NH₂; (SEQ ID NO:4)
(Aib², 4Hyp⁷)hGhrelin(1-28)-NH₂; (SEQ ID NO:9)
(Aib², Taz⁹)hGhrelin(1-28)-NH₂; (SEQ ID NO:8)
(Aib², 4Pal⁹)hGhrelin(1-28)-NH₂; (SEQ ID NO:8)
(Aib², Dhp⁷)hGhrelin(1-28)-NH₂; (SEQ ID NO:9)
(Aib²,⁸)hGhrelin(1-28)-NH₂; (SEQ ID NO:11)
(Aib², Pip⁷)hGhrelin(1-28)-NH₂; (SEQ ID NO:9)
(Aib², Glu³(NH-Hexyl), 4Hyp⁷)hGhrelin(1-28)-NH₂; (SEQ ID NO:66)
(Aib²,⁸, Glu³(NH-Hexyl))hGhrelin(1-28)-NH₂; (SEQ ID NO:67)
(Aib²,¹², Glu³(NH-Hexyl), 4Pal⁹, Orn¹⁵)hGhrelin(1-28)-NH₂; (SEQ ID NO:111)
(Aib², Glu³(NH-Hexyl), 4Pal⁹)hGhrelin(1-28)-NH₂; (SEQ ID NO:65)
(Aib², Glu³(NH-Hexyl), 3Pal⁹)hGhrelin(1-28)-NH₂; (SEQ ID NO:65)
(Aib²,¹⁰)hGhrelin(1-28)-NH₂; (SEQ ID NO:12)
(Aib²,¹⁰, Glu³(NH-Hexyl))hGhrelin(1-28)-NH₂; (SEQ ID NO:68)
(Ac-Gly¹, Aib²)hGhrelin(1-28)-NH₂; (SEQ ID NO:93)
(Ac-Gly¹, Aib², Glu³(NH-hexyl))hGhrelin(1-5)-NH₂; (SEQ ID NO:94)
(Ac-Gly¹, Aib², Glu³(NH-hexyl))hGhrelin(1-6)-NH₂; (SEQ ID NO:95)
(Ac-Gly¹, Aib², Glu³(NH-hexyl))hGhrelin(1-7)-NH₂; (SEQ ID NO:96)
(Ac-Gly¹, Aib², Glu³(NH-hexyl))hGhrelin(1-28)-NH₂; (SEQ ID NO:97)
(Ac-Gly¹, Aib², Glu³(NH-hexyl), Arg⁸)hGhrelin(1-8)-NH₂; (SEQ ID NO:98)
(Ac-Gly¹, Aib², Glu³(NH-hexyl), Lys⁸)hGhrelin(1-8)-NH₂; (SEQ ID NO:98)
(Ac-Gly¹, Aib²,¹⁰, Glu³(NH-Hexyl))hGhrelin(1-28)-NH₂; and (SEQ ID NO:99)
(n-Butyryl-Gly¹, Aib², Glu³(NH-hexyl))hGhrelin(1-28)-NH₂; (SEQ ID NO:101)
or a pharmaceutically acceptable salt thereof.

6. The compound of claim 5, selected from:
(Aib², 3Pal⁹)hGhrelin(1-28)-NH₂; (SEQ ID NO:8)
(Aib², 4Hyp⁷)hGhrelin(1-28)-NH₂; (SEQ ID NO:9)
(Aib², Taz⁹)hGhrelin(1-28)-NH₂; (SEQ ID NO:8)
(Aib², Dhp⁷)hGhrelin(1-28)-NH₂; (SEQ ID NO:9)
(Aib²,⁸)hGhrelin(1-28)-NH₂; (SEQ ID NO:11)
(Aib²,⁸, Glu³(NH-Hexyl))hGhrelin(1-28)-NH₂; (SEQ ID NO:112)
(Aib²,¹⁰, Glu³(NH-Hexyl))hGhrelin(1-28)-NH₂; (SEQ ID NO:113)
(Aib², Glu³(NH-hexyl))hGhrelin(1-28)-NH₂; (SEQ ID NO:114)
(Ac-Gly¹, Aib²)hGhrelin(1-28)-NH₂; (SEQ ID NO:93)
(Ac-Gly¹, Aib², Glu³(NH-hexyl))hGhrelin(1-5)-NH₂; (SEQ ID NO:94)
(Ac-Gly¹, Aib², Glu³(NH-hexyl))hGhrelin(1-6)-NH₂; (SEQ ID NO:95)
(Ac-Gly¹, Aib², Glu³(NH-hexyl))hGhrelin(1-7)-NH₂; (SEQ ID NO:96)
(Ac-Gly¹, Aib², Glu³(NH-hexyl))hGhrelin(1-28)-NH₂; (SEQ ID NO:97)
(Ac-Gly¹, Aib², Glu³(NH-hexyl), Arg⁸)hGhrelin(1-8)-NH₂; (SEQ ID NO:98)
(Ac-Gly¹, Aib², Glu³(NH-hexyl), Lys⁸)hGhrelin(1-8)-NH₂; (SEQ ID NO:98)
(Ac-Gly¹, Aib²,¹⁰, Glu³(NH-Hexyl))hGhrelin(1-28)-NH₂; and (SEQ ID NO:99)
(n-Butyryl-Gly¹, Aib², Glu³(NH-hexyl))hGhrelin(1-28)-NH₂; (SEQ ID NO:101)
or a pharmaceutically acceptable salt thereof.

7. The compound of claim 6, selected from:
(Aib², 3Pal⁹)hGhrelin(1-28)-NH₂; (SEQ ID NO:8)
(Aib², 4Hyp⁷)hGhrelin(1-28)-NH₂; (SEQ ID NO:9)
(Aib², Taz⁹)hGhrelin(1-28)-NH₂; (SEQ ID NO:8)
(Aib², Dhp⁷)hGhrelin(1-28)-NH₂; (SEQ ID NO:9)
(Aib²,⁸)hGhrelin(1-28)-NH₂; (SEQ ID NO:11)
(Aib²,⁸, Glu³(NH-Hexyl))hGhrelin(1-28)-NH₂; (SEQ ID NO:115)
(Aib², Glu³(NH-hexyl))hGhrelin(1-28)-NH₂; (SEQ ID NO:114)
(Ac-Gly¹, Aib²)hGhrelin(1-28)-NH₂; (SEQ ID NO:93)
(Ac-Gly¹, Aib², Glu³(NH-hexyl))hGhrelin(1-5)-NH₂; (SEQ ID NO:94)
(Ac-Gly¹, Aib², Glu³(NH-hexyl))hGhrelin(1-6)-NH₂; (SEQ ID NO:95)
(Ac-Gly¹, Aib², Glu³(NH-hexyl))hGhrelin(1-7)-NH₂; (SEQ ID NO:96)
(Ac-Gly¹, Aib², Glu³(NH-hexyl))hGhrelin(1-28)-NH₂; (SEQ ID NO:97)
(Ac-Gly¹, Aib², Glu³(NH-hexyl), Arg⁸)hGhrelin(1-8)-NH₂; (SEQ ID NO:98)
(Ac-Gly¹, Aib², Glu³(NH-hexyl), Lys⁸)hGhrelin(1-8)-NH₂; (SEQ ID NO:98)
(Ac-Gly¹, Aib²,¹⁰, Glu³(NH-Hexyl))hGhrelin(1-28)-NH₂; and (SEQ ID NO:99)
(n-Butyryl-Gly¹, Aib², Glu³(NH-hexyl))hGhrelin(1-28)-NH₂; (SEQ ID NO:101)
or a pharmaceutically acceptable salt thereof.

8. The compound of claim 1, selected from:
(Aib²)hGhrelin(1-28)-NH₂; and (SEQ ID NO:10)
(Glu³(NH-Hexyl))hGhrelin(1-28)-NH₂; (SEQ ID NO:106)
or a pharmaceutically acceptable salt thereof.

9. A compound according to the formula:
(des-Ser²)hGhrelin(1-28)-NH₂ or
(des-Gly¹, des-Ser²)hGhrelin(1-28)-NH₂, or a pharmaceutically acceptable salt thereof.

10. The compound of claim 1, selected from:
(Aib², Ser³)hGhrelin(1-28)-NH₂; (SEQ ID NO:10)
(Aib²,⁶, Ser³)hGhrelin(1-28)-NH₂; (SEQ ID NO:4)
(A5c⁵, Ser³)hGhrelin(1-28)-NH₂; (SEQ ID NO:3)
(Aib², Ser³, 3Pal⁹)hGhrelin(1-28)-NH₂; (SEQ ID NO:8)
(Aib², Ser³, Thz⁷)hGhrelin(1-28)-NH₂; (SEQ ID NO:9)
(Aib², Ser³, Cha⁵)hGhrelin(1-28)-NH₂; (SEQ ID NO:2)
(Aib², Ser³, Abu⁶)hGhrelin(1-28)-NH₂; (SEQ ID NO:4)
(Aib², Ser³, 4Hyp⁷)hGhrelin(1-28)-NH₂; (SEQ ID NO:9)
(Aib², Ser³, Taz⁹)hGhrelin(1-28)-NH₂; (SEQ ID NO:8)
(Aib²,⁴, Ser³, 4Pal⁹)hGhrelin(1-28)-NH₂; (SEQ ID NO:117)

(Aib², Ser³, Dhp⁷)hGhrelin(1-28)-NH₂; (SEQ ID NO:9)
(Aib²,⁸, Ser³)hGhrelin(1-28)-NH₂; (SEQ ID NO:11)
(Aib², Ser³, Pip⁷)hGhrelin(1-28)-NH₂; (SEQ ID NO:9)
(Ac-Gly¹, Aib²,⁰, Ser³)hGhrelin(1-28)-NH₂; (SEQ ID NO:118)
(Aib²,¹⁰, Ser³)hGhrelin(1-28)-NH₂; (SEQ ID NO:12)
(n-Butyryl-Gly¹, Aib², Ser³)hGhrelin(1-28)-NH₂; (SEQ ID NO:119)
(Ac-Gly¹, Aib², Ser³)hGhrelin(1-28)-NH₂; (SEQ ID NO:93)
(Aib², Ser³, Tic⁷)hGhrelin(1-28)-NH₂; (SEQ ID NO:9)
(Ac-Gly¹, Aib², Ser³, Arg⁸)hGhrelin(1-8)-NH₂; (SEQ ID NO:120)
(Ser³, Aib⁸)hGhrelin(1-28)-NH₂; (SEQ ID NO:121)
(Ser³, Taz⁹)hGhrelin(1-28)-NH₂; (SEQ ID NO:14)
(Ser³, 3Pal⁹)hGhrelin(1-28)-NH₂; (SEQ ID NO:14)
(Ser³, 4Pal⁹)hGhrelin(1-28)-NH₂; (SEQ ID NO:14)
(Aib², Ser³, 2Thi⁹)hGhrelin(1-28)-NH₂; (SEQ ID NO:8)
(Ser³, 2Thi⁹)hGhrelin(1-28)-NH₂; (SEQ ID NO:14)
(Ser³, 4Hyp⁷)hGhrelin(1-28)-NH₂; (SEQ ID NO:15)
(Aib², Ser³, Tic⁷)hGhrelin(1-28)-NH₂; (SEQ ID NO:9)
(Aib², Thr³)hGhrelin(1-28)-NH₂; (SEQ ID NO:123)
(Aib²,⁶, Thr³)hGhrelin(1-28)-NH₂; (SEQ ID NO:124)
(A5c⁵, Thr³)hGhrelin(1-28)-NH₂; (SEQ ID NO:125)
(Aib², Thr³, 3Pal⁹)hGhrelin(1-28)-NH₂; (SEQ ID NO:126)
(Aib², Thr³, Thz⁷)hGhrelin(1-28)-NH₂; (SEQ ID NO:127)
(Aib², Thr³, Cha⁵)hGhrelin(1-28)-NH₂; (SEQ ID NO:128)
(Aib², Thr³, Abu⁶)hGhrelin(1-28)-NH₂; (SEQ ID NO:124)
(Aib², Thr³, 4Hyp⁷)hGhrelin(1-28)-NH₂; (SEQ ID NO:127)
(Aib², Thr³, Taz⁹)hGhrelin(1-28)-NH₂; (SEQ ID NO:126)
(Aib²,⁴, Thr³, 4Pal⁹)hGhrelin(1-28)-NH₂; (SEQ ID NO:129)
(Aib², Thr³, Dhp⁷)hGhrelin(1-28)-NH₂; (SEQ ID NO:127)
(Aib²,⁸, Thr³)hGhrelin(1-28)-NH₂; (SEQ ID NO:130)
(Aib², Thr³, Pip⁷)hGhrelin(1-28)-NH₂; (SEQ ID NO:127)
(Ac-Gly¹, Aib²,¹⁰, Thr³)hGhrelin(1-28)-NH₂; (SEQ ID NO:131)
(Aib²,¹⁰, Thr³)hGhrelin(1-28)-NH₂; (SEQ ID NO:131)
(n-Butyryl-Gly¹, Aib², Thr³)hGhrelin(1-28)-NH₂; (SEQ ID NO:133)
(Ac-Gly¹, Aib², Thr³)hGhrelin(1-28)-NH₂; (SEQ ID NO:133)
(Aib², Thr³, Tic⁷)hGhrelin(1-28)-NH₂; (SEQ ID NO:127)
(Ac-Gly¹, Aib², Thr³, Arg⁸)hGhrelin(1-8)-NH₂; (SEQ ID NO:134)
(Thr³, Aib⁸)hGhrelin(1-28)-NH₂; (SEQ ID NO:135)
(Thr³, Taz⁹)hGhrelin(1-28)-NH₂; (SEQ ID NO:136)
(Thr³, 3Pal⁹)hGhrelin(1-28)-NH₂; (SEQ ID NO:136)
(Thr³, 4Pal⁹)hGhrelin(1-28)-NH₂; (SEQ ID NO:136)
(Aib², Thr³, 2Thi⁹)hGhrelin(1-28)-NH₂; (SEQ ID NO:126)
(Thr³, 2Thi⁹)hGhrelin(1-28)-NH₂; (SEQ ID NO:136)
(Thr³, 4Hyp⁷)hGhrelin(1-28)-NH₂; (SEQ ID NO:137)
(Aib², Thr³, Tic⁷)hGhrelin(1-28)-NH₂; (SEQ ID NO:127)
(Aib², Tic⁷)hGhrelin(1-28)-NH₂; and (SEQ ID NO:9)
(Ac-Gly¹, Glu³(NH-Hexyl)hGhrelin(1-28)-NH₂; (SEQ ID NO:138)
or a pharmaceutically acceptable salt thereof.

11. The compound of claim 1, selected from:
(Aib², Ser³)hGhrelin(1-28)-NH₂; (SEQ ID NO:10)
(Aib²,⁶, Ser³)hGhrelin(1-28)-NH₂; (SEQ ID NO:4)
(A5c⁵, Ser³)hGhrelin(1-28)-NH₂; (SEQ ID NO:3)
(Aib², Ser³, 3Pal⁹)hGhrelin(1-28)-NH₂; (SEQ ID NO:8)
(Aib², Ser³, Thz⁷)hGhrelin(1-28)-NH₂; (SEQ ID NO:9)
(Aib², Ser³, Cha⁵)hGhrelin(1-28)-NH₂; (SEQ ID NO:2)
(Aib², Ser³, Abu⁶)hGhrelin(1-28)-NH₂; (SEQ ID NO:4)
(Aib², Ser³, 4Hyp⁷)hGhrelin(1-28)-NH₂; (SEQ ID NO:9)
(Aib², Ser³, Taz⁹)hGhrelin(1-28)-NH₂; (SEQ ID NO:8)
(Aib²,⁴, Ser³, 4Pal⁹)hGhrelin(1-28)-NH₂; (SEQ ID NO:117)
(Aib², Ser³, Dhp⁷)hGhrelin(1-28)-NH₂; (SEQ ID NO:9)
(Aib²,⁸, Ser³)hGhrelin(1-28)-NH₂; (SEQ ID NO:117)
(Aib², Ser³, Pip⁷)hGhrelin(1-28)-NH₂; (SEQ ID NO:9)
(Ac-Gly¹, Aib²,⁰, Ser³)hGhrelin(1-28)-NH₂; (SEQ ID NO:139)
(Aib²,¹⁰, Ser³)hGhrelin(1-28)-NH₂; (SEQ ID NO:12)
(n-Butyryl-Gly¹, Aib², Ser³)hGhrelin(1-28)-NH₂; (SEQ ID NO:140)
(Ac-Gly¹, Aib², Ser³)hGhrelin(1-28)-NH₂; (SEQ ID NO:93)
(Aib², Ser³, Tic⁷)hGhrelin(1-28)-NH₂; (SEQ ID NO:9)
(Ac-Gly¹, Aib², Ser³, Arg⁸)hGhrelin(1-8)-NH₂; (SEQ ID NO:120)
(Ser³, Aib⁸)hGhrelin(1-28)-NH₂; (SEQ ID NO:121)
(Ser³, Taz⁹)hGhrelin(1-28)-NH₂; (SEQ ID NO:14)
(Ser³, 3Pal⁹)hGhrelin(1-28)-NH₂; (SEQ ID NO:14)
(Ser³, 4Pal⁹)hGhrelin(1-28)-NH₂; (SEQ ID NO:14)
(Aib², Ser³, 2Thi⁹)hGhrelin(1-28)-NH₂; (SEQ ID NO:8)
(Ser³, 2Thi⁹)hGhrelin(1-28)-NH₂; (SEQ ID NO:14)
(Ser³, 4Hyp⁷)hGhrelin(1-28)-NH₂; (SEQ ID NO:15) and
(Aib², Ser³, Tic⁷)hGhrelin(1-28)-NH₂ (SEQ ID NO:9);
or a pharmaceutically acceptable salt thereof.

12. The compound of claim 1, selected from:
(Aib², Ser³)hGhrelin(1-28)-NH₂; (SEQ ID NO:10)
(Aib²,⁶, Ser³)hGhrelin(1-28)-NH₂; (SEQ ID NO:4)
(A5c⁵, Ser³)hGhrelin(1-28)-NH₂; (SEQ ID NO:3)
(Aib², Ser³, 3Pal⁹)hGhrelin(1-28)-NH₂; (SEQ ID NO:8)
(Aib², Ser³, Thz⁷)hGhrelin(1-28)-NH₂; (SEQ ID NO:9)
(Aib², Ser³, Cha⁵)hGhrelin(1-28)-NH₂; (SEQ ID NO:2)
(Aib², Ser³, Abu⁶)hGhrelin(1-28)-NH₂; (SEQ ID NO:4)
(Aib², Ser³, 4Hyp⁷)hGhrelin(1-28)-NH₂; (SEQ ID NO:9)
(Aib², Ser³, Taz⁹)hGhrelin(1-28)-NH₂; (SEQ ID NO:8)
(Aib²,⁴, Ser³, 4Pal⁹)hGhrelin(1-28)-NH₂; (SEQ ID NO:117)
(Aib², Ser³, Dhp⁷)hGhrelin(1-28)-NH₂; (SEQ ID NO:9)
(Aib²,⁸, Ser³)hGhrelin(1-28)-NH₂; (SEQ ID NO:11)
(Aib², Ser³, Pip⁷)hGhrelin(1-28)-NH₂; (SEQ ID NO:9)
(Ac-Gly¹, Aib²,¹⁰, Ser³)hGhrelin(1-28)-NH₂; (SEQ ID NO:139)
(Aib²,¹⁰, Ser³)hGhrelin(1-28)-NH₂; (SEQ ID NO:12)
(n-Butyryl-Gly¹, Aib², Ser³)hGhrelin(1-28)-NH₂; (SEQ ID NO:119)
(Ac-Gly¹, Aib², Ser³)hGhrelin(1-28)-NH₂; (SEQ ID NO:93)
(Aib², Ser³, Tic⁷)hGhrelin(1-28)-NH₂; (SEQ ID NO:9)
(Ac-Gly¹, Aib², Ser³, Arg¹)hGhrelin(–8)-NH₂; (SEQ ID NO:120)
(Ser³, Aib⁸)hGhrelin(1-28)-NH₂; (SEQ ID NO:121)
(Ser³, Taz⁹)hGhrelin(1-28)-NH₂; (SEQ ID NO:14)
(Ser³, 3Pal⁹)hGhrelin(1-28)-NH₂; (SEQ ID NO:14)
(Ser³, 4 Pal⁹)hGhrelin(1-28)-NH₂; (SEQ ID NO:14)
(Aib², Ser³, 2Thi⁹)hGhrelin(1-28)-NH₂; (SEQ ID NO:8)
(Ser³, 2Thi⁹)hGhrelin(1-28)-NH₂; (SEQ ID NO:14)
(Ser³, 4Hyp⁷)hGhrelin(1-28)-NH₂; (SEQ ID NO:15) and
(Aib², Ser³, Tic⁷)hGhrelin(1-28)-NH₂ (SEQ ID NO:9);
or a pharmaceutically acceptable salt thereof.

13. The compound of claim 1, selected from:
(Aib$^2$, Tic$^7$)hGhrelin(1-28)-NH$_2$; and (SEQ ID NO:9)
(Ac-Gly$^1$, Glu$^3$(NH-Hexyl))hGhrelin(1-28)-NH$_2$; (SEQ ID NO:138)
or a pharmaceutically acceptable salt thereof.

14. A compound selected from (Thr$^6$)hGhrelin(1-28)-NH$_2$ (SEQ ID NO:13), (Thr$^6$, A5c$^{12}$, Orn$^{15}$)hGhrelin(1-28)-NH$_2$ (SEQ ID NO:52) or (Thr$^6$, A5c$^{12}$, Apc$^{16}$)hGhrelin(1-28)-NH$_2$ (SEQ ID NO:57) or a pharmaceutically acceptable salt thereof.

15. A pharmaceutical formulation comprising a compound from any one of claims 1-13 and 14 with a pharmaceutically acceptable carrier.

16. A method of treating cachexia in an individual in need thereof comprising administering to said individual a compound selected from any one of claims 1-13 and 14 or a pharmaceutically acceptable salt thereof in an amount sufficient to treat cachexia.

* * * * *

UNITED STATES PATENT AND TRADEMARK OFFICE
CERTIFICATE OF CORRECTION

PATENT NO. : 7,589,058 B2 Page 1 of 1
APPLICATION NO. : 10/522398
DATED : September 15, 2009
INVENTOR(S) : Dong et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 965 days.

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,589,058 B2
APPLICATION NO. : 10/522398
DATED : September 15, 2009
INVENTOR(S) : Zheng Xin Dong and Yeelena Shen It is certified that error appears in the above-identified patent and that said Letters Patent is hereby corrected as shown below:

Column 47, lines 54-59, Claim 4, that portion of the claim which reads:
"(A6c$^5$, A5c$^{12}$, Orn$^{15}$)hGhrelin(1-28)-NH$_2$; (SEQ ID NO:39)
(Aib$^2$, Act$^6$, A5c$^{12}$, Orn$^{15}$)hGhrelin(1-28)-NH$_2$; (SEQ ID NO:40)
(Aib$^2$, Act$^6$, A5c$^{12}$, Orn$^{15}$)hGhrelin(1-28)-NH$_2$; (SEQ ID NO:40)"
should read:
"(A6c$^5$, A5c$^{12}$, Orn$^{15}$)hGhrelin(1-28)-NH$_2$; (SEQ ID NO:39)
(Aib$^{2,6}$, A5c$^{12}$, Orn$^{15}$)hGhrelin(1-28)-NH$_2$; (SEQ ID NO:40)
(Aib$^2$, Act$^6$, A5c$^{12}$, Orn$^{15}$)hGhrelin(1-28)-NH$_2$; (SEQ ID NO:40)"

Column 50, lines 19-25, Claim 4, that portion of the claim which reads:
"(Aib$^1$, A5c$^{12}$, Orn$^{15}$)hGhrelin(1-28)-NH$_2$; (SEQ ID NO:56)
(Aib$^6$, A5c$^{12}$, Apc$^6$)hGhrelin(1-28)-NH$_2$; (SEQ ID NO:57)
(A5c$^5$, A5c$^{12}$, Apc$^6$)hGhrelin(1-28)-NH$_2$; (SEQ ID NO:46)
(Act$^6$, A5c$^{12}$, Apc$^6$)hGhrelin(1-28)-NH$_2$; (SEQ ID NO:57)"
should read:
"(Aib$^{10}$, A5c$^{12}$, Orn$^{15}$)hGhrelin(1-28)-NH$_2$; (SEQ ID NO:56)
(Aib$^6$, A5c$^{12}$, Apc$^{16}$)hGhrelin(1-28)-NH$_2$; (SEQ ID NO:57)
(A5c$^5$, A5c$^{12}$, Apc$^{16}$)hGhrelin(1-28)-NH$_2$; (SEQ ID NO:46)
(Act$^6$, A5c$^{12}$, Apc$^{16}$)hGhrelin(1-28)-NH$_2$; (SEQ ID NO:57)"

Column 53, lines 3-5, Claim 4, that portion of the claim which reads:
"(Aib$^2$, Glu$^3$(NH-Hexyl), pip$^7$, A5c$^{12}$, Orn$^{15}$)hGhrelin(1-28)-NH$_2$; (SEQ ID NO:76)
(Aib$^2$, Glu$^3$(NH-Hexyl), Dhp$^7$, A5c$^{12}$, OM1,5)hGhrelin(1-28)-NH$_2$; (SEQ ID NO:76)"
should read:
"(Aib$^2$, Glu$^3$(NH-Hexyl), Pip$^7$, A5c$^{12}$, Orn$^{15}$)hGhrelin(1-28)-NH$_2$; (SEQ ID NO:76)
(Aib$^2$, Glu$^3$(NH-Hexyl), Dhp$^7$, A5c$^{12}$, Orn$^{15}$)hGhrelin(1-28)-NH$_2$; (SEQ ID NO:76)"

Signed and Sealed this
Twenty-fourth Day of July, 2012

David J. Kappos
*Director of the United States Patent and Trademark Office*

CERTIFICATE OF CORRECTION (continued)
U.S. Pat. No. 7,589,058 B2

Column 56, lines 53-55, Claim 6, that portion of the claim which reads:
"(des-Ser$^2$)hGhrelin(1-28)-NH$_2$ or
(des-Gly$^1$, des-Ser$^2$)hGhrelin(1-28)-NH$_2$, or a pharmaceutically acceptable salt thereof."
should read:
"(des-Ser$^2$)hGhrelin(1-28)-NH$_2$ (SEQ ID NO:116) or
(des-Gly$^1$, des-Ser$^2$)hGhrelin(1-28)-NH$_2$ (SEQ ID NO:116), or a pharmaceutically acceptable salt thereof."

Column 57, line 4, Claim 10, that portion of the claim which reads:
"(Ac-Gly$^1$, Aib$^{2,0}$, Ser$^3$)hGhrelin(1-28)-NH$_2$; (SEQ ID"
should read:
"(Ac-Gly$^1$, Aib$^{2,10}$, Ser$^3$)hGhrelin(1-28)-NH$_2$; (SEQ ID"

Column 58, line 8, Claim 11, that portion of the claim which reads "SEQ ID NO:117" should read "SEQ ID NO:11"

Column 58, line 10, Claim 11, that portion of the claim which reads
"(Ac-Gly$^1$, Aib$^{2,0}$, Ser$^3$)hGhrelin(1-28)-NH$_2$; (SEQ ID NO:139)"
should read:
"(Ac-Gly$^1$, Aib$^{2,10}$, Ser$^3$)hGhrelin(1-28)-NH$_2$; (SEQ ID NO:139)"

Column 58, line 56, Claim 12, that portion of the claim which reads:
"(Ac-Gly$^1$, Aib$^2$, Ser$^3$, Arg$^1$)hGhrelin(-8)-NH$_2$; (SEQ ID NO:120)"
should read:
"(Ac-Gly$^1$, Aib$^2$, Ser$^3$, Arg$^8$)hGhrelin(1-8)-NH$_2$; (SEQ ID NO:120)"

```
                        SEQUENCE LISTING

<160> NUMBER OF SEQ ID NOS: 6

<210> SEQ ID NO 1
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: residue is D-Trp
<220> FEATURE:
<221> NAME/KEY: MISC_FEATURE
<222> LOCATION: (5)..(5)
<223> OTHER INFORMATION: residue is D-Phe
<220> FEATURE:
<221> NAME/KEY: MOD_RES
<222> LOCATION: (6)..(6)
<223> OTHER INFORMATION: AMIDATION

<400> SEQUENCE: 1

His Xaa Ala Trp Xaa Lys
1               5

<210> SEQ ID NO 2
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: residue is D-(2')-Nal  (D-(2')- naphthyl
      alanine)
<220> FEATURE:
<221> NAME/KEY: MISC_FEATURE
<222> LOCATION: (5)..(5)
<223> OTHER INFORMATION: residue is D-Phe
<220> FEATURE:
<221> NAME/KEY: MOD_RES
<222> LOCATION: (6)..(6)
<223> OTHER INFORMATION: AMIDATION

<400> SEQUENCE: 2

Ala His Xaa Trp Xaa Lys
1               5

<210> SEQ ID NO 3
<211> LENGTH: 6
<212> TYPE: PRT
<213> ORGANISM: Artificial
<220> FEATURE:
<223> OTHER INFORMATION: Synthetic Peptide
<220> FEATURE:
```

```
<221> NAME/KEY: MISC_FEATURE
<222> LOCATION: (1)..(1)
<223> OTHER INFORMATION: residue is D-Ala
<220> FEATURE:
<221> NAME/KEY: MISC_FEATURE
<222> LOCATION: (2)..(2)
<223> OTHER INFORMATION: reidue is D-(2')-Nal (D-(2')-naphthyl alanine)
<220> FEATURE:
<221> NAME/KEY: MISC_FEATURE
<222> LOCATION: (5)..(5)
<223> OTHER INFORMATION: residue is D-Nal (D-naphthyl alanine)
<220> FEATURE:
<221> NAME/KEY: MOD_RES
<222> LOCATION: (6)..(6)
<223> OTHER INFORMATION: AMIDATION

<400> SEQUENCE: 3

Xaa Xaa Ala Trp Xaa Lys
1               5

<210> SEQ ID NO 4
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: reside is D-2-MeTrp
<220> FEATURE:
<221> NAME/KEY: MISC_FEATURE
<222> LOCATION: (5)..(5)
<223> OTHER INFORMATION: reside is D-Phe
<220> FEATURE:
<221> NAME/KEY: MOD_RES
<222> LOCATION: (6)..(6)
<223> OTHER INFORMATION: AMIDATION

<400> SEQUENCE: 4

His Xaa Ala Trp Xaa Lys
1               5

<210> SEQ ID NO 5
<211> LENGTH: 27
<212> TYPE: DNA
<213> ORGANISM: Artificial
<220> FEATURE:
<223> OTHER INFORMATION: gene specific primer for hGHS-R

<400> SEQUENCE: 5
atgtggaacg cgacgcccag cgaagag                                   27

<210> SEQ ID NO 6
<211> LENGTH: 27
<212> TYPE: DNA
<213> ORGANISM: Artificial
<220> FEATURE:
<223> OTHER INFORMATION: gene specific primer of hGHS-R

<400> SEQUENCE: 6
tcatgtatta atactagatt ctgtcca                                   27
```